(12) United States Patent
Wang et al.

(10) Patent No.: US 8,038,990 B2
(45) Date of Patent: Oct. 18, 2011

(54) COMPOSITIONS AND METHODS FOR THE PREVENTION AND REMOVAL OF BIOFILMS ON INERT AND BIOLOGICAL SURFACES

(75) Inventors: Hua Wang, Columbus, OH (US); Hongliang Luo, Columbus, OH (US)

(73) Assignee: The Ohio State University, Columbus, OH (US)

( * ) Notice: Subject to any disclaimer, the term of this patent is extended or adjusted under 35 U.S.C. 154(b) by 610 days.

(21) Appl. No.: 11/421,705

(22) Filed: Jun. 1, 2006

(65) Prior Publication Data

US 2007/0059295 A1 Mar. 15, 2007

Related U.S. Application Data

(60) Provisional application No. 60/686,629, filed on Jun. 1, 2005.

(51) Int. Cl.
*A01N 63/00* (2006.01)
*A61K 38/46* (2006.01)
*C12N 9/00* (2006.01)
*C12N 9/50* (2006.01)
*C12N 9/52* (2006.01)
*C12N 1/20* (2006.01)

(52) U.S. Cl. ............... 424/93.45; 424/94.6; 435/183; 435/219; 435/220; 435/252.3; 536/23.2

(58) Field of Classification Search .................. None
See application file for complete search history.

(56) References Cited

U.S. PATENT DOCUMENTS

| | | |
|---|---|---|
| 5,451,369 A | 9/1995 | Daeschel et al. |
| 5,877,272 A | 3/1999 | Vandenbergh et al. |
| 6,039,984 A | 3/2000 | Bowling et al. |
| 6,187,990 B1 | 2/2001 | Runeman et al. |
| 6,306,391 B1 | 10/2001 | Modi et al. |
| 6,630,197 B1 | 10/2003 | Wood et al. |
| 6,692,779 B2 | 2/2004 | Dominques et al. |
| 6,703,025 B1 | 3/2004 | Patti et al. |
| 6,892,732 B2 | 5/2005 | Wang et al. |
| 6,942,849 B2 | 9/2005 | Neeser et al. |
| 2002/0012637 A1 | 1/2002 | Neeser et al. |
| 2002/0025309 A1 | 2/2002 | Modi et al. |
| 2003/0170184 A1 | 9/2003 | Comelli et al. |
| 2003/0228297 A1 | 12/2003 | Chang et al. |
| 2003/0229000 A1 | 12/2003 | Merritt et al. |
| 2004/0057908 A1 | 3/2004 | Bowen et al. |
| 2004/0072748 A1 | 4/2004 | Balaban |
| 2004/0132164 A1 | 7/2004 | Doyle et al. |
| 2004/0217052 A1 | 11/2004 | Baldridge et al. |
| 2004/0265313 A1 | 12/2004 | Storey et al. |
| 2005/0053702 A1 | 3/2005 | Elsser |
| 2005/0059295 A1 | 3/2005 | Chen et al. |

OTHER PUBLICATIONS

Chica et al. Curr Opin Biotechnol. Aug. 2005;16(4):378-84.*
Christensson et al. J Appl Microbiol. Aug. 2001;91(2):334-43.*
Accession Q9AIQ2, Jun. 1, 2001.*
Habimana et al. BMC Microbiol. May 2, 2007;7:36.*
Busscher et al., "Preliminary observations on influence of dairy products on biofilm removal from silicone rubber voice prostheses in vitro", J. Dairy Sci. vol. 83, No. 4 (2000), pp. 641-647.
Busscher et al., "Preliminary observations on influence of dairy products on biofilm removal from silicone rubber voice prostheses in vitro", Exogenous factors influencing voice prosthetic biofilm University of Groningen Dissertation (FREE)(Mar. 2004), Ch. 5, pp. 59-72.
Free et al., "Biofilm formation on voice prostheses: influence of dairy products in vitro", Exogenous factors influencing voice prosthetic biofilm University of Groningen Dissertation (FREE)(Mar. 2004), Ch. 6, pp. 73-87.
Klaenhammer et al., "Improved lysis of group *N streptococci* for isolation and rapid characterization of plasmid deoxyribonucleic acid", Appl. and Environ. Microbiol., vol. 35, No. 3 (Mar. 1978), pp. 592-600.
Luo et al., "High-frequency conjugation system facilitates biofilm formation and pAMbeta1 transmission by *Lactococcus lactis*", Appl. and Environ. Microbiol., vol. 71 (Jun. 2005), pp. 1-9.
Marsh et al., "A three-tiered approach to differentiate *Listeria monocytogenes* biofilm-forming abilities", FEMS Microbiology Letters 11258 (2003), pp. 1-8 (Initial online publication).
Stentz et al, "Controlled expression of CluA in *Lactococcus lactis* and its role in conjugation", Microbiology, vol. 150 (Aug. 2004), (Pt 8), pp. 2503-2512.
van der Mei et al., "Effect of probiotic bacteria on prevalence of yeasts in oropharyngeal biofilms on silicone rubber voice prostheses in vitro", J. Med. Microbiol., vol. 49, No. 8 (Aug. 2000), pp. 713-718.
Wang et al., "Analysis of the Physical and functional characteristics of cell clumping in lactose-positive transconjugants of *Lactococcus lactis* ssp. *lactis* ML3", J. Diary Sci., vol. 77 (1994), pp. 375-384.
Wang et al., "Interactions between oral bacteria: inhibition of *Streptococcus mutans* bacteriocin production by *Streptococcus gordonii*", Appl. and Environ. Microbiol., pp. 71, No. 1 (Jan. 2005), pp. 354-362.
Wolz et al., "Transcription of Clumping Factdor A in Attached and Unattached *Staphylococcus aureus* in vitro and durin device-related infection", Infect. Immun., vol. 70, No. 6 (Jun. 2002), pp. 2758-2762.

* cited by examiner

*Primary Examiner* — Christian Fronda
(74) *Attorney, Agent, or Firm* — Calfee, Halter & Griswold LLP

(57) ABSTRACT

Organisms, compositions, and methods for at least partially reducing the formation of a biofilm and/or at least partially removing a biofilm are provided. The organisms, compositions, and methods may be used on biotic and abiotic surfaces.

35 Claims, 11 Drawing Sheets

```
  1   makanigkll  ltgvvggaia  lggsaiyqst  tnqsannsrs  nttstkvsnv  svnvntdvts
 61   aikkvsnsvv  svmnyqkdns  qssdfssifg  gnsgsssstd  glqlssegsg  viykksggda
121   yvvtnyhvia  gnssldvlls  ggqkvkasvv  gydeytdlav  lkissehvkd  vatfadsskl
181   tigepaiavg  splgsqfant  ategilsats  rqvtltqeng  qttninaiqt  daainpgnsg
241   galiniegqv  igitqskitt  tedgstsveg  lgfaipsndv  vniinklead  gkisrpalgi
301   rmvdlsqlst  ndssqlklps  svtggvvvys  vqsglpaasa  glkagdvitk  vgdtavtsst
361   dlqsalyshn  indtvkvtyy  rdgksntadv  klskstsdle  tsspsssn
```

Fig. 1

```
  1   mqrkkkglsf  llagtvalga  lavlpvgeiq  akaaisqqtk  gsslantvta  atakqaatdt
 61   taattnqaia  tqlaakgidy  nklnkvqqqd  iyvdvivqms  aapasengtl  rtdysstaei
121   qqetnkviaa  qasvkaaveq  vtqqtagesy  gyvvngfstk  vrvvdipklk  qiagvktvtl
181   akvyyptdak  ansmanvqav  wsnykykgeg  tvvsvidsgi  dpthkdmrls  ddkdvkltks
241   dvekftdtvk  hgryfnskvp  ygfnyadnnd  titddkvdeq  hgmhvagiig  angtgddpak
301   svvgvapeaq  llamkvftns  dtsattgsdt  lvsaiedsak  igadvlnmsl  gsdsgnqtle
361   dpeiaavqna  nesgtaavis  agnsgtsgsa  tegvnkdyyg  lqdnemvgtp  gtsrgattva
421   saentdvitq  avtitdgtgl  qlgpetiqls  sndftgsfdq  kkfyvvkdas  gnlskgkvad
481   ytadakgkia  ivkrgeltfd  dkqkyaqaag  aagliivnnd  gtatpvtsma  ltttfptfgl
541   ssvtgqklvd  wvtahpddsl  gvkialtlvp  nqkytedkms  dftsygpvsn  lsfkpditap
601   ggniwstqnn  ngytnmsgts  maspfiagsq  allkqalnnk  nnpfyayykq  lkgtaltdfl
661   ktvemntaqp  indinynnvi  vsprrqgagl  vdvkaaidal  eknpstvvae  ngypavelkd
721   ftstdktfkl  tftnrtthel  tyqmdsntdt  navytsatdp  nsgvlydkki  dgaaikagsn
781   itvpagktaq  ieftlslpks  fdqqqfvegf  lnfkgsdgsr  lnlpymgffg  dwndgkivds
841   lngityspag  gnfgtvpllt  nkntgtqyyg  gmvtdadgnq  tvddqaiafs  sdknalyndi
901   smkyyllrni  snvqvdildg  qgnkvttlss  stnltktyyn  ahsqqyiyyh  apawdgtyyd
961   qrdgniktad  dgsytyrisg  vpeggdkrqv  fdvpfkldsk  aptvrhvals  aktkngktqy
1021  yltaevkddl  sgldatksvk  tainevtnld  atftdagtta  dgytkietpl  sdeqaqalgn
1081  gdnsaelylt  dnasnatdqd  asvqkpgsts  fdlivngsgi  pdkissttg  yeantqgggt
1141  ytfsgtypaa  vdgtytdaqg  kkhdlnttyd  aatnsftasm  pvtnadyaaq  vdlyadkaht
1201  qllkhfdtkv  rltaptftdl  kfnngsdqts  eatikvtgtv  sadtktvnvg  dtvaaldaqh
1261  hfsvdvpvny  gdntikviat  dedgntttteq  ktitssydpd  mlknpvtfdq  gvtfgsnefn
1321  atsakfydpk  tgiatitgkv  khptttlqvd  gkqipikddl  tfsftldlgt  lgqkpfgvvv
1381  gdttqnktfq  ealtfildav  aptlsldsst  dapvytndpn  fqitgtatdn  aqylslsing
1441  ssvasqyadi  ninsgkpghm  aidqpvklle  gknvltvavt  dsednttkn  itvyyepkkt
1501  laaptvtpst  tepaqtvtlt  anaaatgetv  qysadggkty  qdvpaagvti  tangtfkfks
```

```
1561  tdlygnespa  vdyvvtnika  ddpaqlqaak  qaltnliasa  ktlsasgkyd  datttalaaa
1621  tqkaqtaldq  tnasvdsltg  anrdlqtain  qlaaklpadk  ktsllnqlqs  vkdalgtdlg
1681  nqtdpstgkt  ftaalddlva  qaqagtqtdd  qlqatlakil  devlaklaeg  ikaatpaevg
1741  nakdaatgkt  wyadiadtlt  sgqasadasd  klahlqalqs  lktkvaaave  adktvgkgdd
1801  ttgtsdkgsg  qgtpapatgd  tgkdkgdegs  qpssggnipt  npatttstst  ddttdrngqh
1861  ttgkgalpkt  getterpafg  flgvivvilm  gvlglkrkqr  ee
```

Fig. 2

```
1    mkkkmrlkvl  lastatalll  lsgcqsnqtd  qtvatysggk  vtessfykel  kqspttktml
61   anmliyraln  haygksvstk  tvndaydsyk  qqygenfdaf  lsqngfsrss  fkeslrtnfl
121  sevalkklkk  vsesqlkaaw  ktyqpkvtvq  hiltsdedta  kqvisdlasg  kdfamlaktd
181  sidtatkdng  gkisfelnnk  tldatfkdaa  yklkngdytq  tpvkvtdgye  vikminhpak
241  gtftsskkvl  tasvyakwsr  dssimqrvis  qvlknqhvti  kdkdladald  sykklattn
```

Fig. 3

```
1    mkktlrdqll  gvskahlnwk  nktkvfiygt  aillmvapnl  assvsrasad  eegnapkvtq
61   agersgklal  nishsaldqa  isdakaagls  lkegaiqdkg  naqgtdaitk  lqkaisddya
121  sqvstikkqt  sdyktalday  nkaeadykkq  lddiqngidn  ntpgspavak  gqqltfragq
181  npkatvesvk  fsgsgdgall  kskvlgdgmt  qlskvtssdv  vsqpdfydlg  gttslfglfl
241  dagqsvtity  kdlknfslng  tsviqmkvty  knvtnarmgi  mvsrdpgnqf  qfgvetngri
301  fvnqpkalqe  slefhdgsnk  lmtfktvdss  saqfmagsln  ysksktpegg  lpptsdgynq
361  hesvsfdntl  vvgsyfpssg  vhkvsgrpts  ganatgdsws  snppstnetw  satayidyka
421  igpsldvtew  dvgtknswyg  amnlipkdgq  tsisvtwgtt  danmwallng  qlpnkiptpe
481  ppippvkpta  tyyydqatfq  tdntkavtqt  dgtdlngalv  nkqetenwvl  snevlpaghe
541  viksyvmtdp  lpegfkldle  qsktlspdyd  ltfdektntv  tltaykatle  amnkdlnqay
601  qvpketlqgq  vtkdgssfkn  dletlindyt  vnsnevevht  pdpkpeksne  nasgttingq
661  gidvnatnyy  kllwdlsgyk  giasskediv  rgfyfvdaap  dvvdvdlkni  sykdsqgkev
721  kgitakvyss  vkdapaevqk  vladakiapk  gqfvfysvdd  pqtfytnyvq  tgnnveitqp
781  mtfkegasga  yqntdyqidf  gnsyegdtvk  nnivppkvvk  qvsvdggktw  hdskdlpdtd
841  snydykldfn  ftangdytki  llgdnfessq  wtdlakakvt  dkdgndiagq  fkvlnasgkd
901  vtkdfnnhvf  qkdgkkevlq  iiftpdkisd  itslasnsdp  drlitltmsf  kdvtlkgatg
961  aelanyldke  gkivapnigq  ldttsrtvtg  dntkdkitks  nvtkvippql  tpminkyvye
```

```
1021  tgvgssinly  dkgltlpsyl  sklaqftsln  lnkdekvkvg  etvhwliatq  sgnkslmtnv
1081  vdtlpkelsf  aenmnakvfv  lkndgklgde  vtndwkienk  gqtltatpnd  ptkyffvgss
1141  tdsrvvitld  ttvneeaktg  tftniatint  kdgghkedka  nvhtkekpet  viekitgslp
1201  ktgegkaala  isifgaallg  laaylkrnwi  vstyrktvrk  irk
```

Fig. 4

```
MNKRKEVFGFRKSKVAKTLCGAVLGAALIAIADQQVLADEVTETNSTANVAVTTTGNPATNLPEAQGEATEAASQSQ
AQAGSKEGALPVEVSADDLNQAVTDAKAAGVNVVQDQTSDKGTATTAAENAQKQAEIKSDYAKQAEEIKKTTEAYKK
EVEAHQAETDKINAENKAAEDKYQEDLKAHQAEVEKINTANATAKAEYEAKLAQYQKDLAAVQKANEDSQLDYQNKL
SAYQAELARVQKANAEAKEAYEKAVKENTAKNAALQAENEAIKQRNETAKANYDAAMKQYEADLAAIKKAKEDNDAD
YQAKLAAYQAELARVQKANADAKAAYEKAVEENTAKNTAIQAENEAIKQRNAAAKATYEAALKQYEADLAAAKKANE
DSDADYQAKLAAYQTELARVQKANADAKAAYEKAVEDNKAKNAALQAENEEIKQRNAAAKTDYEAKLAKYEADLAKY
KKELAEYPAKLKAYEDEQAQIKAALVELEKNKNQDGYLSKPSAQSLVYDSEPNAQLSLTTNGKMLKASAVDEAFSHD
TAQYSKKILQPDNLNVSYLQQADDVTSSMELYGNFGDKAGWTTTVGNNTEVKFASVLLERGQSVTATYTNLEKSYYN
GKKISKAVFKYSLDSDSKFKNVDKAWLGVLPDPTLGVFASAYTGQEEKDTSIFIKNEFTFYDENDQPINFDNALLSV
ASLNRENNSIEMAKDYSGTFVKISGSSVGEKDGKIYATETLNFKQGQGGSRWTMYKNSQPGSGWDSSDAPNSWYGAG
AISMSGPTNHVTVGAISATQVVPSDPVMAVATGKRPNIWYSLNGKIRAVNVPKITKEKPTPPVAPTEPQAPTYEVEK
PLEPAPVAPTYENEPTPPVKTPDQPEPSKPEEPTYETEKPLEPAPVVPTYENEPTPPVKTPDQPEPSKPEEPTYETE
KPLEPAPVAPTYENEPTPPVKTPDQPEPSKPEEPTYDPLPTPPVAPTPKQLPTPPVVPTVHFHYSSLLAQPQINKEI
KNEDGVDIDRTLVAKQSIVKFELKTEALTAGRPKTTSFVLVDPLPTGYKFDLDATKAASTGFDTTYDEASHTVTFKA
TDETLATYNADLTKPVETLHPTVVGRVLNDGATYINNFTLTVNDAYGIKSNVVRVTTPGKPNDPDNPNNNYIKPTKV
NKNKEGLNIDGKEVLAGSTNYYELTWDLDQYKGDKSSKEAIQNGFYYVDDYPEEALDVRPDLVKVADEKGNQVSGVS
VQQYDSLEAAPKKVQDLLKKANITVKGAFQLFSADNPEEFYKQYVSTGTSLVITDPMTVKSEFGKTGGKYENKAYQI
DFGNGYATEVVVNNVPKITPKKDVTVSLDPTSENLDGQTVQLYQTFNYRLIGGFIPQNHSEELEDYSFVDDYDQAGD
QYTGNYKTFSSLNLTMKDGSVIKAGTDLTSQTTAETDAANGIVTVRSKEDSLQKISLDSPFQAETYLQMRRIAIGTF
ENTYVNTVNKVAYASNTVRTTTPIPRTPDKPTPIPTPKPKDPDKPETPKEPKVPSPKVEDPSAPIPVSVGKELTTLP
KTGTNDSSYMPYLGLAALVGVLGLGQLKRKEDESN
```

Fig. 5

MKVKKTYGFRKSKISKTLCGAVLGTVAAVSVAGQKVFADETTTTSDVDTKVVGTQTGNPATNLPEAQGSASKEAEQS
QTKLERQMVHTIEVPKTDLDQAAKDAKSAGVNVVQDADVNKGTVKTPEEAVQKETEIKEDYTKQAEDIKKTTDQYKS
DVAAHEAEVAKIKAKNQATKEQYEKDMAAHKAEVERINAANAASKTAYEAKLAQYQADLAAVQKTNAANQAAYQKAL
AAYQAELKRVQEANAAAKAAYDTAVAANNAKNTEIAAANEEIRKRNATAKAEYETKLAQYQAELKRVQEANAANEAD
YQAKLTAYQTELARVQKANADAKATYEAAVAANNAKNAALTAENTAIKQRNENAKATYEAALKQYEADLAAVKKANA
ANEADYQAKLTAYQTELARVQKANADAKAAYEAAVAANNAANAALTAENTAIKKRNADAKADYEAKLAKYQADLAKY
QKDLADYPVKLKAYEDEQTSIKAALAELEKHKNEDGNLTEPSAQNLVYDLEPNANLSLTTDGKFLKASAVDDAFSKS
TSKAKYDQKILQLDDLDITNLEQSNDVASSMELYGNFGDKAGWSTTVSNNSQVKWGSVLLERGQSATATYTNLQNSY
YNGKKISKIVYKYTVDPKSKFQGQKVWLGIFTDPTLGVFASAYTGQVEKNTSIFIKNEFTFYHEDEKPINFDNALLS
VTSLNREHNSIEMAKDYSGKFVKISGSSIGEKNGMIYATDTLNFKQGEGGSRWTMYKNSQAGSGWDSSDAPNSWYGA
GAIKMSGPNNHVTVGATSATNVMPVSDMPVVPGKDNTDGKKPNIWYSLNGKIRAVNVPKVTKEKPTPPVKPTAPTKP
TYETEKPLKPAPVAPNYEKEPTPPTRTPDQAEPNKPTPPTYETEKPLEPAPVEPSYEAEPTPPTRTPDQAEPNKPTP
PTYETEKPLEPAPVEPSYEAEPTPPTPTPDQPEPNKPVEPTYEVIPTPPTDPVYQDLPTPPSDPTVHFHYFKLAVQP
QVNKEIRNNNDINIDRTLVAKQSVVKFQLKTADLPAGRDETTSFVLVDPLPSGYQFNPEATKAASPGFDVTYDNATN
TVTFKATAATLATFNADLTKSVATIYPTVVGQVLNDGATYKNNFTLTVNDAYGIKSNVVRVTTPGKPNDPDNPNNNY
IKPTKVNKNENGVVIDGKTVLAGSTNYYELTWDLDQYKNDRSSADTIQKGFYYVDDYPEEALELRQDLVKITDANGN
EVTGVSVDNYTNLEAAPQEIRDVLSKAGIRPKGAFQIFRADNPREFYDTYVKTGIDLKIVSPMVVKKQMGQTGGSYE
NQAYQIDFGNGYASNIVINNVPKINPKKDVTLTLDPADTNNVDGQTIPLNTVFNYRLIGGIIPANHSEELFEYNFYD
DYDQTGDHYTGQYKVFAKVDITLKNGVIIKSGTELTQYTTAEVDTTKGAITIKFKEAFLRSVSIDSAFQAESYIQMK
RIAVGTFENTYINTVNGVTYSSNTVKTTTPEDPADPTDPQDPSSPRTSTVIIYKPQSTAYQPSSVQETLPNTGVTNN
AYMPLLGIIGLVTSFSLLGLKAKKD

Fig. 6

MEKGLLVDIGRKYWSIAELKRLVLLLQEHKLTHLQLHLNENEGFALNFTDSPVSKKYSENMLKELKEFAKTHEITLI
PDFDSPGHMGSLLEQNPEFALPDSNQQAVDVTNPAVIDWIMGIIDKIVDIFPDSDTFHIGADEFIDFRQIEKYPYLV
EKTREKYGNKASGLEFYYDYVNQLTEHLQKKGKQVRIWNDGFLRKDLQSLVPLNKNVEVCYWTNWDKGMAEVKEWLT
KGYTLINFCDNDLYYVLGEEAGYSYPTAEKLEREGKIQKFSGQQYLNQEEMKAVRGTYFSIWADNAAAKSVSEILDD
LSKVLPVFMKIYGGNDE

Fig. 7

```
1    mfvkllrsva  iglivgaill  vampslrsln  plstpqfdst  detpasynla  vrraapavvn
61   vynrglntns  hnqleirtlg  sgvimdqrgy  iitnkhvind  adqiivalqd  grvfeallvg
121  sdsltdlavl  kinatgglpt  ipinarrvph  igdvvlaign  pynlgqtitq  giisatgrig
181  lnptgrqnfl  qtdasinhgn  sggalvnslg  elmgintlsf  dksndgetpe  gigfaipfql
241  atkimdklir  dgrvirgyig  iggreiaplh  aqgggidqlq  givvnevspd  gpaanagiqv
301  ndliisvdnk  paisaletmd  qvaeirpgsv  ipvvvmrddk  qltlqvtiqe  ypatn
```

Fig. 8

MILGNMRGELSMVENQNNNQRPRKNSNAKIITTAAIVGVVGGLIGGGVSYYAADQMNNATDTTTAQTSVSSNSSKVS
EKSAKTSGTMTTAYNDVKGAVVSVINLKRQSSSSSANSLYSSLFGDDSDSSSGKSGKLETYSEGSSVVYMKSNGKGY
IVTNNHVISGSDAVQVQLANGKTVSAKVVGKDSTTDLAVLSIDAKYVTQTAEFGDSKSLQAGQTVIAVGSPLGSEYA
STVTQGIISAPARTISTSSGNQQTVIQTDAAINPGNSGGALVNSAGQVIGINSMKLAQSSDGTSVEGMGFAIPSNEV
VTIVNELVKKGKITRPQLGVRVVALEGIPEAYRSRLKIKSNLKSGIYVASINKNSSAANAGMKSGDVITKVDGKKVD
DVASLHSILYSHKVGDTVNITINRNGRDVNLKVKLEGN

Fig. 9

MKKFNWKKIVAPIAMLIIGLLGGLLGAFILLTAAGVSFTNTTDTGVKTAKTVYTNITDTTKAVKKVQNAVVSVINYQ
EGSSSDSLNDLYGRIFGGGDSSDSSQENSKDSDGLQVAGEGSGVIYKKDGKEAYIVTNNHVVDGAKKLEIMLSDGSK
ITGELVGKDTYSDLAVVKVSSDKITTVAEFADSNSLTVGEKAIAIGSPLGTEYANSVTEGIVSSLSRTITMQNDNGE
TVSTNAIQTDAAINPGNSGGALVNIEGQVIGINSSKISSTSAVAGSAVEGMGFAIPSNDVVEIINQLEKDGKVTRPA
LGISIADLNSLSSSATSKLDLPDEVKSGVVVGSVQKGMPADGKLQEYDVITEIDGKKISSKTDIQTNLYSHSIGDTI
KVTFYRGKDKKTVDLKLTKSTEDISD

Fig. 10

A
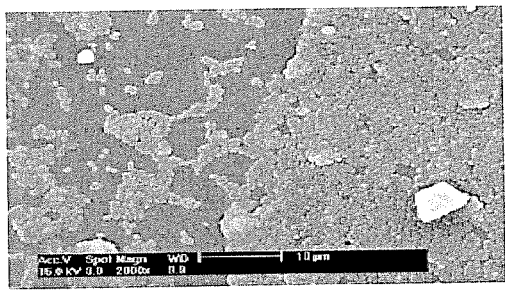
B
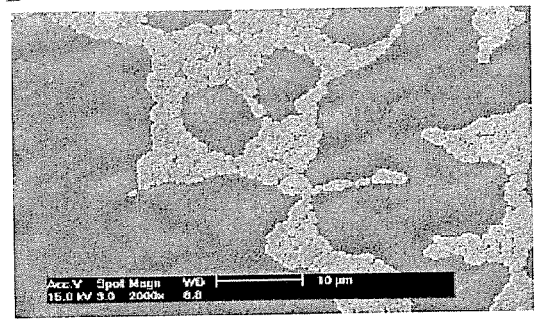
C
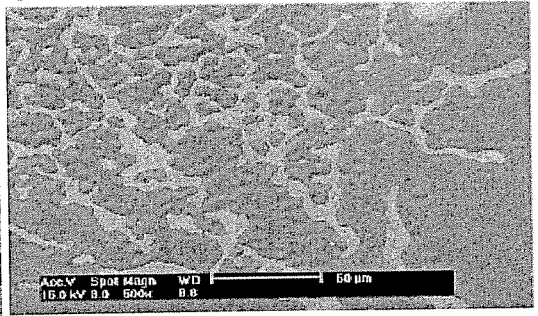
D
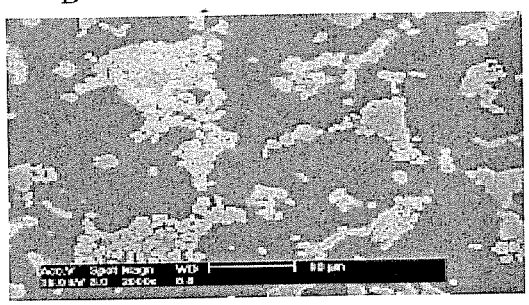
F
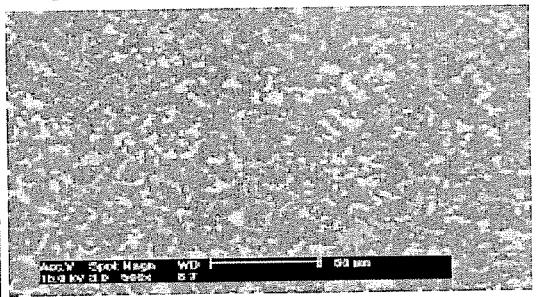
G
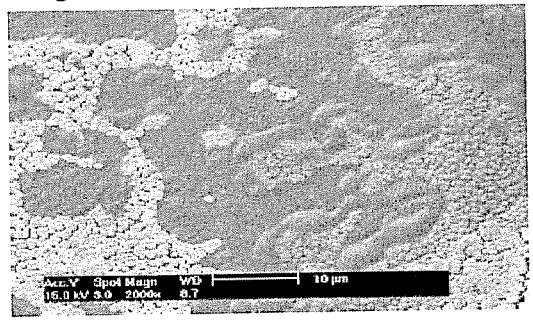
H
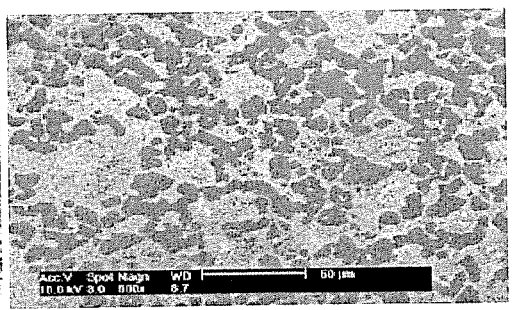
Fig. 17

SEQUENCE LISTING

```
<160> NUMBER OF SEQ ID NOS: 41

<210> SEQ ID NO 1
<211> LENGTH: 408
<212> TYPE: PRT
<213> ORGANISM: Lactococcus lactis

<400> SEQUENCE: 1

Met Ala Lys Ala Asn Ile Gly Lys Leu Leu Thr Gly Val Val Gly
 1               5                  10                  15

Gly Ala Ile Ala Leu Gly Gly Ser Ala Ile Tyr Gln Ser Thr Thr Asn
                20                  25                  30

Gln Ser Ala Asn Asn Ser Arg Ser Asn Thr Thr Ser Thr Lys Val Ser
            35                  40                  45

Asn Val Ser Val Asn Val Asn Thr Asp Val Thr Ser Ala Ile Lys Lys
        50                  55                  60

Val Ser Asn Ser Val Val Ser Val Met Asn Tyr Gln Lys Asp Asn Ser
65                  70                  75                  80

Gln Ser Ser Asp Phe Ser Ser Ile Phe Gly Gly Asn Ser Gly Ser Ser
                    85                  90                  95

Ser Ser Thr Asp Gly Leu Gln Leu Ser Ser Glu Gly Ser Gly Val Ile
                100                 105                 110

Tyr Lys Lys Ser Gly Gly Asp Ala Tyr Val Val Thr Asn Tyr His Val
            115                 120                 125

Ile Ala Gly Asn Ser Ser Leu Asp Val Leu Leu Ser Gly Gly Gln Lys
        130                 135                 140

Val Lys Ala Ser Val Val Gly Tyr Asp Glu Tyr Thr Asp Leu Ala Val
145                 150                 155                 160

Leu Lys Ile Ser Ser Glu His Val Lys Asp Val Ala Thr Phe Ala Asp
                    165                 170                 175

Ser Ser Lys Leu Thr Ile Gly Glu Pro Ala Ile Ala Val Gly Ser Pro
                180                 185                 190

Leu Gly Ser Gln Phe Ala Asn Thr Ala Thr Glu Gly Ile Leu Ser Ala
            195                 200                 205

Thr Ser Arg Gln Val Thr Leu Thr Gln Glu Asn Gly Gln Thr Thr Asn
        210                 215                 220

Ile Asn Ala Ile Gln Thr Asp Ala Ala Ile Asn Pro Gly Asn Ser Gly
225                 230                 235                 240

Gly Ala Leu Ile Asn Ile Glu Gly Gln Val Ile Gly Ile Thr Gln Ser
                    245                 250                 255

Lys Ile Thr Thr Thr Glu Asp Gly Ser Thr Ser Val Glu Gly Leu Gly
                260                 265                 270

Phe Ala Ile Pro Ser Asn Asp Val Val Asn Ile Ile Asn Lys Leu Glu
            275                 280                 285
```

-continued

```
Ala Asp Gly Lys Ile Ser Arg Pro Ala Leu Gly Ile Arg Met Val Asp
            290                 295                 300

Leu Ser Gln Leu Ser Thr Asn Asp Ser Ser Gln Leu Lys Leu Pro Ser
305                 310                 315                 320

Ser Val Thr Gly Gly Val Val Val Tyr Ser Val Gln Ser Gly Leu Pro
                325                 330                 335

Ala Ala Ser Ala Gly Leu Lys Ala Gly Asp Val Ile Thr Lys Val Gly
            340                 345                 350

Asp Thr Ala Val Thr Ser Ser Thr Asp Leu Gln Ser Ala Leu Tyr Ser
        355                 360                 365

His Asn Ile Asn Asp Thr Val Lys Val Thr Tyr Tyr Arg Asp Gly Lys
    370                 375                 380

Ser Asn Thr Ala Asp Val Lys Leu Ser Lys Ser Thr Ser Asp Leu Glu
385                 390                 395                 400

Thr Ser Ser Pro Ser Ser Ser Asn
                405
```

<210> SEQ ID NO 2
<211> LENGTH: 1902
<212> TYPE: PRT
<213> ORGANISM: Lactococcus lactis

<400> SEQUENCE: 2

```
Met Gln Arg Lys Lys Lys Gly Leu Ser Phe Leu Leu Ala Gly Thr Val
 1               5                  10                  15

Ala Leu Gly Ala Leu Ala Val Leu Pro Val Gly Glu Ile Gln Ala Lys
             20                  25                  30

Ala Ala Ile Ser Gln Gln Thr Lys Gly Ser Ser Leu Ala Asn Thr Val
         35                  40                  45

Thr Ala Ala Thr Ala Lys Gln Ala Ala Thr Asp Thr Thr Ala Ala Thr
     50                  55                  60

Thr Asn Gln Ala Ile Ala Thr Gln Leu Ala Ala Lys Gly Ile Asp Tyr
 65                  70                  75                  80

Asn Lys Leu Asn Lys Val Gln Gln Gln Asp Ile Tyr Val Asp Val Ile
                 85                  90                  95

Val Gln Met Ser Ala Ala Pro Ala Ser Glu Asn Gly Thr Leu Arg Thr
            100                 105                 110

Asp Tyr Ser Ser Thr Ala Glu Ile Gln Gln Glu Thr Asn Lys Val Ile
        115                 120                 125

Ala Ala Gln Ala Ser Val Lys Ala Ala Val Gln Val Thr Gln Gln
    130                 135                 140

Thr Ala Gly Glu Ser Tyr Gly Tyr Val Val Asn Gly Phe Ser Thr Lys
145                 150                 155                 160

Val Arg Val Val Asp Ile Pro Lys Leu Lys Gln Ile Ala Gly Val Lys
                165                 170                 175

Thr Val Thr Leu Ala Lys Val Tyr Tyr Pro Thr Asp Ala Lys Ala Asn
            180                 185                 190

Ser Met Ala Asn Val Gln Ala Val Trp Ser Asn Tyr Lys Tyr Lys Gly
        195                 200                 205

Glu Gly Thr Val Val Ser Val Ile Asp Ser Gly Ile Asp Pro Thr His
    210                 215                 220

Lys Asp Met Arg Leu Ser Asp Asp Lys Asp Val Lys Leu Thr Lys Ser
225                 230                 235                 240

Asp Val Glu Lys Phe Thr Asp Val Lys His Gly Arg Tyr Phe Asn
                245                 250                 255
```

-continued

```
Ser Lys Val Pro Tyr Gly Phe Asn Tyr Ala Asp Asn Asp Thr Ile
            260                 265                 270

Thr Asp Asp Lys Val Asp Glu Gln His Gly Met His Val Ala Gly Ile
        275                 280                 285

Ile Gly Ala Asn Gly Thr Gly Asp Asp Pro Ala Lys Ser Val Val Gly
        290                 295                 300

Val Ala Pro Glu Ala Gln Leu Leu Ala Met Lys Val Phe Thr Asn Ser
305                 310                 315                 320

Asp Thr Ser Ala Thr Thr Gly Ser Asp Thr Leu Val Ser Ala Ile Glu
            325                 330                 335

Asp Ser Ala Lys Ile Gly Ala Asp Val Leu Asn Met Ser Leu Gly Ser
            340                 345                 350

Asp Ser Gly Asn Gln Thr Leu Glu Asp Pro Glu Ile Ala Ala Val Gln
            355                 360                 365

Asn Ala Asn Glu Ser Gly Thr Ala Ala Val Ile Ser Ala Gly Asn Ser
    370                 375                 380

Gly Thr Ser Gly Ser Ala Thr Glu Gly Val Asn Lys Asp Tyr Tyr Gly
385                 390                 395                 400

Leu Gln Asp Asn Glu Met Val Gly Thr Pro Gly Thr Ser Arg Gly Ala
                405                 410                 415

Thr Thr Val Ala Ser Ala Glu Asn Thr Asp Val Ile Thr Gln Ala Val
            420                 425                 430

Thr Ile Thr Asp Gly Thr Gly Leu Gln Leu Gly Pro Glu Thr Ile Gln
        435                 440                 445

Leu Ser Ser Asn Asp Phe Thr Gly Ser Phe Asp Gln Lys Lys Phe Tyr
    450                 455                 460

Val Val Lys Asp Ala Ser Gly Asn Leu Ser Lys Gly Lys Val Ala Asp
465                 470                 475                 480

Tyr Thr Ala Asp Ala Lys Gly Lys Ile Ala Ile Val Lys Arg Gly Glu
                485                 490                 495

Leu Thr Phe Asp Asp Lys Gln Lys Tyr Ala Gln Ala Ala Gly Ala Ala
            500                 505                 510

Gly Leu Ile Ile Val Asn Asn Asp Gly Thr Ala Thr Pro Val Thr Ser
        515                 520                 525

Met Ala Leu Thr Thr Thr Phe Pro Thr Phe Gly Leu Ser Ser Val Thr
530                 535                 540

Gly Gln Lys Leu Val Asp Trp Val Thr Ala His Pro Asp Asp Ser Leu
545                 550                 555                 560

Gly Val Lys Ile Ala Leu Thr Leu Val Pro Asn Gln Lys Tyr Thr Glu
                565                 570                 575

Asp Lys Met Ser Asp Phe Thr Ser Tyr Gly Pro Val Ser Asn Leu Ser
            580                 585                 590

Phe Lys Pro Asp Ile Thr Ala Pro Gly Gly Asn Ile Trp Ser Thr Gln
        595                 600                 605

Asn Asn Asn Gly Tyr Thr Asn Met Ser Gly Thr Ser Met Ala Ser Pro
    610                 615                 620

Phe Ile Ala Gly Ser Gln Ala Leu Leu Lys Gln Ala Leu Asn Asn Lys
625                 630                 635                 640

Asn Asn Pro Phe Tyr Ala Tyr Tyr Lys Gln Leu Lys Gly Thr Ala Leu
                645                 650                 655

Thr Asp Phe Leu Lys Thr Val Glu Met Asn Thr Ala Gln Pro Ile Asn
            660                 665                 670

Asp Ile Asn Tyr Asn Asn Val Ile Val Ser Pro Arg Arg Gln Gly Ala
        675                 680                 685
```

```
Gly Leu Val Asp Val Lys Ala Ala Ile Asp Ala Leu Glu Lys Asn Pro
    690                 695                 700

Ser Thr Val Val Ala Glu Asn Gly Tyr Pro Ala Val Glu Leu Lys Asp
705                 710                 715                 720

Phe Thr Ser Thr Asp Lys Thr Phe Lys Leu Thr Phe Thr Asn Arg Thr
                725                 730                 735

Thr His Glu Leu Thr Tyr Gln Met Asp Ser Asn Thr Asp Thr Asn Ala
            740                 745                 750

Val Tyr Thr Ser Ala Thr Asp Pro Asn Ser Gly Val Leu Tyr Asp Lys
        755                 760                 765

Lys Ile Asp Gly Ala Ala Ile Lys Ala Gly Ser Asn Ile Thr Val Pro
    770                 775                 780

Ala Gly Lys Thr Ala Gln Ile Glu Phe Thr Leu Ser Leu Pro Lys Ser
785                 790                 795                 800

Phe Asp Gln Gln Gln Phe Val Glu Gly Phe Leu Asn Phe Lys Gly Ser
                805                 810                 815

Asp Gly Ser Arg Leu Asn Leu Pro Tyr Met Gly Phe Phe Gly Asp Trp
            820                 825                 830

Asn Asp Gly Lys Ile Val Asp Ser Leu Asn Gly Ile Thr Tyr Ser Pro
        835                 840                 845

Ala Gly Gly Asn Phe Gly Thr Val Pro Leu Leu Thr Asn Lys Asn Thr
    850                 855                 860

Gly Thr Gln Tyr Tyr Gly Gly Met Val Thr Asp Ala Asp Gly Asn Gln
865                 870                 875                 880

Thr Val Asp Asp Gln Ala Ile Ala Phe Ser Asp Lys Asn Ala Leu
                885                 890                 895

Tyr Asn Asp Ile Ser Met Lys Tyr Tyr Leu Leu Arg Asn Ile Ser Asn
            900                 905                 910

Val Gln Val Asp Ile Leu Asp Gly Gln Gly Asn Lys Val Thr Thr Leu
        915                 920                 925

Ser Ser Ser Thr Asn Leu Thr Lys Thr Tyr Tyr Asn Ala His Ser Gln
    930                 935                 940

Gln Tyr Ile Tyr Tyr His Ala Pro Ala Trp Asp Gly Thr Tyr Tyr Asp
945                 950                 955                 960

Gln Arg Asp Gly Asn Ile Lys Thr Ala Asp Asp Gly Ser Tyr Thr Tyr
                965                 970                 975

Arg Ile Ser Gly Val Pro Glu Gly Gly Asp Lys Arg Gln Val Phe Asp
            980                 985                 990

Val Pro Phe Lys Leu Asp Ser Lys Ala Pro Thr Val Arg His Val Ala
        995                 1000                1005

Leu Ser Ala Lys Thr Lys Asn Gly Lys Thr Gln Tyr Tyr Leu Thr Ala
    1010                1015                1020

Glu Val Lys Asp Asp Leu Ser Gly Leu Asp Ala Thr Lys Ser Val Lys
1025                1030                1035                1040

Thr Ala Ile Asn Glu Val Thr Asn Leu Asp Ala Thr Phe Thr Asp Ala
                1045                1050                1055

Gly Thr Thr Ala Asp Gly Tyr Thr Lys Ile Glu Thr Pro Leu Ser Asp
            1060                1065                1070

Glu Gln Ala Gln Ala Leu Gly Asn Gly Asp Asn Ser Ala Glu Leu Tyr
        1075                1080                1085

Leu Thr Asp Asn Ala Ser Asn Ala Thr Asp Gln Asp Ala Ser Val Gln
    1090                1095                1100

Lys Pro Gly Ser Thr Ser Phe Asp Leu Ile Val Asn Gly Ser Gly Ile
```

```
                    1105              1110              1115              1120
Pro Asp Lys Ile Ser Ser Thr Thr Thr Gly Tyr Glu Ala Asn Thr Gln
                1125              1130              1135
Gly Gly Gly Thr Tyr Thr Phe Ser Gly Thr Tyr Pro Ala Ala Val Asp
            1140              1145              1150
Gly Thr Tyr Thr Asp Ala Gln Gly Lys Lys His Asp Leu Asn Thr Thr
        1155              1160              1165
Tyr Asp Ala Ala Thr Asn Ser Phe Thr Ala Ser Met Pro Val Thr Asn
    1170              1175              1180
Ala Asp Tyr Ala Ala Gln Val Asp Leu Tyr Ala Asp Lys Ala His Thr
1185              1190              1195              1200
Gln Leu Leu Lys His Phe Asp Thr Lys Val Arg Leu Thr Ala Pro Thr
                1205              1210              1215
Phe Thr Asp Leu Lys Phe Asn Asn Gly Ser Asp Gln Thr Ser Glu Ala
            1220              1225              1230
Thr Ile Lys Val Thr Gly Thr Val Ser Ala Asp Thr Lys Thr Val Asn
        1235              1240              1245
Val Gly Asp Thr Val Ala Ala Leu Asp Ala Gln His His Phe Ser Val
    1250              1255              1260
Asp Val Pro Val Asn Tyr Gly Asp Asn Thr Ile Lys Val Ile Ala Thr
1265              1270              1275              1280
Asp Glu Asp Gly Asn Thr Thr Thr Glu Gln Lys Thr Ile Thr Ser Ser
                1285              1290              1295
Tyr Asp Pro Asp Met Leu Lys Asn Pro Val Thr Phe Asp Gln Gly Val
            1300              1305              1310
Thr Phe Gly Ser Asn Glu Phe Asn Ala Thr Ser Ala Lys Phe Tyr Asp
        1315              1320              1325
Pro Lys Thr Gly Ile Ala Thr Ile Thr Gly Lys Val Lys His Pro Thr
    1330              1335              1340
Thr Thr Leu Gln Val Asp Gly Lys Gln Ile Pro Ile Lys Asp Asp Leu
1345              1350              1355              1360
Thr Phe Ser Phe Thr Leu Asp Leu Gly Thr Leu Gly Gln Lys Pro Phe
                1365              1370              1375
Gly Val Val Val Gly Asp Thr Thr Gln Asn Lys Thr Phe Gln Glu Ala
            1380              1385              1390
Leu Thr Phe Ile Leu Asp Ala Val Ala Pro Thr Leu Ser Leu Asp Ser
        1395              1400              1405
Ser Thr Asp Ala Pro Val Tyr Thr Asn Asp Pro Asn Phe Gln Ile Thr
    1410              1415              1420
Gly Thr Ala Thr Asp Asn Ala Gln Tyr Leu Ser Leu Ser Ile Asn Gly
1425              1430              1435              1440
Ser Ser Val Ala Ser Gln Tyr Ala Asp Ile Asn Ile Asn Ser Gly Lys
                1445              1450              1455
Pro Gly His Met Ala Ile Asp Gln Pro Val Lys Leu Leu Glu Gly Lys
            1460              1465              1470
Asn Val Leu Thr Val Ala Val Thr Asp Ser Glu Asp Asn Thr Thr Thr
        1475              1480              1485
Lys Asn Ile Thr Val Tyr Tyr Glu Pro Lys Lys Thr Leu Ala Ala Pro
    1490              1495              1500
Thr Val Thr Pro Ser Thr Thr Glu Pro Ala Gln Val Thr Leu Thr
1505              1510              1515              1520
Ala Asn Ala Ala Ala Thr Gly Glu Thr Val Gln Tyr Ser Ala Asp Gly
                1525              1530              1535
```

```
Gly Lys Thr Tyr Gln Asp Val Pro Ala Ala Gly Val Thr Ile Thr Ala
        1540                1545                1550

Asn Gly Thr Phe Lys Phe Lys Ser Thr Asp Leu Tyr Gly Asn Glu Ser
    1555                1560                1565

Pro Ala Val Asp Tyr Val Val Thr Asn Ile Lys Ala Asp Asp Pro Ala
    1570                1575                1580

Gln Leu Gln Ala Ala Lys Gln Ala Leu Thr Asn Leu Ile Ala Ser Ala
1585                1590                1595                1600

Lys Thr Leu Ser Ala Ser Gly Lys Tyr Asp Asp Ala Thr Thr Ala
        1605                1610                1615

Leu Ala Ala Ala Thr Gln Lys Ala Gln Thr Ala Leu Asp Gln Thr Asn
        1620                1625                1630

Ala Ser Val Asp Ser Leu Thr Gly Ala Asn Arg Asp Leu Gln Thr Ala
        1635                1640                1645

Ile Asn Gln Leu Ala Ala Lys Leu Pro Ala Asp Lys Lys Thr Ser Leu
    1650                1655                1660

Leu Asn Gln Leu Gln Ser Val Lys Asp Ala Leu Gly Thr Asp Leu Gly
1665                1670                1675                1680

Asn Gln Thr Asp Pro Ser Thr Gly Lys Thr Phe Thr Ala Ala Leu Asp
        1685                1690                1695

Asp Leu Val Ala Gln Ala Gln Ala Gly Thr Gln Thr Asp Asp Gln Leu
        1700                1705                1710

Gln Ala Thr Leu Ala Lys Ile Leu Asp Glu Val Leu Ala Lys Leu Ala
        1715                1720                1725

Glu Gly Ile Lys Ala Ala Thr Pro Ala Glu Val Gly Asn Ala Lys Asp
    1730                1735                1740

Ala Ala Thr Gly Lys Thr Trp Tyr Ala Asp Ile Ala Asp Thr Leu Thr
1745                1750                1755                1760

Ser Gly Gln Ala Ser Ala Asp Ala Ser Asp Lys Leu Ala His Leu Gln
        1765                1770                1775

Ala Leu Gln Ser Leu Lys Thr Lys Val Ala Ala Ala Val Glu Ala Asp
        1780                1785                1790

Lys Thr Val Gly Lys Gly Asp Asp Thr Thr Gly Thr Ser Asp Lys Gly
        1795                1800                1805

Ser Gly Gln Gly Thr Pro Ala Pro Ala Thr Gly Asp Thr Gly Lys Asp
    1810                1815                1820

Lys Gly Asp Glu Gly Ser Gln Pro Ser Ser Gly Gly Asn Ile Pro Thr
1825                1830                1835                1840

Asn Pro Ala Thr Thr Thr Ser Thr Ser Thr Asp Asp Thr Asp Arg
        1845                1850                1855

Asn Gly Gln His Thr Thr Gly Lys Gly Ala Leu Pro Lys Thr Gly Glu
        1860                1865                1870

Thr Thr Glu Arg Pro Ala Phe Gly Phe Leu Gly Val Ile Val Val Ile
        1875                1880                1885

Leu Met Gly Val Leu Gly Leu Lys Arg Lys Gln Arg Glu Glu
        1890                1895                1900

<210> SEQ ID NO 3
<211> LENGTH: 299
<212> TYPE: PRT
<213> ORGANISM: Lactococcus lactis

<400> SEQUENCE: 3

Met Lys Lys Lys Met Arg Leu Lys Val Leu Leu Ala Ser Thr Ala Thr
 1               5                   10                  15
```

```
Ala Leu Leu Leu Leu Ser Gly Cys Gln Ser Asn Gln Thr Asp Gln Thr
            20                  25                  30

Val Ala Thr Tyr Ser Gly Gly Lys Val Thr Glu Ser Phe Tyr Lys
        35                  40                  45

Glu Leu Lys Gln Ser Pro Thr Thr Lys Thr Met Leu Ala Asn Met Leu
 50                  55                  60

Ile Tyr Arg Ala Leu Asn His Ala Tyr Gly Lys Ser Val Ser Thr Lys
 65                  70                  75                  80

Thr Val Asn Asp Ala Tyr Asp Ser Tyr Lys Gln Gln Tyr Gly Glu Asn
                 85                  90                  95

Phe Asp Ala Phe Leu Ser Gln Asn Gly Phe Ser Arg Ser Ser Phe Lys
                100                 105                 110

Glu Ser Leu Arg Thr Asn Phe Leu Ser Glu Val Ala Leu Lys Lys Leu
                115                 120                 125

Lys Lys Val Ser Glu Ser Gln Leu Lys Ala Ala Trp Lys Thr Tyr Gln
130                 135                 140

Pro Lys Val Thr Val Gln His Ile Leu Thr Ser Asp Glu Asp Thr Ala
145                 150                 155                 160

Lys Gln Val Ile Ser Asp Leu Ala Ser Gly Lys Asp Phe Ala Met Leu
                165                 170                 175

Ala Lys Thr Asp Ser Ile Asp Thr Ala Thr Lys Asp Asn Gly Gly Lys
                180                 185                 190

Ile Ser Phe Glu Leu Asn Asn Lys Thr Leu Asp Ala Thr Phe Lys Asp
                195                 200                 205

Ala Ala Tyr Lys Leu Lys Asn Gly Asp Tyr Thr Gln Thr Pro Val Lys
210                 215                 220

Val Thr Asp Gly Tyr Glu Val Ile Lys Met Ile Asn His Pro Ala Lys
225                 230                 235                 240

Gly Thr Phe Thr Ser Ser Lys Lys Val Leu Thr Ala Ser Val Tyr Ala
                245                 250                 255

Lys Trp Ser Arg Asp Ser Ser Ile Met Gln Arg Val Ile Ser Gln Val
                260                 265                 270

Leu Lys Asn Gln His Val Thr Ile Lys Asp Lys Asp Leu Ala Asp Ala
                275                 280                 285

Leu Asp Ser Tyr Lys Lys Leu Ala Thr Thr Asn
290                 295

<210> SEQ ID NO 4
<211> LENGTH: 1243
<212> TYPE: PRT
<213> ORGANISM: Lactococcus lactis

<400> SEQUENCE: 4

Met Lys Lys Thr Leu Arg Asp Gln Leu Leu Gly Val Ser Lys Ala His
 1               5                  10                  15

Leu Asn Trp Lys Asn Lys Thr Lys Val Phe Ile Tyr Gly Thr Ala Ile
            20                  25                  30

Leu Leu Met Val Ala Pro Asn Leu Ala Ser Ser Val Ser Arg Ala Ser
        35                  40                  45

Ala Asp Glu Glu Gly Asn Ala Pro Lys Val Thr Gln Ala Gly Glu Arg
     50                  55                  60

Ser Gly Lys Leu Ala Leu Asn Ile Ser His Ser Ala Leu Asp Gln Ala
 65                  70                  75                  80

Ile Ser Asp Ala Lys Ala Ala Gly Leu Ser Leu Lys Glu Gly Ala Ile
                 85                  90                  95
```

```
Gln Asp Lys Gly Asn Ala Gln Gly Thr Asp Ala Ile Thr Lys Leu Gln
            100                 105                 110
Lys Ala Ile Ser Asp Asp Tyr Ala Ser Gln Val Ser Thr Ile Lys Lys
            115                 120                 125
Gln Thr Ser Asp Tyr Lys Thr Ala Leu Asp Ala Tyr Asn Lys Ala Glu
        130                 135                 140
Ala Asp Tyr Lys Lys Gln Leu Asp Asp Ile Gln Asn Gly Ile Asp Asn
145                 150                 155                 160
Asn Thr Pro Gly Ser Pro Ala Val Ala Lys Gly Gln Gly Leu Thr Phe
                165                 170                 175
Arg Ala Gly Gln Asn Pro Lys Ala Thr Val Glu Ser Val Lys Phe Ser
            180                 185                 190
Gly Ser Gly Asp Gly Ala Leu Leu Lys Ser Lys Val Leu Gly Asp Gly
        195                 200                 205
Met Thr Gly Leu Ser Lys Val Thr Ser Ser Asp Val Val Ser Gln Pro
    210                 215                 220
Asp Phe Tyr Asp Leu Gly Gly Thr Thr Ser Leu Phe Gly Leu Phe Leu
225                 230                 235                 240
Asp Ala Gly Gln Ser Val Thr Ile Thr Tyr Lys Asp Leu Lys Asn Phe
                245                 250                 255
Ser Leu Asn Gly Thr Ser Val Ile Gln Met Lys Val Thr Tyr Lys Asn
            260                 265                 270
Val Thr Asn Ala Arg Met Gly Ile Met Val Ser Arg Asp Pro Gly Asn
        275                 280                 285
Gln Phe Gln Phe Gly Val Glu Thr Asn Gly Arg Ile Phe Val Asn Gln
    290                 295                 300
Pro Lys Ala Leu Gln Glu Ser Leu Glu Phe His Asp Gly Ser Asn Lys
305                 310                 315                 320
Leu Met Thr Phe Lys Thr Val Asp Ser Ser Ala Gln Phe Met Ala
                325                 330                 335
Gly Ser Leu Asn Tyr Ser Lys Ser Lys Thr Pro Glu Gly Gly Leu Pro
            340                 345                 350
Pro Thr Ser Asp Gly Tyr Asn Gln His Glu Ser Val Ser Phe Asp Asn
        355                 360                 365
Thr Leu Val Val Gly Ser Tyr Phe Pro Ser Ser Gly Val His Lys Val
    370                 375                 380
Ser Gly Arg Pro Thr Ser Gly Ala Asn Ala Thr Gly Asp Ser Trp Ser
385                 390                 395                 400
Ser Asn Pro Pro Ser Thr Asn Glu Thr Trp Ser Ala Thr Ala Tyr Ile
                405                 410                 415
Asp Tyr Lys Ala Ile Gly Pro Ser Leu Asp Val Thr Glu Trp Asp Val
            420                 425                 430
Gly Thr Lys Asn Ser Trp Tyr Gly Ala Met Asn Leu Ile Pro Lys Asp
        435                 440                 445
Gly Gln Thr Ser Ile Ser Val Thr Trp Gly Thr Thr Asp Ala Asn Met
    450                 455                 460
Trp Ala Leu Leu Asn Gly Gln Leu Pro Asn Lys Ile Pro Thr Pro Glu
465                 470                 475                 480
Pro Pro Ile Pro Pro Val Lys Pro Thr Ala Thr Tyr Tyr Tyr Asp Gln
                485                 490                 495
Ala Thr Phe Gln Thr Asp Asn Thr Lys Ala Val Thr Gln Thr Asp Gly
            500                 505                 510
Thr Asp Leu Asn Gly Ala Leu Val Asn Lys Gln Glu Thr Glu Asn Trp
        515                 520                 525
```

```
Val Leu Ser Asn Glu Val Leu Pro Ala Gly His Glu Val Ile Lys Ser
        530                 535                 540
Tyr Val Met Thr Asp Pro Leu Pro Glu Gly Phe Lys Leu Asp Leu Glu
545                 550                 555                 560
Gln Ser Lys Thr Leu Ser Pro Asp Tyr Asp Leu Thr Phe Asp Glu Lys
                565                 570                 575
Thr Asn Thr Val Thr Leu Thr Ala Tyr Lys Ala Thr Leu Glu Ala Met
            580                 585                 590
Asn Lys Asp Leu Asn Gln Ala Tyr Gln Val Pro Lys Glu Thr Leu Gln
            595                 600                 605
Gly Gln Val Thr Lys Asp Gly Ser Ser Phe Lys Asn Asp Leu Glu Thr
        610                 615                 620
Leu Ile Asn Asp Tyr Thr Val Asn Ser Asn Glu Val Glu Val His Thr
625                 630                 635                 640
Pro Asp Pro Lys Pro Glu Lys Ser Asn Glu Asn Ala Ser Gly Thr Thr
                645                 650                 655
Ile Asn Gly Gln Gly Ile Asp Val Asn Ala Thr Asn Tyr Tyr Lys Leu
            660                 665                 670
Leu Trp Asp Leu Ser Gly Tyr Lys Gly Ile Ala Ser Ser Lys Glu Asp
            675                 680                 685
Ile Val Arg Gly Phe Tyr Phe Val Asp Ala Ala Pro Asp Val Val Asp
        690                 695                 700
Val Asp Leu Lys Asn Ile Ser Tyr Lys Asp Ser Gln Gly Lys Glu Val
705                 710                 715                 720
Lys Gly Ile Thr Ala Lys Val Tyr Ser Ser Val Lys Asp Ala Pro Ala
                725                 730                 735
Glu Val Gln Lys Val Leu Ala Asp Ala Lys Ile Ala Pro Lys Gly Gln
            740                 745                 750
Phe Val Phe Tyr Ser Val Asp Asp Pro Gln Thr Phe Tyr Thr Asn Tyr
            755                 760                 765
Val Gln Thr Gly Asn Asn Val Glu Ile Thr Gln Pro Met Thr Phe Lys
        770                 775                 780
Glu Gly Ala Ser Gly Ala Tyr Gln Asn Thr Asp Tyr Gln Ile Asp Phe
785                 790                 795                 800
Gly Asn Ser Tyr Glu Gly Asp Thr Val Lys Asn Asn Ile Val Pro Pro
                805                 810                 815
Lys Val Val Lys Gln Val Ser Val Asp Gly Gly Lys Thr Trp His Asp
            820                 825                 830
Ser Lys Asp Leu Pro Asp Thr Asp Ser Asn Tyr Asp Tyr Lys Leu Asp
        835                 840                 845
Phe Asn Phe Thr Ala Asn Gly Asp Tyr Thr Lys Ile Leu Leu Gly Asp
850                 855                 860
Asn Phe Glu Ser Ser Gln Trp Thr Asp Leu Ala Lys Ala Lys Val Thr
865                 870                 875                 880
Asp Lys Asp Gly Asn Asp Ile Ala Gly Gln Phe Lys Val Leu Asn Ala
                885                 890                 895
Ser Gly Lys Asp Val Thr Lys Asp Phe Asn Asn His Val Phe Gln Lys
            900                 905                 910
Asp Gly Lys Lys Glu Val Leu Gln Ile Ile Phe Thr Pro Asp Lys Ile
            915                 920                 925
Ser Asp Ile Thr Ser Leu Ala Ser Asn Ser Asp Pro Asp Arg Leu Ile
        930                 935                 940
Thr Leu Thr Met Ser Phe Lys Asp Val Thr Leu Lys Gly Ala Thr Gly
```

-continued

```
                945                 950                 955                 960
Ala Glu Leu Ala Asn Tyr Leu Asp Lys Glu Gly Lys Ile Val Ala Pro
                    965                 970                 975
Asn Ile Gly Gln Leu Asp Thr Thr Ser Arg Thr Val Thr Gly Asp Asn
                    980                 985                 990
Thr Lys Asp Lys Ile Thr Lys Ser Asn Val Thr Lys Val Ile Pro Pro
                    995                1000                1005
Gln Leu Thr Pro Met Ile Asn Lys Tyr Val Tyr Glu Thr Gly Val Gly
               1010                1015                1020
Ser Ser Ile Asn Leu Tyr Asp Lys Gly Leu Thr Leu Pro Ser Tyr Leu
1025                1030                1035                1040
Ser Lys Leu Ala Gln Phe Thr Ser Leu Asn Leu Asn Lys Asp Glu Lys
                    1045                1050                1055
Val Lys Val Gly Glu Thr Val His Trp Leu Ile Ala Thr Gln Ser Gly
                    1060                1065                1070
Asn Lys Ser Leu Met Thr Asn Val Val Asp Thr Leu Pro Lys Glu Leu
                    1075                1080                1085
Ser Phe Ala Glu Asn Met Asn Ala Lys Val Phe Val Leu Lys Asn Asp
                    1090                1095                1100
Gly Lys Leu Gly Asp Glu Val Thr Asn Asp Trp Lys Ile Glu Asn Lys
1105                1110                1115                1120
Gly Gln Thr Leu Thr Ala Thr Pro Asn Asp Pro Thr Lys Tyr Phe Phe
                    1125                1130                1135
Val Gly Ser Ser Thr Asp Ser Arg Val Val Ile Thr Leu Asp Thr Thr
                    1140                1145                1150
Val Asn Glu Glu Ala Lys Thr Gly Thr Phe Thr Asn Ile Ala Thr Ile
                    1155                1160                1165
Asn Thr Lys Asp Gly Gly His Lys Glu Asp Lys Ala Asn Val His Thr
                    1170                1175                1180
Lys Glu Lys Pro Glu Thr Val Ile Glu Lys Ile Thr Gly Ser Leu Pro
1185                1190                1195                1200
Lys Thr Gly Glu Gly Lys Ala Ala Leu Ala Ile Ser Ile Phe Gly Ala
                    1205                1210                1215
Ala Leu Leu Gly Leu Ala Ala Tyr Leu Lys Arg Asn Trp Ile Val Ser
                    1220                1225                1230
Thr Tyr Arg Lys Thr Val Arg Lys Ile Arg Lys
                    1235                1240

<210> SEQ ID NO 5
<211> LENGTH: 1575
<212> TYPE: PRT
<213> ORGANISM: Streptococcus gordonii

<400> SEQUENCE: 5

Met Asn Lys Arg Lys Glu Val Phe Gly Phe Arg Lys Ser Lys Val Ala
  1               5                  10                  15
Lys Thr Leu Cys Gly Ala Val Leu Gly Ala Ala Leu Ile Ala Ile Ala
                 20                  25                  30
Asp Gln Gln Val Leu Ala Asp Glu Val Thr Glu Thr Asn Ser Thr Ala
             35                  40                  45
Asn Val Ala Val Thr Thr Thr Gly Asn Pro Ala Thr Asn Leu Pro Glu
         50                  55                  60
Ala Gln Gly Glu Ala Thr Glu Ala Ala Ser Gln Ser Gln Ala Gln Ala
 65                  70                  75                  80
Gly Ser Lys Glu Gly Ala Leu Pro Val Glu Val Ser Ala Asp Asp Leu
```

```
                   85                  90                  95
Asn Gln Ala Val Thr Asp Ala Lys Ala Gly Val Asn Val Gln
                100                 105                 110
Asp Gln Thr Ser Asp Lys Gly Thr Ala Thr Ala Ala Glu Asn Ala
            115                 120                 125
Gln Lys Gln Ala Glu Ile Lys Ser Asp Tyr Ala Lys Gln Ala Glu Glu
            130                 135                 140
Ile Lys Lys Thr Thr Glu Ala Tyr Lys Lys Val Glu Ala His Gln
145                 150                 155                 160
Ala Glu Thr Asp Lys Ile Asn Ala Glu Asn Lys Ala Ala Glu Asp Lys
                165                 170                 175
Tyr Gln Glu Asp Leu Lys Ala His Gln Ala Glu Val Glu Lys Ile Asn
                180                 185                 190
Thr Ala Asn Ala Thr Ala Lys Ala Glu Tyr Glu Ala Lys Leu Ala Gln
                195                 200                 205
Tyr Gln Lys Asp Leu Ala Ala Val Gln Lys Ala Asn Glu Asp Ser Gln
                210                 215                 220
Leu Asp Tyr Gln Asn Lys Leu Ser Ala Tyr Gln Ala Glu Leu Ala Arg
225                 230                 235                 240
Val Gln Lys Ala Asn Ala Glu Ala Lys Glu Ala Tyr Glu Lys Ala Val
                245                 250                 255
Lys Glu Asn Thr Ala Lys Asn Ala Ala Leu Gln Ala Glu Asn Glu Ala
                260                 265                 270
Ile Lys Gln Arg Asn Glu Thr Ala Lys Ala Asn Tyr Asp Ala Ala Met
                275                 280                 285
Lys Gln Tyr Glu Ala Asp Leu Ala Ala Ile Lys Lys Ala Lys Glu Asp
                290                 295                 300
Asn Asp Ala Asp Tyr Gln Ala Lys Leu Ala Ala Tyr Gln Ala Glu Leu
305                 310                 315                 320
Ala Arg Val Gln Lys Ala Asn Ala Asp Ala Lys Ala Ala Tyr Glu Lys
                325                 330                 335
Ala Val Glu Glu Asn Thr Ala Lys Asn Thr Ala Ile Gln Ala Glu Asn
                340                 345                 350
Glu Ala Ile Lys Gln Arg Asn Ala Ala Ala Lys Ala Thr Tyr Glu Ala
                355                 360                 365
Ala Leu Lys Gln Tyr Glu Ala Asp Leu Ala Ala Ala Lys Lys Ala Asn
                370                 375                 380
Glu Asp Ser Asp Ala Asp Tyr Gln Ala Lys Leu Ala Ala Tyr Gln Thr
385                 390                 395                 400
Glu Leu Ala Arg Val Gln Lys Ala Asn Ala Asp Ala Lys Ala Ala Tyr
                405                 410                 415
Glu Lys Ala Val Glu Asp Asn Lys Ala Lys Asn Ala Ala Leu Gln Ala
                420                 425                 430
Glu Asn Glu Glu Ile Lys Gln Arg Asn Ala Ala Ala Lys Thr Asp Tyr
                435                 440                 445
Glu Ala Lys Leu Ala Lys Tyr Glu Ala Asp Leu Ala Lys Tyr Lys Lys
                450                 455                 460
Glu Leu Ala Glu Tyr Pro Ala Lys Leu Lys Ala Tyr Glu Asp Glu Gln
465                 470                 475                 480
Ala Gln Ile Lys Ala Ala Leu Val Glu Leu Glu Lys Asn Lys Asn Gln
                485                 490                 495
Asp Gly Tyr Leu Ser Lys Pro Ser Ala Gln Ser Leu Val Tyr Asp Ser
                500                 505                 510
```

```
Glu Pro Asn Ala Gln Leu Ser Leu Thr Thr Asn Gly Lys Met Leu Lys
            515                 520                 525

Ala Ser Ala Val Asp Glu Ala Phe Ser His Asp Thr Ala Gln Tyr Ser
    530                 535                 540

Lys Lys Ile Leu Gln Pro Asp Asn Leu Asn Val Ser Tyr Leu Gln Gln
545                 550                 555                 560

Ala Asp Asp Val Thr Ser Ser Met Glu Leu Tyr Gly Asn Phe Gly Asp
                565                 570                 575

Lys Ala Gly Trp Thr Thr Val Gly Asn Asn Thr Glu Val Lys Phe
            580                 585                 590

Ala Ser Val Leu Leu Glu Arg Gly Gln Ser Val Thr Ala Thr Tyr Thr
    595                 600                 605

Asn Leu Glu Lys Ser Tyr Tyr Asn Gly Lys Lys Ile Ser Lys Ala Val
    610                 615                 620

Phe Lys Tyr Ser Leu Asp Ser Asp Ser Lys Phe Lys Asn Val Asp Lys
625                 630                 635                 640

Ala Trp Leu Gly Val Leu Pro Asp Pro Thr Leu Gly Val Phe Ala Ser
                645                 650                 655

Ala Tyr Thr Gly Gln Glu Glu Lys Asp Thr Ser Ile Phe Ile Lys Asn
            660                 665                 670

Glu Phe Thr Phe Tyr Asp Glu Asn Asp Gln Pro Ile Asn Phe Asp Asn
            675                 680                 685

Ala Leu Leu Ser Val Ala Ser Leu Asn Arg Glu Asn Asn Ser Ile Glu
    690                 695                 700

Met Ala Lys Asp Tyr Ser Gly Thr Phe Val Lys Ile Ser Gly Ser Ser
705                 710                 715                 720

Val Gly Glu Lys Asp Gly Lys Ile Tyr Ala Thr Glu Thr Leu Asn Phe
                725                 730                 735

Lys Gln Gly Gln Gly Gly Ser Arg Trp Thr Met Tyr Lys Asn Ser Gln
            740                 745                 750

Pro Gly Ser Gly Trp Asp Ser Ser Asp Ala Pro Asn Ser Trp Tyr Gly
            755                 760                 765

Ala Gly Ala Ile Ser Met Ser Gly Pro Thr Asn His Val Thr Val Gly
    770                 775                 780

Ala Ile Ser Ala Thr Gln Val Val Pro Ser Asp Pro Val Met Ala Val
785                 790                 795                 800

Ala Thr Gly Lys Arg Pro Asn Ile Trp Tyr Ser Leu Asn Gly Lys Ile
                805                 810                 815

Arg Ala Val Asn Val Pro Lys Ile Thr Lys Glu Lys Pro Thr Pro Pro
            820                 825                 830

Val Ala Pro Thr Glu Pro Gln Ala Pro Thr Tyr Glu Val Glu Lys Pro
            835                 840                 845

Leu Glu Pro Ala Pro Val Ala Pro Thr Tyr Glu Asn Glu Pro Thr Pro
    850                 855                 860

Pro Val Lys Thr Pro Asp Gln Pro Glu Pro Ser Lys Pro Glu Glu Pro
865                 870                 875                 880

Thr Tyr Glu Thr Glu Lys Pro Leu Glu Pro Ala Pro Val Pro Thr
                885                 890                 895

Tyr Glu Asn Glu Pro Thr Pro Pro Val Lys Thr Pro Asp Gln Pro Glu
            900                 905                 910

Pro Ser Lys Pro Glu Glu Pro Thr Tyr Glu Thr Glu Lys Pro Leu Glu
            915                 920                 925

Pro Ala Pro Val Ala Pro Thr Tyr Glu Asn Glu Pro Thr Pro Pro Val
    930                 935                 940
```

-continued

Lys Thr Pro Asp Gln Pro Glu Pro Ser Lys Pro Glu Glu Pro Thr Tyr
945                 950                 955                 960

Asp Pro Leu Pro Thr Pro Pro Val Ala Pro Thr Pro Lys Gln Leu Pro
            965                 970                 975

Thr Pro Pro Val Val Pro Thr Val His Phe His Tyr Ser Ser Leu Leu
        980                 985                 990

Ala Gln Pro Gln Ile Asn Lys Glu Ile Lys Asn Glu Asp Gly Val Asp
            995                 1000                1005

Ile Asp Arg Thr Leu Val Ala Lys Gln Ser Ile Val Lys Phe Glu Leu
    1010                1015                1020

Lys Thr Glu Ala Leu Thr Ala Gly Arg Pro Lys Thr Thr Ser Phe Val
1025                1030                1035                1040

Leu Val Asp Pro Leu Pro Thr Gly Tyr Lys Phe Asp Leu Asp Ala Thr
                1045                1050                1055

Lys Ala Ala Ser Thr Gly Phe Asp Thr Thr Tyr Asp Glu Ala Ser His
            1060                1065                1070

Thr Val Thr Phe Lys Ala Thr Asp Glu Thr Leu Ala Thr Tyr Asn Ala
        1075                1080                1085

Asp Leu Thr Lys Pro Val Glu Thr Leu His Pro Thr Val Val Gly Arg
    1090                1095                1100

Val Leu Asn Asp Gly Ala Thr Tyr Ile Asn Asn Phe Thr Leu Thr Val
1105                1110                1115                1120

Asn Asp Ala Tyr Gly Ile Lys Ser Asn Val Val Arg Val Thr Thr Pro
                1125                1130                1135

Gly Lys Pro Asn Asp Pro Asp Asn Pro Asn Asn Tyr Ile Lys Pro
            1140                1145                1150

Thr Lys Val Asn Lys Asn Lys Glu Gly Leu Asn Ile Asp Gly Lys Glu
        1155                1160                1165

Val Leu Ala Gly Ser Thr Asn Tyr Tyr Glu Leu Thr Trp Asp Leu Asp
    1170                1175                1180

Gln Tyr Lys Gly Asp Lys Ser Ser Lys Glu Ala Ile Gln Asn Gly Phe
1185                1190                1195                1200

Tyr Tyr Val Asp Asp Tyr Pro Glu Glu Ala Leu Asp Val Arg Pro Asp
                1205                1210                1215

Leu Val Lys Val Ala Asp Glu Lys Gly Asn Gln Val Ser Gly Val Ser
            1220                1225                1230

Val Gln Gln Tyr Asp Ser Leu Glu Ala Ala Pro Lys Lys Val Gln Asp
        1235                1240                1245

Leu Leu Lys Lys Ala Asn Ile Thr Val Lys Gly Ala Phe Gln Leu Phe
    1250                1255                1260

Ser Ala Asp Asn Pro Glu Glu Phe Tyr Lys Gln Tyr Val Ser Thr Gly
1265                1270                1275                1280

Thr Ser Leu Val Ile Thr Asp Pro Met Thr Val Lys Ser Glu Phe Gly
                1285                1290                1295

Lys Thr Gly Gly Lys Tyr Glu Asn Lys Ala Tyr Gln Ile Asp Phe Gly
            1300                1305                1310

Asn Gly Tyr Ala Thr Glu Val Val Asn Asn Val Pro Lys Ile Thr
        1315                1320                1325

Pro Lys Lys Asp Val Thr Val Ser Leu Asp Pro Thr Ser Glu Asn Leu
    1330                1335                1340

Asp Gly Gln Thr Val Gln Leu Tyr Gln Thr Phe Asn Tyr Arg Leu Ile
1345                1350                1355                1360

Gly Gly Phe Ile Pro Gln Asn His Ser Glu Glu Leu Glu Asp Tyr Ser

```
                                1365              1370                1375
Phe Val Asp Asp Tyr Asp Gln Ala Gly Asp Gln Tyr Thr Gly Asn Tyr
            1380                1385                1390

Lys Thr Phe Ser Ser Leu Asn Leu Thr Met Lys Asp Gly Ser Val Ile
        1395                1400                1405

Lys Ala Gly Thr Asp Leu Thr Ser Gln Thr Thr Ala Glu Thr Asp Ala
    1410                1415                1420

Ala Asn Gly Ile Val Thr Val Arg Ser Lys Glu Asp Ser Leu Gln Lys
1425                1430                1435                1440

Ile Ser Leu Asp Ser Pro Phe Gln Ala Glu Thr Tyr Leu Gln Met Arg
            1445                1450                1455

Arg Ile Ala Ile Gly Thr Phe Glu Asn Thr Tyr Val Asn Thr Val Asn
        1460                1465                1470

Lys Val Ala Tyr Ala Ser Asn Thr Val Arg Thr Thr Thr Pro Ile Pro
    1475                1480                1485

Arg Thr Pro Asp Lys Pro Thr Pro Ile Pro Thr Pro Lys Pro Lys Asp
    1490                1495                1500

Pro Asp Lys Pro Glu Thr Pro Lys Glu Pro Lys Val Pro Ser Pro Lys
1505                1510                1515                1520

Val Glu Asp Pro Ser Ala Pro Ile Pro Val Ser Val Gly Lys Glu Leu
            1525                1530                1535

Thr Thr Leu Pro Lys Thr Gly Thr Asn Asp Ser Ser Tyr Met Pro Tyr
            1540                1545                1550

Leu Gly Leu Ala Ala Leu Val Gly Val Leu Gly Leu Gly Gln Leu Lys
        1555                1560                1565

Arg Lys Glu Asp Glu Ser Asn
    1570                1575

<210> SEQ ID NO 6
<211> LENGTH: 1565
<212> TYPE: PRT
<213> ORGANISM: Streptococcus mutans

<400> SEQUENCE: 6

Met Lys Val Lys Lys Thr Tyr Gly Phe Arg Lys Ser Lys Ile Ser Lys
  1               5                  10                  15

Thr Leu Cys Gly Ala Val Leu Gly Thr Val Ala Ala Val Ser Val Ala
             20                  25                  30

Gly Gln Lys Val Phe Ala Asp Glu Thr Thr Thr Ser Asp Val Asp
         35                  40                  45

Thr Lys Val Val Gly Thr Gln Thr Gly Asn Pro Ala Thr Asn Leu Pro
     50                  55                  60

Glu Ala Gln Gly Ser Ala Ser Lys Glu Ala Gln Ser Gln Thr Lys
 65                  70                  75                  80

Leu Glu Arg Gln Met Val His Thr Ile Glu Val Pro Lys Thr Asp Leu
                 85                  90                  95

Asp Gln Ala Ala Lys Asp Ala Lys Ser Ala Gly Val Asn Val Val Gln
            100                 105                 110

Asp Ala Asp Val Asn Lys Gly Thr Val Lys Thr Pro Glu Glu Ala Val
        115                 120                 125

Gln Lys Glu Thr Glu Ile Lys Glu Asp Tyr Thr Lys Gln Ala Glu Asp
    130                 135                 140

Ile Lys Lys Thr Thr Asp Gln Tyr Lys Ser Asp Val Ala Ala His Glu
145                 150                 155                 160

Ala Glu Val Ala Lys Ile Lys Ala Lys Asn Gln Ala Thr Lys Glu Gln
```

-continued

```
                165                 170                 175
Tyr Glu Lys Asp Met Ala Ala His Lys Ala Glu Val Glu Arg Ile Asn
            180                 185                 190
Ala Ala Asn Ala Ala Ser Lys Thr Ala Tyr Glu Ala Lys Leu Ala Gln
            195                 200                 205
Tyr Gln Ala Asp Leu Ala Ala Val Gln Lys Thr Asn Ala Ala Asn Gln
            210                 215                 220
Ala Ala Tyr Gln Lys Ala Leu Ala Ala Tyr Gln Ala Glu Leu Lys Arg
225                 230                 235                 240
Val Gln Glu Ala Asn Ala Ala Lys Ala Ala Tyr Asp Thr Ala Val
                245                 250                 255
Ala Ala Asn Asn Ala Lys Asn Thr Glu Ile Ala Ala Asn Glu Glu
                260                 265                 270
Ile Arg Lys Arg Asn Ala Thr Ala Lys Ala Glu Tyr Glu Thr Lys Leu
            275                 280                 285
Ala Gln Tyr Gln Ala Glu Leu Lys Arg Val Gln Glu Ala Asn Ala Ala
            290                 295                 300
Asn Glu Ala Asp Tyr Gln Ala Lys Leu Thr Ala Tyr Gln Thr Glu Leu
305                 310                 315                 320
Ala Arg Val Gln Lys Ala Asn Ala Asp Ala Lys Ala Thr Tyr Glu Ala
                325                 330                 335
Ala Val Ala Ala Asn Asn Ala Lys Asn Ala Ala Leu Thr Ala Glu Asn
                340                 345                 350
Thr Ala Ile Lys Gln Arg Asn Glu Asn Ala Lys Ala Thr Tyr Glu Ala
                355                 360                 365
Ala Leu Lys Gln Tyr Glu Ala Asp Leu Ala Ala Val Lys Lys Ala Asn
            370                 375                 380
Ala Ala Asn Glu Ala Asp Tyr Gln Ala Lys Leu Thr Ala Tyr Gln Thr
385                 390                 395                 400
Glu Leu Ala Arg Val Gln Lys Ala Asn Ala Asp Ala Lys Ala Ala Tyr
                405                 410                 415
Glu Ala Ala Val Ala Ala Asn Asn Ala Ala Asn Ala Ala Leu Thr Ala
                420                 425                 430
Glu Asn Thr Ala Ile Lys Lys Arg Asn Ala Asp Ala Lys Ala Asp Tyr
            435                 440                 445
Glu Ala Lys Leu Ala Lys Tyr Gln Ala Asp Leu Ala Lys Tyr Gln Lys
            450                 455                 460
Asp Leu Ala Asp Tyr Pro Val Lys Leu Lys Ala Tyr Glu Asp Glu Gln
465                 470                 475                 480
Thr Ser Ile Lys Ala Ala Leu Ala Glu Leu Glu Lys His Lys Asn Glu
            485                 490                 495
Asp Gly Asn Leu Thr Glu Pro Ser Ala Gln Asn Leu Val Tyr Asp Leu
            500                 505                 510
Glu Pro Asn Ala Asn Leu Ser Leu Thr Thr Asp Gly Lys Phe Leu Lys
            515                 520                 525
Ala Ser Ala Val Asp Asp Ala Phe Ser Lys Ser Thr Ser Lys Ala Lys
            530                 535                 540
Tyr Asp Gln Lys Ile Leu Gln Leu Asp Asp Leu Asp Ile Thr Asn Leu
545                 550                 555                 560
Glu Gln Ser Asn Asp Val Ala Ser Ser Met Glu Leu Tyr Gly Asn Phe
                565                 570                 575
Gly Asp Lys Ala Gly Trp Ser Thr Thr Val Ser Asn Asn Ser Gln Val
            580                 585                 590
```

-continued

```
Lys Trp Gly Ser Val Leu Leu Glu Arg Gly Gln Ser Ala Thr Ala Thr
            595                 600                 605
Tyr Thr Asn Leu Gln Asn Ser Tyr Tyr Asn Gly Lys Lys Ile Ser Lys
        610                 615                 620
Ile Val Tyr Lys Tyr Thr Val Asp Pro Lys Ser Lys Phe Gln Gly Gln
625                 630                 635                 640
Lys Val Trp Leu Gly Ile Phe Thr Asp Pro Thr Leu Gly Val Phe Ala
                645                 650                 655
Ser Ala Tyr Thr Gly Gln Val Glu Lys Asn Thr Ser Ile Phe Ile Lys
            660                 665                 670
Asn Glu Phe Thr Phe Tyr His Glu Asp Glu Lys Pro Ile Asn Phe Asp
        675                 680                 685
Asn Ala Leu Leu Ser Val Thr Ser Leu Asn Arg Glu His Asn Ser Ile
    690                 695                 700
Glu Met Ala Lys Asp Tyr Ser Gly Lys Phe Val Lys Ile Ser Gly Ser
705                 710                 715                 720
Ser Ile Gly Glu Lys Asn Gly Met Ile Tyr Ala Thr Asp Thr Leu Asn
                725                 730                 735
Phe Lys Gln Gly Glu Gly Gly Ser Arg Trp Thr Met Tyr Lys Asn Ser
            740                 745                 750
Gln Ala Gly Ser Gly Trp Asp Ser Ser Asp Ala Pro Asn Ser Trp Tyr
        755                 760                 765
Gly Ala Gly Ala Ile Lys Met Ser Gly Pro Asn Asn His Val Thr Val
    770                 775                 780
Gly Ala Thr Ser Ala Thr Asn Val Met Pro Val Ser Asp Met Pro Val
785                 790                 795                 800
Val Pro Gly Lys Asp Asn Thr Asp Gly Lys Lys Pro Asn Ile Trp Tyr
                805                 810                 815
Ser Leu Asn Gly Lys Ile Arg Ala Val Asn Val Pro Lys Val Thr Lys
            820                 825                 830
Glu Lys Pro Thr Pro Val Lys Pro Thr Ala Pro Thr Lys Pro Thr
        835                 840                 845
Tyr Glu Thr Glu Lys Pro Leu Lys Pro Ala Pro Val Ala Pro Asn Tyr
    850                 855                 860
Glu Lys Glu Pro Thr Pro Pro Thr Arg Thr Pro Asp Gln Ala Glu Pro
865                 870                 875                 880
Asn Lys Pro Thr Pro Pro Thr Tyr Glu Thr Glu Lys Pro Leu Glu Pro
                885                 890                 895
Ala Pro Val Glu Pro Ser Tyr Glu Ala Glu Pro Thr Pro Thr Arg
            900                 905                 910
Thr Pro Asp Gln Ala Glu Pro Asn Lys Pro Thr Pro Pro Thr Tyr Glu
        915                 920                 925
Thr Glu Lys Pro Leu Glu Pro Ala Pro Val Glu Pro Ser Tyr Glu Ala
    930                 935                 940
Glu Pro Thr Pro Pro Thr Pro Thr Pro Asp Gln Pro Glu Pro Asn Lys
945                 950                 955                 960
Pro Val Glu Pro Thr Tyr Glu Val Ile Pro Thr Pro Thr Asp Pro
                965                 970                 975
Val Tyr Gln Asp Leu Pro Thr Pro Ser Asp Pro Thr Val His Phe
            980                 985                 990
His Tyr Phe Lys Leu Ala Val Gln Pro Gln Val Asn Lys Glu Ile Arg
        995                 1000                1005
Asn Asn Asn Asp Ile Asn Ile Asp Arg Thr Leu Val Ala Lys Gln Ser
    1010                1015                1020
```

```
Val Val Lys Phe Gln Leu Lys Thr Ala Asp Leu Pro Ala Gly Arg Asp
1025                1030                1035                1040

Glu Thr Thr Ser Phe Val Leu Val Asp Pro Leu Pro Ser Gly Tyr Gln
            1045                1050                1055

Phe Asn Pro Glu Ala Thr Lys Ala Ala Ser Pro Gly Phe Asp Val Thr
        1060                1065                1070

Tyr Asp Asn Ala Thr Asn Thr Val Thr Phe Lys Ala Thr Ala Ala Thr
    1075                1080                1085

Leu Ala Thr Phe Asn Ala Asp Leu Thr Lys Ser Val Ala Thr Ile Tyr
1090                1095                1100

Pro Thr Val Val Gly Gln Val Leu Asn Asp Gly Ala Thr Tyr Lys Asn
1105                1110                1115                1120

Asn Phe Thr Leu Thr Val Asn Asp Ala Tyr Gly Ile Lys Ser Asn Val
            1125                1130                1135

Val Arg Val Thr Thr Pro Gly Lys Pro Asn Asp Pro Asp Asn Pro Asn
        1140                1145                1150

Asn Asn Tyr Ile Lys Pro Thr Lys Val Asn Lys Asn Glu Asn Gly Val
    1155                1160                1165

Val Ile Asp Gly Lys Thr Val Leu Ala Gly Ser Thr Asn Tyr Tyr Glu
1170                1175                1180

Leu Thr Trp Asp Leu Asp Gln Tyr Lys Asn Asp Arg Ser Ser Ala Asp
1185                1190                1195                1200

Thr Ile Gln Lys Gly Phe Tyr Tyr Val Asp Asp Tyr Pro Glu Glu Ala
            1205                1210                1215

Leu Glu Leu Arg Gln Asp Leu Val Lys Ile Thr Asp Ala Asn Gly Asn
        1220                1225                1230

Glu Val Thr Gly Val Ser Val Asp Asn Tyr Thr Asn Leu Glu Ala Ala
    1235                1240                1245

Pro Gln Glu Ile Arg Asp Val Leu Ser Lys Ala Gly Ile Arg Pro Lys
1250                1255                1260

Gly Ala Phe Gln Ile Phe Arg Ala Asp Asn Pro Arg Glu Phe Tyr Asp
1265                1270                1275                1280

Thr Tyr Val Lys Thr Gly Ile Asp Leu Lys Ile Val Ser Pro Met Val
            1285                1290                1295

Val Lys Lys Gln Met Gly Gln Thr Gly Gly Ser Tyr Glu Asn Gln Ala
        1300                1305                1310

Tyr Gln Ile Asp Phe Gly Asn Gly Tyr Ala Ser Asn Ile Val Ile Asn
    1315                1320                1325

Asn Val Pro Lys Ile Asn Pro Lys Lys Asp Val Thr Leu Thr Leu Asp
1330                1335                1340

Pro Ala Asp Thr Asn Asn Val Asp Gly Gln Thr Ile Pro Leu Asn Thr
1345                1350                1355                1360

Val Phe Asn Tyr Arg Leu Ile Gly Gly Ile Pro Ala Asn His Ser
            1365                1370                1375

Glu Glu Leu Phe Glu Tyr Asn Phe Tyr Asp Asp Tyr Asp Gln Thr Gly
        1380                1385                1390

Asp His Tyr Thr Gly Gln Tyr Lys Val Phe Ala Lys Val Asp Ile Thr
    1395                1400                1405

Leu Lys Asn Gly Val Ile Ile Lys Ser Gly Thr Glu Leu Thr Gln Tyr
1410                1415                1420

Thr Thr Ala Glu Val Asp Thr Thr Lys Gly Ala Ile Thr Ile Lys Phe
1425                1430                1435                1440

Lys Glu Ala Phe Leu Arg Ser Val Ser Ile Asp Ser Ala Phe Gln Ala
```

```
                    1445                1450                1455
Glu Ser Tyr Ile Gln Met Lys Arg Ile Ala Val Gly Thr Phe Glu Asn
            1460                1465                1470

Thr Tyr Ile Asn Thr Val Asn Gly Val Thr Tyr Ser Ser Asn Thr Val
        1475                1480                1485

Lys Thr Thr Thr Pro Glu Asp Pro Ala Asp Pro Thr Asp Pro Gln Asp
    1490                1495                1500

Pro Ser Ser Pro Arg Thr Ser Thr Val Ile Ile Tyr Lys Pro Gln Ser
1505                1510                1515                1520

Thr Ala Tyr Gln Pro Ser Ser Val Gln Glu Thr Leu Pro Asn Thr Gly
            1525                1530                1535

Val Thr Asn Asn Ala Tyr Met Pro Leu Leu Gly Ile Ile Gly Leu Val
        1540                1545                1550

Thr Ser Phe Ser Leu Leu Gly Leu Lys Ala Lys Lys Asp
    1555                1560                1565

<210> SEQ ID NO 7
<211> LENGTH: 325
<212> TYPE: PRT
<213> ORGANISM: Lactococcus lactis

<400> SEQUENCE: 7

Met Glu Lys Gly Leu Leu Val Asp Ile Gly Arg Lys Tyr Trp Ser Ile
1               5                   10                  15

Ala Glu Leu Lys Arg Leu Val Leu Leu Gln Glu His Lys Leu Thr
            20                  25                  30

His Leu Gln Leu His Leu Asn Glu Asn Glu Gly Phe Ala Leu Asn Phe
        35                  40                  45

Thr Asp Ser Pro Val Ser Lys Lys Tyr Ser Glu Asn Met Leu Lys Glu
    50                  55                  60

Leu Lys Glu Phe Ala Lys Thr His Glu Ile Thr Leu Ile Pro Asp Phe
65                  70                  75                  80

Asp Ser Pro Gly His Met Gly Ser Leu Leu Glu Gln Asn Pro Glu Phe
                85                  90                  95

Ala Leu Pro Asp Ser Asn Gln Gln Ala Val Asp Val Thr Asn Pro Ala
            100                 105                 110

Val Ile Asp Trp Ile Met Gly Ile Ile Asp Lys Ile Val Asp Ile Phe
        115                 120                 125

Pro Asp Ser Asp Thr Phe His Ile Gly Ala Asp Glu Phe Ile Asp Phe
    130                 135                 140

Arg Gln Ile Glu Lys Tyr Pro Tyr Leu Val Glu Lys Thr Arg Glu Lys
145                 150                 155                 160

Tyr Gly Asn Lys Ala Ser Gly Leu Glu Phe Tyr Tyr Asp Tyr Val Asn
                165                 170                 175

Gln Leu Thr Glu His Leu Gln Lys Lys Gly Lys Gln Val Arg Ile Trp
            180                 185                 190

Asn Asp Gly Phe Leu Arg Lys Asp Leu Gln Ser Leu Val Pro Leu Asn
        195                 200                 205

Lys Asn Val Glu Val Cys Tyr Trp Thr Asn Trp Asp Lys Gly Met Ala
    210                 215                 220

Glu Val Lys Glu Trp Leu Thr Lys Gly Tyr Thr Leu Ile Asn Phe Cys
225                 230                 235                 240

Asp Asn Asp Leu Tyr Tyr Val Leu Gly Glu Glu Ala Gly Tyr Ser Tyr
                245                 250                 255

Pro Thr Ala Glu Lys Leu Glu Arg Glu Gly Lys Ile Gln Lys Phe Ser
```

```
                        260                 265                 270
Gly Gln Gln Tyr Leu Asn Gln Glu Glu Met Lys Ala Val Arg Gly Thr
            275                 280                 285

Tyr Phe Ser Ile Trp Ala Asp Asn Ala Ala Ala Lys Ser Val Ser Glu
            290                 295                 300

Ile Leu Asp Asp Leu Ser Lys Val Leu Pro Val Phe Met Lys Ile Tyr
305                 310                 315                 320

Gly Gly Asn Asp Glu
            325

<210> SEQ ID NO 8
<211> LENGTH: 355
<212> TYPE: PRT
<213> ORGANISM: Lactobacillus johnsonii

<400> SEQUENCE: 8

Met Phe Val Lys Leu Leu Arg Ser Val Ala Ile Gly Leu Ile Val Gly
 1               5                  10                  15

Ala Ile Leu Leu Val Ala Met Pro Ser Leu Arg Ser Leu Asn Pro Leu
            20                  25                  30

Ser Thr Pro Gln Phe Asp Ser Thr Asp Glu Thr Pro Ala Ser Tyr Asn
            35                  40                  45

Leu Ala Val Arg Arg Ala Ala Pro Ala Val Val Asn Val Tyr Asn Arg
    50                  55                  60

Gly Leu Asn Thr Asn Ser His Asn Gln Leu Glu Ile Arg Thr Leu Gly
65                  70                  75                  80

Ser Gly Val Ile Met Asp Gln Arg Gly Tyr Ile Ile Thr Asn Lys His
                85                  90                  95

Val Ile Asn Asp Ala Asp Gln Ile Ile Val Ala Leu Gln Asp Gly Arg
            100                 105                 110

Val Phe Glu Ala Leu Leu Val Gly Ser Asp Ser Leu Thr Asp Leu Ala
        115                 120                 125

Val Leu Lys Ile Asn Ala Thr Gly Gly Leu Pro Thr Ile Pro Ile Asn
    130                 135                 140

Ala Arg Arg Val Pro His Ile Gly Asp Val Val Leu Ala Ile Gly Asn
145                 150                 155                 160

Pro Tyr Asn Leu Gly Gln Thr Ile Thr Gln Gly Ile Ile Ser Ala Thr
                165                 170                 175

Gly Arg Ile Gly Leu Asn Pro Thr Gly Arg Gln Asn Phe Leu Gln Thr
            180                 185                 190

Asp Ala Ser Ile Asn His Gly Asn Ser Gly Gly Ala Leu Val Asn Ser
        195                 200                 205

Leu Gly Glu Leu Met Gly Ile Asn Thr Leu Ser Phe Asp Lys Ser Asn
    210                 215                 220

Asp Gly Glu Thr Pro Glu Gly Ile Gly Phe Ala Ile Pro Phe Gln Leu
225                 230                 235                 240

Ala Thr Lys Ile Met Asp Lys Leu Ile Arg Asp Gly Arg Val Ile Arg
                245                 250                 255

Gly Tyr Ile Gly Ile Gly Gly Arg Glu Ile Ala Pro Leu His Ala Gln
            260                 265                 270

Gly Gly Gly Ile Asp Gln Leu Gln Gly Ile Val Asn Glu Val Ser
        275                 280                 285

Pro Asp Gly Pro Ala Ala Asn Ala Gly Ile Gln Val Asn Asp Leu Ile
    290                 295                 300

Ile Ser Val Asp Asn Lys Pro Ala Ile Ser Ala Leu Glu Thr Met Asp
```

```
305             310             315             320
Gln Val Ala Glu Ile Arg Pro Gly Ser Val Pro Val Val Met
                325             330             335

Arg Asp Asp Lys Gln Leu Thr Leu Gln Val Thr Ile Gln Glu Tyr Pro
            340             345             350

Ala Thr Asn
        355

<210> SEQ ID NO 9
<211> LENGTH: 423
<212> TYPE: PRT
<213> ORGANISM: Lactobacillus acidophilus

<400> SEQUENCE: 9

Met Ile Leu Gly Asn Met Arg Gly Glu Leu Ser Met Val Glu Asn Gln
  1               5                  10                  15

Asn Asn Asn Gln Arg Pro Arg Lys Asn Ser Asn Ala Lys Ile Ile Thr
                 20                  25                  30

Thr Ala Ala Ile Val Gly Val Gly Gly Leu Ile Gly Gly Gly Val
            35                  40                  45

Ser Tyr Tyr Ala Ala Asp Gln Met Asn Asn Ala Thr Asp Thr Thr
     50                  55                  60

Ala Gln Thr Ser Val Ser Ser Asn Ser Ser Lys Val Ser Glu Lys Ser
 65                  70                  75                  80

Ala Lys Thr Ser Gly Thr Met Thr Thr Ala Tyr Asn Asp Val Lys Gly
                 85                  90                  95

Ala Val Val Ser Val Ile Asn Leu Lys Arg Gln Ser Ser Ser Ser Ser
                100                 105                 110

Ala Asn Ser Leu Tyr Ser Ser Leu Phe Gly Asp Asp Ser Asp Ser Ser
            115                 120                 125

Ser Gly Lys Ser Gly Lys Leu Glu Thr Tyr Ser Glu Gly Ser Ser Val
        130                 135                 140

Val Tyr Met Lys Ser Asn Gly Lys Gly Tyr Ile Val Thr Asn Asn His
145                 150                 155                 160

Val Ile Ser Gly Ser Asp Ala Val Gln Val Gln Leu Ala Asn Gly Lys
                165                 170                 175

Thr Val Ser Ala Lys Val Val Gly Lys Asp Ser Thr Thr Asp Leu Ala
            180                 185                 190

Val Leu Ser Ile Asp Ala Lys Tyr Val Thr Gln Thr Ala Glu Phe Gly
        195                 200                 205

Asp Ser Lys Ser Leu Gln Ala Gly Gln Thr Val Ile Ala Val Gly Ser
    210                 215                 220

Pro Leu Gly Ser Glu Tyr Ala Ser Thr Val Thr Gln Gly Ile Ile Ser
225                 230                 235                 240

Ala Pro Ala Arg Thr Ile Ser Thr Ser Ser Gly Asn Gln Gln Thr Val
                245                 250                 255

Ile Gln Thr Asp Ala Ala Ile Asn Pro Gly Asn Ser Gly Gly Ala Leu
            260                 265                 270

Val Asn Ser Ala Gly Gln Val Ile Gly Ile Asn Ser Met Lys Leu Ala
        275                 280                 285

Gln Ser Ser Asp Gly Thr Ser Val Glu Gly Met Gly Phe Ala Ile Pro
    290                 295                 300

Ser Asn Glu Val Val Thr Ile Val Asn Glu Leu Val Lys Lys Gly Lys
305                 310                 315                 320

Ile Thr Arg Pro Gln Leu Gly Val Arg Val Val Ala Leu Glu Gly Ile
```

```
                        325                 330                 335
Pro Glu Ala Tyr Arg Ser Arg Leu Lys Ile Lys Ser Asn Leu Lys Ser
                340                 345                 350

Gly Ile Tyr Val Ala Ser Ile Asn Lys Asn Ser Ser Ala Ala Asn Ala
            355                 360                 365

Gly Met Lys Ser Gly Asp Val Ile Thr Lys Val Asp Gly Lys Lys Val
        370                 375                 380

Asp Asp Val Ala Ser Leu His Ser Ile Leu Tyr Ser His Lys Val Gly
385                 390                 395                 400

Asp Thr Val Asn Ile Thr Ile Asn Arg Asn Gly Arg Asp Val Asn Leu
                405                 410                 415

Lys Val Lys Leu Glu Gly Asn
            420

<210> SEQ ID NO 10
<211> LENGTH: 411
<212> TYPE: PRT
<213> ORGANISM: Streptococcus thermophilus

<400> SEQUENCE: 10

Met Lys Lys Phe Asn Trp Lys Lys Ile Val Ala Pro Ile Ala Met Leu
  1               5                  10                  15

Ile Ile Gly Leu Leu Gly Gly Leu Leu Gly Ala Phe Ile Leu Leu Thr
             20                  25                  30

Ala Ala Gly Val Ser Phe Thr Asn Thr Thr Asp Thr Gly Val Lys Thr
         35                  40                  45

Ala Lys Thr Val Tyr Thr Asn Ile Thr Asp Thr Thr Lys Ala Val Lys
     50                  55                  60

Lys Val Gln Asn Ala Val Val Ser Val Ile Asn Tyr Gln Glu Gly Ser
 65                  70                  75                  80

Ser Ser Asp Ser Leu Asn Asp Leu Tyr Gly Arg Ile Phe Gly Gly Gly
                 85                  90                  95

Asp Ser Ser Asp Ser Ser Gln Glu Asn Ser Lys Asp Ser Asp Gly Leu
            100                 105                 110

Gln Val Ala Gly Glu Gly Ser Gly Val Ile Tyr Lys Lys Asp Gly Lys
        115                 120                 125

Glu Ala Tyr Ile Val Thr Asn Asn His Val Val Asp Gly Ala Lys Lys
    130                 135                 140

Leu Glu Ile Met Leu Ser Asp Gly Ser Lys Ile Thr Gly Glu Leu Val
145                 150                 155                 160

Gly Lys Asp Thr Tyr Ser Asp Leu Ala Val Val Lys Val Ser Ser Asp
                165                 170                 175

Lys Ile Thr Thr Val Ala Glu Phe Ala Asp Ser Asn Ser Leu Thr Val
            180                 185                 190

Gly Glu Lys Ala Ile Ala Ile Gly Ser Pro Leu Gly Thr Glu Tyr Ala
        195                 200                 205

Asn Ser Val Thr Glu Gly Ile Val Ser Leu Ser Arg Thr Ile Thr
    210                 215                 220

Met Gln Asn Asp Asn Gly Glu Thr Val Ser Thr Asn Ala Ile Gln Thr
225                 230                 235                 240

Asp Ala Ala Ile Asn Pro Gly Asn Ser Gly Gly Ala Leu Val Asn Ile
                245                 250                 255

Glu Gly Gln Val Ile Gly Ile Asn Ser Ser Lys Ile Ser Ser Thr Ser
            260                 265                 270

Ala Val Ala Gly Ser Ala Val Glu Gly Met Gly Phe Ala Ile Pro Ser
```

```
                275                 280                 285
Asn Asp Val Val Glu Ile Ile Asn Gln Leu Glu Lys Asp Gly Lys Val
            290                 295                 300

Thr Arg Pro Ala Leu Gly Ile Ser Ile Ala Asp Leu Asn Ser Leu Ser
305                 310                 315                 320

Ser Ser Ala Thr Ser Lys Leu Asp Leu Pro Asp Glu Val Lys Ser Gly
                325                 330                 335

Val Val Val Gly Ser Val Gln Lys Gly Met Pro Ala Asp Gly Lys Leu
            340                 345                 350

Gln Glu Tyr Asp Val Ile Thr Glu Ile Asp Gly Lys Lys Ile Ser Ser
                355                 360                 365

Lys Thr Asp Ile Gln Thr Asn Leu Tyr Ser His Ser Ile Gly Asp Thr
370                 375                 380

Ile Lys Val Thr Phe Tyr Arg Gly Lys Asp Lys Lys Thr Val Asp Leu
385                 390                 395                 400

Lys Leu Thr Lys Ser Thr Glu Asp Ile Ser Asp
                405                 410

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaagttcagc agcaag                                                       16

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccggcagttt gttgggtg                                                     18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggcaaaagct aatatagg                                                     18

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtattgacat ttaccg                                                       16

<210> SEQ ID NO 15
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgtgggccct tttaaatggg cag                                            23

<210> SEQ ID NO 16
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gagatctcta atgatgatga tgatgatgaa cctcttggga caagtgaacc tgtgattttt    60
tcaatcacg                                                            69

<210> SEQ ID NO 17
<211> LENGTH: 1224
<212> TYPE: DNA
<213> ORGANISM: Lactococcus lactis

<400> SEQUENCE: 17
atggcaaaag ctaatatagg aaaattgcta ttaaccggcg ttgtgggtgg agctatcgca    60
ctcggaggaa gcgcaattta tcaaagcact acaaaccaac taggaaatgc taaccgctca   120
aatacgacta gcacaaaggt tagtaatgtt tcggtaaatg tcaataccga tgttacctct   180
gcaattaaaa aagtttcaaa ttctgtcgtt tctgttatga attatcaaaa acagaattca   240
caaagtgatt ttagttcaat ttttggtgga aatagcggct caagttcagc taatgacggc   300
ttgcaacttt ccagtgaggg ttctggtgtt atttacaaaa aatctggtgg agatgcttac   360
gtggtcacta actatcacgt tattgccgga aatagttccc tcgatgtttt actttctggt   420
gggcaaaaag ttaaagccac agttgttggt tatgatgaat acactgacct tgccgttctt   480
aaaatcagct ctgaccatgt taaagacgtg caactttcg ctgattcaag caagttaact   540
attggtgaac cagctattgc agtcggctca ccttttaggta gccagtttgc taatactgca   600
accgaaggaa ttctgtctgc aacaagtcgt caagtcactt tgactcaaga aaatggtcaa   660
acaacaagta tcaatgcgat tcaaacggat gctgccatta accctggtaa ctcaggtgga   720
gccttgatta atattgaagg tcaagtgatt ggtattactc aaagtaaaat cacaacgact   780
gaagatggtt ctacctctgt ggaaggttta ggttttgcta tcccatctaa tgatgtggta   840
aacatcatta taaacttga aactgatggt aagatttcac gtcctgcctt aggtattcgt   900
atggttgacc tatctcaatt atcaacaaat gatagttctc aactgaaatt acctagcagc   960
gtaactggtg gagtggttgt ctactctgtt caagcgggtc ttcctgctgc cacagctggt  1020
ctgaaagctg gcgatgtgat aacgaaggtg ggagataccg ccgttacttc atcaacagac  1080
ttacaaagtg ctctttactc acacaatatt aatgatactg tgaaagtcac ctactaccgt  1140
gatggtaaat cagccacagc aaatgtcaaa ctctctaaat caacaagcga tttagaaaca  1200
aatagtccat cttccttctaa ttaa                                         1224

<210> SEQ ID NO 18
<211> LENGTH: 1902
<212> TYPE: PRT
```

<213> ORGANISM: Lactococcus lactis

<400> SEQUENCE: 18

Met Gln Arg Lys Lys Gly Leu Ser Ile Leu Leu Ala Gly Thr Val
1               5                   10                  15

Ala Leu Gly Ala Leu Ala Val Leu Pro Val Gly Glu Ile Gln Ala Lys
            20                  25                  30

Ala Ala Ile Ser Gln Gln Thr Lys Gly Ser Ser Leu Ala Asn Thr Val
        35                  40                  45

Thr Ala Thr Ala Lys Gln Ala Ala Thr Asp Thr Thr Ala Ala Thr
    50                  55                  60

Thr Asn Gln Ala Ile Ala Thr Gln Leu Ala Ala Lys Gly Ile Asp Tyr
65                  70                  75                  80

Asn Lys Leu Asn Lys Val Gln Gln Gln Asp Ile Tyr Val Asp Val Ile
                85                  90                  95

Val Gln Met Ser Ala Ala Pro Ala Ser Glu Asn Gly Ile Leu Arg Thr
            100                 105                 110

Asp Tyr Ser Ser Thr Ala Glu Ile Gln Gln Glu Thr Asn Lys Val Ile
        115                 120                 125

Ala Ala Gln Ala Ser Val Lys Ala Ala Val Glu Gln Val Thr Gln Gln
    130                 135                 140

Thr Ala Gly Glu Ser Tyr Gly Tyr Val Val Asn Gly Phe Ser Thr Lys
145                 150                 155                 160

Val Arg Val Val Asp Ile Pro Lys Leu Lys Gln Ile Ala Gly Val Lys
                165                 170                 175

Thr Val Thr Leu Ala Lys Val Tyr Tyr Pro Thr Asp Ala Lys Ala Asn
            180                 185                 190

Ser Met Ala Asn Val Gln Ala Val Trp Ser Asn Tyr Lys Tyr Lys Gly
        195                 200                 205

Glu Gly Thr Val Val Ser Val Ile Asp Ser Gly Ile Asp Pro Thr His
    210                 215                 220

Lys Asp Met Arg Leu Ser Asp Asp Lys Asp Val Lys Leu Thr Lys Ser
225                 230                 235                 240

Asp Val Glu Lys Phe Thr Asp Thr Val Lys His Gly Arg Tyr Phe Asn
                245                 250                 255

Ser Lys Val Pro Tyr Gly Phe Asn Tyr Ala Asp Asn Asn Asp Thr Ile
            260                 265                 270

Thr Asp Asp Lys Val Asp Glu Gln His Gly Met His Val Ala Gly Ile
        275                 280                 285

Ile Gly Ala Asn Gly Thr Gly Asp Asp Pro Ala Lys Ser Val Val Gly
    290                 295                 300

Val Ala Pro Glu Ala Gln Leu Leu Ala Met Lys Val Phe Ser Asn Ser
305                 310                 315                 320

Asp Thr Ser Ala Lys Thr Gly Ser Ala Thr Val Val Ser Ala Ile Glu
                325                 330                 335

Asp Ser Ala Lys Ile Gly Ala Asp Val Leu Asn Met Ser Leu Gly Ser
            340                 345                 350

Asn Ser Gly Asn Gln Thr Leu Glu Asp Pro Glu Leu Ala Ala Val Gln
        355                 360                 365

Asn Ala Asn Glu Ser Gly Thr Ala Ala Val Ile Ser Ala Gly Asn Ser
    370                 375                 380

Gly Thr Ser Gly Ser Ala Thr Glu Gly Val Asn Lys Asp Tyr Tyr Gly
385                 390                 395                 400

Leu Gln Asp Asn Glu Met Val Gly Ser Pro Gly Thr Ser Arg Gly Ala

-continued

```
                405                 410                 415
Thr Thr Val Ala Ser Ala Glu Asn Thr Asp Val Ile Thr Gln Ala Val
            420                 425                 430

Thr Ile Thr Asp Gly Thr Gly Leu Gln Leu Gly Pro Glu Thr Ile Gln
        435                 440                 445

Leu Ser Ser His Asp Phe Thr Gly Ser Phe Asp Gln Lys Lys Phe Tyr
    450                 455                 460

Ile Val Lys Asp Ala Ser Gly Asn Leu Ser Lys Gly Ala Leu Ala Asp
465                 470                 475                 480

Tyr Thr Ala Asp Ala Lys Gly Lys Ile Ala Ile Val Lys Arg Gly Glu
                485                 490                 495

Phe Ser Phe Asp Asp Lys Gln Lys Tyr Ala Gln Ala Ala Gly Ala Ala
            500                 505                 510

Gly Leu Ile Ile Val Asn Thr Asp Gly Thr Ala Thr Pro Met Thr Ser
        515                 520                 525

Ile Ala Leu Thr Thr Thr Phe Pro Thr Phe Gly Leu Ser Ser Val Thr
    530                 535                 540

Gly Gln Lys Leu Val Asp Trp Val Thr Ala His Pro Asp Asp Ser Leu
545                 550                 555                 560

Gly Val Lys Ile Thr Leu Ala Met Leu Pro Asn Gln Lys Tyr Thr Glu
                565                 570                 575

Asp Lys Met Ser Asp Phe Thr Ser Tyr Gly Pro Val Ser Asn Leu Ser
            580                 585                 590

Phe Lys Pro Asp Ile Thr Ala Pro Gly Gly Asn Ile Trp Ser Thr Gln
        595                 600                 605

Asn Asn Asn Gly Tyr Thr Asn Met Ser Gly Thr Ser Met Ala Ser Pro
    610                 615                 620

Phe Ile Ala Gly Ser Gln Ala Leu Leu Lys Gln Ala Leu Asn Asn Lys
625                 630                 635                 640

Asn Asn Pro Phe Tyr Ala Tyr Tyr Lys Gln Leu Lys Gly Thr Ala Leu
                645                 650                 655

Thr Asp Phe Leu Lys Thr Val Glu Met Asn Thr Ala Gln Pro Ile Asn
            660                 665                 670

Asp Ile Asn Tyr Asn Asn Val Ile Val Ser Pro Arg Arg Gln Gly Ala
        675                 680                 685

Gly Leu Val Asp Val Lys Ala Ala Ile Asp Ala Leu Glu Lys Asn Pro
    690                 695                 700

Ser Thr Val Val Ala Glu Asn Gly Tyr Pro Ala Val Glu Leu Lys Asp
705                 710                 715                 720

Phe Thr Ser Thr Asp Lys Thr Phe Lys Leu Thr Phe Thr Asn Arg Thr
                725                 730                 735

Thr His Glu Leu Thr Tyr Gln Met Asp Ser Asn Thr Asp Thr Asn Ala
            740                 745                 750

Val Tyr Thr Ser Ala Thr Asp Pro Asn Ser Gly Val Leu Tyr Asp Lys
        755                 760                 765

Lys Ile Asp Gly Ala Ala Ile Lys Ala Gly Ser Asn Ile Thr Val Pro
770                 775                 780

Ala Gly Lys Thr Ala Gln Ile Glu Phe Thr Leu Ser Leu Pro Lys Ser
785                 790                 795                 800

Phe Asp Gln Gln Gln Phe Val Glu Gly Phe Leu Asn Phe Lys Gly Ser
                805                 810                 815

Asp Gly Ser Arg Leu Asn Leu Pro Tyr Met Gly Phe Phe Gly Asp Trp
            820                 825                 830
```

-continued

```
Asn Asp Gly Lys Ile Val Asp Ser Leu Asn Gly Ile Thr Tyr Ser Pro
            835                 840                 845

Ala Gly Gly Asn Phe Gly Thr Val Pro Leu Leu Lys Asn Lys Asn Thr
    850                 855                 860

Gly Thr Gln Tyr Tyr Gly Gly Met Val Thr Asp Ala Asp Gly Asn Lys
865                 870                 875                 880

Thr Val Asp Asp Gln Ala Ile Ala Phe Ser Asp Lys Asn Ala Leu
                885                 890                 895

Tyr Asn Asp Ile Ser Met Lys Tyr Tyr Leu Leu Arg Asn Ile Ser Asn
                900                 905                 910

Val Gln Val Asp Ile Leu Asp Gly Gln Gly Asn Lys Val Thr Thr Leu
                915                 920                 925

Ser Ser Ser Thr Asn Arg Lys Lys Thr Tyr Tyr Asn Ala His Ser Gln
        930                 935                 940

Gln Tyr Ile Tyr Tyr Asn Ala Pro Ala Trp Asp Gly Thr Tyr Tyr Asp
945                 950                 955                 960

Gln Arg Asp Gly Asn Ile Lys Thr Ala Asp Asp Gly Ser Tyr Thr Tyr
                965                 970                 975

Arg Ile Ser Gly Val Pro Glu Gly Gly Asp Lys Arg Gln Val Phe Asp
            980                 985                 990

Val Pro Phe Lys Leu Asp Ser Lys Ala Pro Thr Val Arg His Val Ala
        995                 1000                1005

Leu Ser Ala Lys Thr Glu Asn Gly Lys Thr Gln Tyr Tyr Leu Thr Ala
    1010                1015                1020

Glu Ala Lys Asp Asp Leu Ser Gly Leu Asp Ala Thr Lys Ser Val Lys
1025                1030                1035                1040

Thr Glu Ile Asn Glu Val Thr Asn Leu Asp Ala Thr Phe Thr Asp Ala
                1045                1050                1055

Gly Thr Thr Ala Asp Gly Tyr Thr Lys Ile Glu Thr Pro Leu Ser Asp
            1060                1065                1070

Glu Gln Ala Gln Ala Leu Gly Asn Gly Asp Asn Ser Ala Glu Leu Tyr
        1075                1080                1085

Leu Thr Asp Asn Ala Ser Asn Ala Thr Asp Gln Asp Ala Ser Val Gln
    1090                1095                1100

Lys Pro Gly Ser Thr Ser Phe Asp Leu Ile Val Asn Gly Gly Ile
1105                1110                1115                1120

Pro Asp Lys Ile Ser Ser Thr Thr Gly Tyr Glu Ala Asn Thr Gln
                1125                1130                1135

Gly Gly Gly Thr Tyr Thr Phe Ser Gly Thr Tyr Pro Ala Ala Val Asp
            1140                1145                1150

Gly Thr Tyr Thr Asp Ala Gln Gly Lys Lys His Asp Leu Asn Thr Thr
    1155                1160                1165

Tyr Asp Ala Ala Thr Asn Ser Phe Thr Ala Ser Met Pro Val Thr Asn
1170                1175                1180

Ala Asp Tyr Ala Ala Gln Val Asp Leu Tyr Ala Asp Lys Ala His Thr
1185                1190                1195                1200

Gln Leu Leu Lys His Phe Asp Thr Lys Val Arg Leu Met Ala Pro Thr
    1205                1210                1215

Phe Thr Asp Leu Lys Phe Asn Asn Gly Ser Asp Gln Thr Ser Glu Ala
        1220                1225                1230

Thr Ile Lys Val Thr Gly Thr Val Ser Ala Asp Thr Lys Thr Val Asn
    1235                1240                1245

Val Gly His Thr Val Ala Ala Leu Asp Ala Gln His His Phe Ser Val
    1250                1255                1260
```

```
Asp Val Pro Val Asn Tyr Gly Asp Asn Thr Ile Lys Val Thr Ala Thr
1265                1270                1275                1280

Asp Lys Asp Gly Asn Thr Thr Thr Glu Gln Lys Thr Ile Thr Ser Ser
            1285                1290                1295

Tyr Asp Pro Asp Met Leu Lys Lys Ser Val Thr Phe Asp Gln Gly Val
        1300                1305                1310

Lys Phe Gly Thr Asn Lys Phe Asn Ala Thr Ser Ala Lys Phe Tyr Asp
    1315                1320                1325

Pro Lys Thr Gly Ile Ala Thr Ile Thr Gly Lys Val Lys His Pro Thr
1330                1335                1340

Thr Thr Leu Gln Val Asp Gly Lys Gln Ile Pro Ile Lys Asp Asp Leu
1345                1350                1355                1360

Thr Phe Ser Phe Thr Leu Asp Leu Gly Thr Leu Gly Gln Lys Pro Phe
            1365                1370                1375

Gly Val Val Val Gly Asp Thr Thr Gln Asn Lys Thr Phe Gln Glu Ala
        1380                1385                1390

Leu Ser Phe Ile Leu Asp Ala Val Ala Pro Thr Leu Ser Leu Asp Ser
    1395                1400                1405

Ser Thr Asp Ala Pro Val Tyr Thr Asn Asp Pro Asn Phe Gln Ile Thr
1410                1415                1420

Gly Thr Ala Thr Asp Asn Ala Gln Tyr Leu Ser Leu Ser Ile Asn Gly
1425                1430                1435                1440

Ser Ser Val Ala Ser Gln Tyr Glu Asp Ile Asn Ile Asn Ser Gly Lys
            1445                1450                1455

Pro Gly His Met Ala Ile Asp Gln Pro Val Lys Leu Leu Glu Gly Lys
        1460                1465                1470

Asn Val Leu Thr Val Ala Val Thr Asp Ser Glu Asp Asn Thr Thr Thr
    1475                1480                1485

Lys Asn Ile Thr Val Tyr Tyr Glu Pro Lys Lys Thr Leu Ala Ala Pro
    1490                1495                1500

Thr Val Thr Pro Ser Thr Thr Glu Pro Ala Gln Thr Val Thr Leu Thr
1505                1510                1515                1520

Ala Asn Ala Ala Ala Thr Gly Glu Thr Val Gln Tyr Ser Ala Asp Gly
            1525                1530                1535

Gly Lys Thr Tyr Gln Asp Val Pro Ala Ala Gly Val Thr Ile Thr Ala
        1540                1545                1550

Asn Gly Thr Phe Lys Phe Lys Ser Thr Asp Leu Tyr Gly Asn Glu Ser
    1555                1560                1565

Pro Ala Val Asp Tyr Val Val Thr Asn Ile Lys Ala Asp Asp Pro Ala
    1570                1575                1580

Gln Leu Gln Ala Ala Lys Gln Glu Leu Thr Asn Leu Ile Ala Ser Ala
1585                1590                1595                1600

Lys Thr Leu Ser Ala Ser Gly Lys Tyr Asp Asp Ala Thr Thr Thr Ala
            1605                1610                1615

Leu Ala Ala Ala Thr Gln Lys Ala Gln Thr Ala Leu Asp Gln Thr Asn
        1620                1625                1630

Ala Ser Val Asp Ser Leu Thr Gly Ala Asn Arg Asp Leu Gln Thr Ala
    1635                1640                1645

Ile Asn Gln Leu Ala Ala Lys Leu Pro Ala Asp Lys Lys Thr Ser Leu
    1650                1655                1660

Leu Asn Gln Leu Gln Ser Val Lys Asp Ala Leu Gly Thr Asp Leu Gly
1665                1670                1675                1680

Asn Gln Thr Asp Pro Ser Thr Gly Lys Thr Phe Thr Ala Ala Leu Asp
```

```
                    1685                1690                1695
Asp Leu Val Ala Gln Ala Gln Ala Gly Thr Gln Thr Asp Asp Gln Leu
        1700                1705                1710

Gln Ala Thr Leu Ala Lys Ile Leu Asp Glu Val Leu Ala Lys Leu Ala
    1715                1720                1725

Glu Gly Ile Lys Ala Ala Thr Pro Ala Glu Val Gly Asn Ala Lys Asp
1730                1735                1740

Ala Ala Thr Gly Lys Thr Trp Tyr Ala Asp Ile Ala Asp Thr Leu Thr
1745                1750                1755                1760

Ser Gly Gln Ala Ser Ala Asp Ala Ser Asp Lys Leu Ala His Leu Gln
            1765                1770                1775

Ala Leu Gln Ser Leu Lys Thr Lys Val Ala Ala Val Glu Ala Ala
        1780                1785                1790

Lys Thr Val Gly Lys Gly Asp Gly Thr Thr Gly Thr Ser Asp Lys Gly
    1795                1800                1805

Gly Gly Gln Gly Thr Pro Ala Pro Ala Pro Gly Asp Thr Gly Lys Asp
1810                1815                1820

Lys Gly Asp Glu Gly Ser Gln Pro Ser Ser Gly Gly Asn Ile Pro Thr
1825                1830                1835                1840

Lys Pro Ala Thr Thr Thr Ser Thr Thr Thr Asp Asp Thr Thr Asp Arg
            1845                1850                1855

Asn Gly Gln Leu Thr Ser Gly Lys Gly Ala Leu Pro Lys Thr Gly Glu
        1860                1865                1870

Thr Thr Glu Arg Pro Ala Phe Gly Phe Leu Gly Val Ile Val Val Ser
    1875                1880                1885

Leu Met Gly Val Leu Gly Leu Lys Arg Lys Gln Arg Glu Glu
1890                1895                1900

<210> SEQ ID NO 19
<211> LENGTH: 744
<212> TYPE: PRT
<213> ORGANISM: Lactococcus lactis
<220> FEATURE:
<221> NAME/KEY: MOD_RES
<222> LOCATION: (374)
<223> OTHER INFORMATION: variable amino acid
<220> FEATURE:
<221> NAME/KEY: MOD_RES
<222> LOCATION: (744)
<223> OTHER INFORMATION: variable amino acid

<400> SEQUENCE: 19

Met Gln Arg Lys Lys Gly Leu Ser Ile Leu Leu Ala Gly Thr Val
1               5                   10                  15

Ala Leu Gly Ala Leu Ala Val Leu Pro Val Gly Glu Ile Gln Ala Lys
            20                  25                  30

Ala Ala Ile Ser Gln Gln Thr Lys Gly Ser Ser Leu Ala Asn Thr Val
        35                  40                  45

Thr Ala Thr Ala Lys Gln Ala Ala Thr Asp Thr Thr Ala Ala Thr
    50                  55                  60

Thr Asn Gln Ala Ile Ala Thr Gln Leu Ala Ala Lys Gly Ile Asp Tyr
65                  70                  75                  80

Asn Lys Leu Asn Lys Val Gln Gln Gln Asp Ile Tyr Val Asp Val Ile
                85                  90                  95

Val Gln Met Ser Ala Ala Pro Ala Ser Glu Asn Gly Thr Leu Arg Thr
            100                 105                 110

Asp Tyr Ser Ser Thr Ala Glu Ile Gln Gln Glu Thr Asn Lys Val Ile
        115                 120                 125
```

```
Ala Ala Gln Ala Ser Val Lys Ala Ala Val Glu Gln Val Thr Gln Gln
        130                 135                 140
Thr Ala Gly Glu Ser Tyr Gly Tyr Val Val Asn Gly Phe Ser Thr Lys
145                 150                 155                 160
Val Arg Val Val Asp Ile Pro Lys Leu Lys Gln Ile Ala Gly Val Lys
                165                 170                 175
Thr Val Thr Leu Ala Lys Val Tyr Tyr Pro Thr Asp Ala Lys Ala Asn
            180                 185                 190
Ser Met Ala Asn Val Gln Ala Val Trp Ser Asn Tyr Lys Tyr Lys Gly
        195                 200                 205
Glu Gly Thr Val Val Ser Val Ile Asp Ser Gly Ile Asp Pro Thr His
    210                 215                 220
Lys Asp Met Arg Leu Ser Asp Lys Asp Val Lys Leu Thr Lys Ser
225                 230                 235                 240
Asp Val Glu Lys Phe Thr Asp Thr Ala Lys His Gly Arg Tyr Phe Asn
                245                 250                 255
Ser Lys Val Pro Tyr Gly Phe Asn Tyr Ala Asp Asn Asn Asp Thr Ile
            260                 265                 270
Thr Asp Asp Thr Val Asp Glu Gln His Gly Met His Val Ala Gly Ile
        275                 280                 285
Ile Gly Ala Asn Gly Thr Gly Asp Asp Pro Ala Lys Ser Val Val Gly
    290                 295                 300
Val Ala Pro Glu Ala Gln Leu Leu Ala Met Lys Val Phe Thr Asn Ser
305                 310                 315                 320
Asp Thr Ser Ala Thr Thr Gly Ser Ala Thr Leu Val Ser Ala Ile Glu
                325                 330                 335
Asp Ser Ala Lys Ile Gly Ala Asp Val Leu Asn Met Ser Leu Gly Ser
            340                 345                 350
Asp Ser Gly Asn Gln Thr Leu Glu Asp Pro Glu Leu Ala Ala Val Gln
        355                 360                 365
Asn Ala Asn Glu Ser Xaa Thr Ala Ala Val Ile Ser Ala Gly Asn Ser
    370                 375                 380
Gly Thr Ser Gly Ser Ala Thr Glu Gly Val Asn Lys Asp Tyr Tyr Gly
385                 390                 395                 400
Leu Gln Asp Asn Glu Met Val Gly Thr Pro Gly Thr Ser Arg Gly Ala
                405                 410                 415
Thr Thr Val Ala Ser Ala Glu Asn Thr Asp Val Ile Thr Gln Ala Val
            420                 425                 430
Thr Ile Thr Asp Gly Thr Gly Leu Gln Leu Gly Pro Glu Thr Ile Gln
        435                 440                 445
Leu Ser Ser Asn Asp Phe Thr Gly Ser Phe Asp Gln Lys Lys Phe Tyr
    450                 455                 460
Val Val Lys Asp Ala Ser Gly Asn Leu Ser Lys Gly Lys Val Ala Asp
465                 470                 475                 480
Tyr Thr Ala Asp Ala Lys Gly Lys Ile Ala Ile Val Lys Arg Gly Glu
                485                 490                 495
Leu Thr Phe Ala Asp Lys Gln Lys Tyr Ala Gln Ala Ala Gly Ala Ala
            500                 505                 510
Gly Leu Ile Ile Val Asn Asn Asp Gly Thr Ala Thr Pro Val Thr Ser
        515                 520                 525
Met Ala Leu Thr Thr Thr Phe Pro Thr Phe Gly Leu Ser Ser Val Thr
    530                 535                 540
Gly Gln Lys Leu Val Asp Trp Val Ala Ala His Pro Asp Asp Ser Leu
```

```
                545                 550                 555                 560
Gly Val Lys Ile Ala Leu Thr Leu Val Pro Asn Gln Lys Tyr Thr Glu
                565                 570                 575

Asp Lys Met Ser Asp Phe Thr Ser Tyr Gly Pro Val Ser Asn Leu Ser
            580                 585                 590

Phe Lys Pro Asp Ile Thr Ala Pro Gly Gly Asn Ile Trp Ser Thr Gln
        595                 600                 605

Asn Asn Asn Gly Tyr Thr Asn Met Ser Gly Thr Ser Met Ala Ser Pro
    610                 615                 620

Phe Ile Ala Gly Ser Gln Ala Leu Leu Lys Gln Ala Leu Asn Asn Lys
625                 630                 635                 640

Asn Asn Pro Phe Tyr Ala Tyr Lys Gln Leu Lys Gly Thr Ala Leu
                645                 650                 655

Thr Asp Phe Leu Lys Thr Val Glu Met Asn Thr Ala Gln Pro Ile Asn
                660                 665                 670

Asp Ile Asn Tyr Asn Asn Val Ile Val Ser Pro Arg Arg Gln Gly Ala
            675                 680                 685

Gly Leu Val Asp Val Lys Ala Ala Ile Asp Ala Leu Glu Lys Asn Pro
    690                 695                 700

Ser Thr Val Val Ala Glu Asn Gly Tyr Pro Ala Val Glu Leu Lys Asp
705                 710                 715                 720

Phe Thr Ser Thr Asp Lys Thr Phe Lys Leu Thr Phe Thr Asn Arg Thr
                725                 730                 735

Thr His Glu Leu Thr Tyr Gln Xaa
            740

<210> SEQ ID NO 20
<211> LENGTH: 264
<212> TYPE: PRT
<213> ORGANISM: Lactococcus lactis

<400> SEQUENCE: 20

Ala Ala Ala Thr Gln Lys Ala Gln Thr Ala Leu Asp Gln Thr Asn Ala
1               5                   10                  15

Ser Val Asp Ser Leu Thr Gly Ala Asn Arg Asp Leu Gln Thr Ala Ile
                20                  25                  30

Asn Gln Leu Ala Ala Lys Leu Pro Ala Asp Lys Lys Thr Ser Leu Leu
            35                  40                  45

Asn Gln Leu Gln Ser Val Lys Ala Ala Leu Glu Thr Asp Leu Gly Asn
        50                  55                  60

Gln Thr Asp Ser Ser Thr Gly Lys Thr Phe Thr Ala Ala Leu Asp Asp
65                  70                  75                  80

Leu Val Ala Gln Ala Gln Ala Gly Thr Gln Thr Asp Asp Gln Leu Gln
                85                  90                  95

Ala Thr Leu Ala Lys Val Leu Asp Ala Val Leu Ala Lys Leu Ala Glu
            100                 105                 110

Gly Ile Lys Ala Ala Thr Pro Ala Glu Val Gly Asn Ala Lys Asp Ala
        115                 120                 125

Ala Thr Gly Lys Thr Trp Tyr Ala Asp Ile Ala Asp Thr Leu Thr Ser
    130                 135                 140

Gly Gln Ala Ser Ala Asp Ala Ser Asp Lys Leu Ala His Leu Gln Ala
145                 150                 155                 160

Leu Gln Ser Leu Lys Thr Lys Val Ala Ala Val Glu Ala Ala Lys
                165                 170                 175

Thr Val Gly Lys Gly Asp Gly Thr Thr Gly Thr Ser Asp Lys Gly Gly
```

```
            180                 185                 190
Gly Gln Gly Thr Pro Ala Pro Thr Pro Gly Asp Ile Gly Lys Asp Lys
            195                 200                 205

Gly Asp Glu Gly Ser Gln Pro Ser Ser Gly Gly Asn Ile Pro Thr Asn
        210                 215                 220

Pro Ala Thr Thr Thr Ser Thr Ser Thr Asp Asp Thr Asp Arg Asn
225                 230                 235                 240

Gly Gln Leu Thr Ser Gly Lys Gly Ala Leu Pro Lys Thr Gly Glu Thr
                245                 250                 255

Thr Glu Arg Pro Ala Phe Gly Phe
            260

<210> SEQ ID NO 21
<211> LENGTH: 1915
<212> TYPE: PRT
<213> ORGANISM: Lactobacillus casei

<400> SEQUENCE: 21

Ser Leu Val Leu Lys Leu Gly Ser Gly Gly Tyr Trp Met Gln Arg
  1               5                  10                  15

Lys Lys Lys Gly Leu Ser Ile Leu Ala Gly Thr Val Ala Leu Gly
             20                  25                  30

Ala Leu Ala Val Leu Pro Val Gly Glu Ile Gln Ala Lys Ala Ala Ile
             35                  40                  45

Ser Gln Gln Thr Lys Gly Ser Ser Leu Ala Asn Thr Val Lys Ala Ala
         50                  55                  60

Thr Ala Lys Gln Ala Ala Thr Asp Thr Thr Ala Ala Thr Thr Asn Gln
 65                  70                  75                  80

Ala Ile Ala Thr Gln Leu Ala Ala Lys Gly Ile Asp Tyr Asn Lys Leu
                 85                  90                  95

Asn Lys Val Gln Gln Gln Asp Thr Tyr Val Asp Val Ile Val Gln Met
            100                 105                 110

Ser Ala Ala Pro Ala Ser Glu Asn Gly Thr Leu Arg Thr Asp Tyr Ser
        115                 120                 125

Ser Thr Ala Glu Ile Gln Gln Glu Thr Asn Lys Val Ile Ala Ala Gln
    130                 135                 140

Ala Ser Val Lys Ala Ala Val Glu Gln Val Thr Gln Gln Thr Ala Gly
145                 150                 155                 160

Glu Ser Tyr Gly Tyr Val Val Asn Gly Phe Ser Thr Lys Val Arg Val
                165                 170                 175

Val Asp Ile Pro Lys Leu Lys Gln Ile Ala Gly Val Lys Thr Val Thr
            180                 185                 190

Leu Ala Lys Val Tyr Tyr Pro Thr Asp Ala Lys Ala Asn Ser Met Ala
        195                 200                 205

Asn Val Gln Ala Val Trp Ser Asn Tyr Lys Tyr Lys Gly Glu Gly Thr
    210                 215                 220

Val Val Ser Val Ile Asp Thr Gly Ile Asp Pro Thr His Lys Asp Met
225                 230                 235                 240

Arg Leu Ser Asp Asp Lys Asp Val Lys Leu Thr Lys Ser Asp Val Glu
                245                 250                 255

Lys Phe Thr Asp Thr Ala Lys His Gly Arg Tyr Phe Thr Ser Lys Val
            260                 265                 270

Pro Tyr Gly Phe Asn Tyr Ala Asp Asn Asn Asp Thr Ile Thr Asp Asp
        275                 280                 285

Thr Val Asp Glu Gln His Gly Met His Val Ala Gly Ile Ile Gly Ala
```

```
            290                 295                 300
Asn Gly Thr Gly Asp Asp Pro Thr Lys Ser Val Val Gly Val Ala Pro
305                 310                 315                 320

Glu Ala Gln Leu Leu Ala Met Lys Val Phe Thr Asn Ser Asp Thr Ser
                325                 330                 335

Ala Thr Thr Gly Ser Ala Thr Leu Val Ser Ala Ile Glu Asp Ser Ala
                340                 345                 350

Lys Ile Gly Ala Asp Val Leu Asn Met Ser Leu Gly Ser Asp Ser Gly
                355                 360                 365

Asn Gln Thr Leu Glu Asp Pro Glu Ile Ala Ala Val Gln Asn Ala Asn
370                 375                 380

Glu Ser Gly Thr Ala Ala Val Ile Ser Ala Gly Asn Ala Gly Thr Ser
385                 390                 395                 400

Gly Ser Ala Thr Gln Gly Val Asn Lys Asp Tyr Tyr Gly Leu Gln Asp
                405                 410                 415

Asn Glu Met Val Gly Thr Pro Gly Thr Ser Arg Gly Ala Thr Thr Val
                420                 425                 430

Ala Ser Ala Glu Asn Thr Asp Val Ile Ser Gln Ala Val Thr Ile Thr
                435                 440                 445

Asp Gly Lys Glu Leu Gln Leu Gly Pro Glu Thr Ile Gln Leu Ser Ser
450                 455                 460

Asn Asp Phe Thr Gly Ser Phe Asp Gln Lys Lys Phe Tyr Val Val Lys
465                 470                 475                 480

Asp Ala Ser Gly Asp Leu Ser Lys Gly Ala Ala Asp Tyr Thr Ala
                485                 490                 495

Asp Ala Lys Gly Lys Ile Ala Ile Val Lys Arg Gly Glu Leu Thr Phe
                500                 505                 510

Ala Asp Lys Gln Lys Tyr Ala Gln Ala Ala Gly Ala Ala Gly Leu Ile
                515                 520                 525

Ile Val Asn Asn Asp Gly Thr Ala Thr Pro Leu Thr Ser Ile Thr Leu
                530                 535                 540

Thr Thr Thr Phe Pro Thr Phe Gly Leu Ser Ser Val Thr Gly Lys Lys
545                 550                 555                 560

Leu Val Asp Trp Val Thr Ala His Pro Asp Asp Ser Leu Gly Val Lys
                565                 570                 575

Ile Ala Leu Thr Leu Pro Asn Gln Lys Tyr Thr Glu Asp Lys Met
                580                 585                 590

Ser Asp Phe Thr Ser Tyr Gly Pro Val Ser Asn Leu Ser Phe Lys Pro
                595                 600                 605

Asp Ile Thr Ala Pro Gly Gly Asn Ile Trp Ser Thr Gln Asn Asn Asn
                610                 615                 620

Gly Tyr Thr Asn Met Ser Gly Thr Ser Met Ala Ser Pro Phe Ile Ala
625                 630                 635                 640

Gly Ser Gln Ala Leu Leu Lys Gln Ala Leu Asn Asn Lys Asn Asn Pro
                645                 650                 655

Phe Tyr Ala Asp Tyr Lys Gln Leu Lys Gly Thr Ala Leu Thr Asp Phe
                660                 665                 670

Leu Lys Thr Val Glu Met Asn Thr Ala Gln Pro Ile Asn Asp Ile Asn
                675                 680                 685

Tyr Asn Asn Val Ile Val Ser Pro Arg Arg Gln Gly Ala Gly Leu Val
                690                 695                 700

Asp Val Lys Ala Ala Ile Asp Ala Leu Glu Lys Asn Pro Ser Thr Val
705                 710                 715                 720
```

-continued

Val Ala Glu Asn Gly Tyr Pro Ala Val Glu Leu Lys Asp Phe Thr Ser
            725                 730                 735

Thr Asp Lys Thr Phe Lys Leu Thr Phe Thr Asn Arg Thr Thr His Glu
        740                 745                 750

Leu Thr Tyr Gln Met Asp Ser Asn Thr Asp Thr Asn Ala Val Tyr Thr
    755                 760                 765

Ser Ala Thr Asp Pro His Ser Gly Val Leu Tyr Asp Lys Lys Ile Asp
770                 775                 780

Gly Ala Ala Ile Lys Ala Gly Ser Asp Ile Thr Val Pro Ala Gly Lys
785                 790                 795                 800

Thr Ala Gln Ile Glu Phe Thr Leu Ser Leu Pro Lys Ser Phe Asp Gln
                805                 810                 815

Gln Gln Phe Val Glu Gly Phe Leu Asn Phe Lys Gly Ser Asp Gly Ser
            820                 825                 830

Arg Leu Asn Leu Pro Tyr Met Gly Phe Phe Gly Asp Trp Asn Asp Gly
        835                 840                 845

Lys Ile Val Asp Ser Leu Asn Gly Ile Thr Tyr Ser Pro Ala Gly Gly
    850                 855                 860

Asn Tyr Gly Thr Val Pro Leu Leu Thr Asn Lys Asn Thr Gly Asn Gln
865                 870                 875                 880

Tyr Tyr Gly Gly Met Val Thr Asp Ala Asp Gly Asn Gln Thr Val Asp
                885                 890                 895

Asp Gln Ala Ile Ala Phe Ser Ser Asp Lys Asn Ala Leu Tyr Asn Asp
            900                 905                 910

Ile Ser Met Gln Tyr Tyr Leu Leu Arg Asn Ile Ser Asn Val Gln Val
        915                 920                 925

Asp Ile Leu Asp Gly Gln Gly Asn Lys Val Thr Thr Leu Ser Ser Ser
    930                 935                 940

Thr Asn Gln Thr Lys Thr Tyr Asp Ala His Ser Arg Lys Tyr Ile
945                 950                 955                 960

Tyr Tyr Asn Ala Pro Ala Trp Asp Gly Thr Tyr Tyr Asp Gln Arg Asp
                965                 970                 975

Gly Asn Ile Lys Thr Ala Asp Asp Gly Ser Tyr Thr Tyr Arg Ile Ser
            980                 985                 990

Gly Val Pro Glu Gly Gly Asp Lys Arg Gln Val Phe Asp Val Pro Phe
        995                 1000                1005

Lys Leu Asp Ser Lys Ala Pro Thr Val Arg His Val Ala Leu Ser Ala
    1010                1015                1020

Lys Thr Glu Asn Gly Lys Thr Gln Tyr Tyr Leu Thr Ala Glu Ala Lys
1025                1030                1035                1040

Asp Asp Leu Ser Gly Leu Asp Ala Thr Lys Ser Val Lys Thr Ala Ile
                1045                1050                1055

Asn Glu Val Thr Asn Leu Asn Ala Thr Phe Thr Asp Ala Gly Thr Thr
            1060                1065                1070

Ala Asp Gly Tyr Thr Lys Ile Glu Thr Pro Leu Ser Asp Glu Gln Ala
        1075                1080                1085

Gln Ala Leu Gly Asn Gly Asp Asn Ser Ala Glu Leu Tyr Leu Thr Asp
    1090                1095                1100

Asn Ala Ser Asn Ala Thr Asp Gln Asp Ala Ser Val Gln Lys Pro Gly
1105                1110                1115                1120

Ser Thr Ser Phe Asp Leu Ile Val Asn Gly Gly Ile Pro Asp Lys
                1125                1130                1135

Ile Ser Ser Thr Thr Thr Gly Tyr Glu Ala Asn Thr Gln Gly Gly Gly
            1140                1145                1150

```
Thr Tyr Thr Phe Ser Gly Thr Tyr Pro Ala Ala Val Asp Gly Thr Tyr
        1155                1160                1165

Thr Asp Ala Gln Gly Lys Lys His Asp Leu His Thr Thr Tyr Asp Ala
    1170                1175                1180

Ala Thr Asn Ser Phe Thr Ala Ser Met Ala Val Thr Asn Ala Asp Tyr
1185                1190                1195                1200

Ala Ala Gln Val Asp Leu Tyr Ala Asp Lys Ala His Thr Arg Leu Leu
        1205                1210                1215

Lys His Phe Asp Thr Lys Val Arg Leu Thr Ala Pro Thr Phe Thr Asp
        1220                1225                1230

Leu Lys Phe Asn Asn Gly Ser Asp Gln Thr Ser Glu Ala Thr Ile Lys
    1235                1240                1245

Val Thr Gly Thr Val Ser Ala Asp Thr Lys Thr Val Asn Val Gly Asp
    1250                1255                1260

Thr Val Ala Ala Leu Asp Ala Gln His His Phe Ser Val Asp Val Pro
1265                1270                1275                1280

Val Asn Tyr Gly Asp Asn Thr Ile Lys Val Thr Ala Thr Asp Glu Asp
        1285                1290                1295

Gly Asn Thr Thr Thr Glu Gln Lys Thr Ile Thr Ser Ser Tyr Asp Pro
        1300                1305                1310

Asp Val Leu Lys Asn Ala Val Thr Phe Asp Gln Gly Val Thr Phe Gly
        1315                1320                1325

Ala Asn Glu Phe Asn Ala Thr Ser Ser Lys Phe Tyr Asp Pro Lys Thr
    1330                1335                1340

Gly Ile Ala Thr Ile Thr Gly Lys Val Lys His Pro Thr Thr Thr Leu
1345                1350                1355                1360

Gln Val Asp Gly Lys Gln Ile Pro Ile Lys Asp Asp Leu Thr Phe Ser
        1365                1370                1375

Phe Thr Leu Asp Leu Gly Thr Leu Gly Gln Lys Pro Phe Gly Val Val
        1380                1385                1390

Val Gly Asp Thr Thr Gln Asn Lys Thr Phe Gln Glu Ala Leu Thr Phe
        1395                1400                1405

Ile Leu Asp Ala Val Ala Pro Thr Leu Ser Leu Asp Ser Ser Thr Asp
    1410                1415                1420

Ala Pro Val Tyr Thr Asn Asp Pro Asn Phe Gln Ile Thr Gly Thr Ala
1425                1430                1435                1440

Thr Asp Asn Ala Gln Tyr Leu Ser Leu Ala Ile Asn Gly Ser His Val
        1445                1450                1455

Ala Ser Gln Tyr Ala Asp Ile Asn Ile Asn Ser Gly Lys Pro Gly His
        1460                1465                1470

Met Ala Ile Asp Gln Pro Val Lys Leu Leu Glu Gly Lys Asn Val Leu
    1475                1480                1485

Thr Val Ala Val Thr Asp Ser Glu Asn Asn Thr Thr Thr Lys Lys Ile
    1490                1495                1500

Thr Val Tyr Tyr Glu Pro Lys Lys Thr Leu Ala Ala Pro Thr Val Thr
1505                1510                1515                1520

Pro Ser Thr Thr Glu Pro Ala Lys Thr Val Thr Leu Thr Ala Asn Ala
        1525                1530                1535

Ala Ala Thr Gly Glu Thr Val Gln Tyr Ser Ala Asp Gly Gly Lys Thr
        1540                1545                1550

Tyr Gln Asn Val Pro Ala Ala Gly Val Thr Val Thr Ala Asn Gly Thr
    1555                1560                1565

Phe Lys Phe Lys Ser Thr Asp Leu Tyr Gly Asn Glu Ser Pro Ala Val
```

```
                         1570                1575                1580

Asp Tyr Val Val Thr Asn Ile Lys Thr Asp Pro Ala Gln Leu Gln
    1585                1590                1595                1600

Thr Ala Lys Gln Ala Leu Thr Asn Leu Ile Ala Ser Ala Lys Thr Leu
                     1605                1610                1615

Ser Ala Ser Gly Lys Tyr Asp Asp Ala Thr Thr Ala Leu Ala Ala
        1620                1625                1630

Ala Thr Gln Lys Ala Gln Thr Ala Leu Asp Gln Thr Asp Ala Ser Val
             1635                1640                1645

Asp Ser Leu Thr Gly Ala Asn Arg Asp Leu Gln Thr Ala Ile Asn Gln
        1650                1655                1660

Leu Ala Ala Lys Leu Pro Ala Asp Lys Lys Thr Ser Leu Leu Asn Gln
    1665                1670                1675                1680

Leu Gln Ser Val Lys Ala Ala Leu Gly Thr Asp Leu Gly Asn Gln Thr
                     1685                1690                1695

Asp Pro Ser Thr Gly Lys Thr Phe Thr Ala Ala Leu Asp Asp Leu Val
        1700                1705                1710

Ala Gln Ala Gln Ala Gly Thr Gln Thr Ala Asp Gln Leu Gln Ala Thr
             1715                1720                1725

Leu Ala Lys Val Leu Asp Ala Val Leu Ala Lys Leu Ala Glu Gly Ile
        1730                1735                1740

Lys Ala Ala Thr Pro Ala Glu Val Gly Asn Ala Lys Asp Ala Ala Thr
1745                1750                1755                1760

Gly Lys Thr Trp Tyr Ala Asp Ile Ala Asp Thr Leu Thr Ser Gly Gln
                1765                1770                1775

Ala Ser Ala Asp Ala Ser Asp Lys Leu Ala His Leu Gln Ala Leu Gln
             1780                1785                1790

Ser Leu Lys Thr Lys Val Ala Ala Val Glu Ala Ala Lys Thr Ala
        1795                1800                1805

Gly Lys Gly Asp Asp Thr Ser Gly Thr Ser Asp Lys Gly Gly Gly Gln
    1810                1815                1820

Gly Thr Pro Ala Pro Ala Pro Gly Asp Thr Gly Lys Asn Lys Gly Asp
1825                1830                1835                1840

Glu Gly Ser Gln Pro Ser Ser Gly Gly Asn Ile Pro Thr Lys Pro Ala
        1845                1850                1855

Thr Thr Thr Ser Thr Ser Thr Asp Asp Thr Thr Asp Arg Asn Gly Gln
             1860                1865                1870

His Thr Ser Gly Lys Gly Ala Leu Pro Lys Thr Ala Glu Thr Thr Glu
        1875                1880                1885

Arg Pro Ala Phe Gly Phe Leu Gly Val Ile Val Val Ser Leu Met Gly
    1890                1895                1900

Val Leu Gly Leu Lys Arg Lys Gln Arg Glu Glu
1905                1910                1915

<210> SEQ ID NO 22
<211> LENGTH: 1627
<212> TYPE: PRT
<213> ORGANISM: Lactobacillus acidophilus

<400> SEQUENCE: 22

Met Arg Asn Lys Lys Val Gly Ser Val Thr Thr Asp Tyr Ser Tyr Leu
  1               5                  10                  15

Asn Gln Ser Arg Asn His Leu Asn Leu Val Thr Gly Lys Glu Asn Asp
             20                  25                  30

Ser Lys Leu Lys Ile Trp Arg Lys Asn Phe Ala Thr Ala Ala Ile Ile
```

```
                 35                  40                  45
Ala Leu Ala Ser Gly Thr Thr Met Leu Phe Ser Ala His Ser Val Lys
         50                  55                  60

Ala Asp Glu Val Asp Asp Ile Thr Val Gln Asn Asp Lys Gln Val Asn
 65                  70                  75                  80

Thr Thr Ile Val Gln Asn Asn Lys Asp Gln Gln Ser Ser Asp Thr Gln
                 85                  90                  95

Gln Asn Val Asn Glu Asn Arg Ala Ser Ser Gln Ala Ile Arg Arg
            100                 105                 110

Pro Gly Thr Gly Asn Lys Leu Thr Asp Gln Trp Pro Asp Asn Tyr Gln
            115                 120                 125

Ser Asp Gln Gln Asn Asn Ser Ser Gln Ala Glu Thr Thr Lys Ile Ser
        130                 135                 140

Thr Thr Gly Tyr Ser Asn Gln Thr Glu Gln Gln Ser Asn Asn Thr Val
145                 150                 155                 160

Pro Ser Thr Val Ala Ser Ser Thr Val Tyr Lys Glu Ser Ser Asp Asp
                165                 170                 175

Gln Ala Gly Gln Lys Asp Thr Asn Gly Val Glu Leu Pro Ala Asn Asn
            180                 185                 190

Gln Asp His Ile Lys Gly Asn Val Gln Asp Ala Trp Asp Gln Gly Tyr
        195                 200                 205

Lys Gly Gln His Thr Val Val Ala Val Ile Asp Ser Gly Val Asp Thr
        210                 215                 220

Ser His Lys Asp Phe Gln Thr Met Pro Glu Asn Pro Lys Leu Ser Gln
225                 230                 235                 240

Ala Glu Ile Glu Ala Leu Ile Ala Lys Leu Gly Tyr Gly Thr Tyr Ile
                245                 250                 255

Asn Ser Lys Phe Pro Phe Val Tyr Asn Ala Val Asp His Glu Asn Gln
            260                 265                 270

Ser Met Lys Gly Pro Asp Gly Glu Pro His Gly Gln His Val Ser Gly
        275                 280                 285

Ile Ile Ala Ala Asp Gly Gln Pro Asn Gly Asp Gln Glu Tyr Val Val
        290                 295                 300

Gly Val Ala Pro Glu Ala Gln Leu Met His Phe Lys Val Phe Gly Asp
305                 310                 315                 320

Asn Ala Thr Ser Leu Asp Leu Ala Gln Glu Ile Tyr Asp Ala Thr Asn
                325                 330                 335

Leu Gly Ala Asp Val Ile Gln Met Ser Leu Gly Gly Gly Val Ala Ala
            340                 345                 350

Ala Asp Leu Asn Val Ala Asp Gln Arg Ala Val Gln Tyr Ala Ile Asp
        355                 360                 365

His Gly Val Ile Val Ser Ile Ser Ala Ser Asn Asn Gly Asn Ala Ala
        370                 375                 380

Ser Ile Gln Asn Pro Ser Asn Val Thr Asp Leu Asp Asn Tyr Glu Ala
385                 390                 395                 400

Gly Thr His Val Gly Asn Tyr Glu Pro Phe Ser Ser Thr Val Ala
                405                 410                 415

Asp Pro Gly Ala Ala Arg Gly Ala Ile Thr Gly Ala Ala Glu Thr Ser
            420                 425                 430

Gly Leu Gly Asp Lys Ser Asp Met Ala Thr Phe Thr Ser Trp Gly Pro
        435                 440                 445

Leu Pro Asp Phe Thr Leu Lys Pro Asp Val Ser Ala Pro Gly Ser Asn
    450                 455                 460
```

```
Val Ile Ser Leu Ala Asn Asp Asn Gly Tyr Thr Thr Met Ser Gly Thr
465                 470                 475                 480

Ser Met Ala Gly Pro Phe Ile Ala Gly Ala Ala Leu Val Arg Gln
                485                 490                 495

Arg Leu Gln Gln Thr Asn Pro Glu Leu Lys Gly Ala Asp Leu Val Ala
                500                 505                 510

Ala Val Lys Ala Leu Leu Met Asn Thr Ala Asp Pro Gln Ile Gln Gln
            515                 520                 525

Gly Phe Thr Thr Ile Val Ser Pro Arg Arg Gln Gly Ala Gly Gln Ile
        530                 535                 540

Asn Val Gly Ala Ala Thr Lys Ala Pro Val Tyr Ile Leu Ala Asn Asp
545                 550                 555                 560

Gly Thr Gly Ser Val Ser Leu Arg Asn Ile Lys Glu Thr Thr Asn Phe
                565                 570                 575

Glu Leu Thr Phe His Asn Leu Thr Asp Asn Thr Glu Thr Tyr Thr Phe
                580                 585                 590

Asp Asp Leu Gly Gly Phe Thr Glu Val Arg Asp Thr Asp Thr Gly
            595                 600                 605

Leu Phe His Asp Val Gln Leu Ala Gly Ala Arg Val Thr Gly Pro Asn
610                 615                 620

Thr Ile Thr Val Asn Pro Lys Glu Thr Lys Lys Ile Val Phe Thr Leu
625                 630                 635                 640

Asn Leu Thr Gly Leu Lys Gln Asn Gln Leu Val Glu Gly Tyr Leu Asn
                645                 650                 655

Phe Thr Asn Ser Lys Asp Lys Leu Ser Leu Ser Val Pro Tyr Leu Gly
                660                 665                 670

Tyr Tyr Gly Asp Met Thr Ser Glu Asp Val Phe Asp Lys Lys Ala Asn
                675                 680                 685

Glu Asp Lys Pro Asp Ile Lys Gly Asn Arg Leu Thr Asn Glu Asp Asn
            690                 695                 700

Tyr Pro Arg Gly Ile Ala Asp Glu Glu Ser Leu Lys Glu Leu Val Asn
705                 710                 715                 720

Ile Glu Gly Asn Tyr Asn Trp Gln Glu Val Ala Lys Leu Tyr Glu Ser
                725                 730                 735

Gly Lys Val Ala Phe Ser Pro Asn Gly Asp Asn Lys Ser Asp Leu Ile
                740                 745                 750

Met Pro Tyr Val Tyr Leu Lys Gln Asn Leu Gln Asp Leu Lys Val Glu
            755                 760                 765

Ile Leu Asp Ala Lys Gly Asn Val Val Arg Val Leu Ala Asp Ala His
        770                 775                 780

Gly Val Gln Lys Ser Tyr Asn Glu Asp Gly Thr Gly Thr Val Asp Ala
785                 790                 795                 800

Leu Ile Ser Val Asp Ser Gly Lys Phe Asn Trp Asp Gly Lys Val Tyr
                805                 810                 815

Asn Tyr Lys Thr Gly Lys Met Glu Val Ala Pro Asp Gly Gln Tyr Thr
                820                 825                 830

Tyr Arg Phe Val Ala Thr Leu Tyr Asn Asp Gly Pro His Lys Val Gln
                835                 840                 845

Thr Asn Asp Thr Ser Val Ile Ile Asp Thr Thr Ala Pro Ile Leu Lys
            850                 855                 860

Asp Val Glu Tyr Asp Val Thr Thr Lys Thr Ile Thr Gly Thr Tyr Ser
865                 870                 875                 880

Asp Ala Gly Ala Gly Phe Thr Asp Tyr Ser Tyr Ala Thr Val Thr Ile
                885                 890                 895
```

Asn Asp Arg Val Phe Gly Phe Lys Leu Asn Asp Asn Asp Ser Thr
            900                 905                 910

Phe Asp Asn Thr Asp Lys Thr Ile Gly His Phe Ser Phe Ala Leu Thr
            915                 920                 925

Pro Leu Glu Gln Gln Ala Leu Thr Ala Ala His Asn Lys Val Ser Val
            930                 935                 940

Cys Leu Ser Asp Val Ala Asp Asn Thr Ala Val Lys Thr Leu Asp Val
945                 950                 955                 960

Ala Ser Val Gly Asp Gly Asn Lys Ile Ala Ile Trp Asn Ala Val Asn
            965                 970                 975

Gly Val Pro Phe Asn Ser Asn Ser Gln Asp Tyr Ser Asp Lys Asn Asn
            980                 985                 990

Ser Tyr Leu Leu Arg Gly Ser Ala Thr Glu Asn Phe Tyr Val Asn Gly
            995                 1000                1005

Lys Leu Val Gln Val Ala Pro Asn Gly Glu Phe Val Leu Pro Val Ser
     1010                1015                1020

Leu Asp Glu Gln Asn Leu Val Phe Thr Ser Asp Glu Asn Gly Gln Asn
1025                1030                1035                1040

Val Leu Arg Gln Phe Thr Thr Tyr Thr Pro Lys Ala Asp Phe Ala Trp
            1045                1050                1055

Gln His Ile Asp Gly Ser Glu Arg Ser Phe Gly Val Ser Val Tyr Ser
            1060                1065                1070

Ile Asp Ala Ala Asp Pro Asn Asp Ala Ile Val Gln Ala Ala Val Pro
     1075                1080                1085

Lys Gly Asn Asn Val Lys Ala Phe Ala Lys Asp Tyr Phe Thr Gly Glu
     1090                1095                1100

Thr Tyr Val Gly Glu Val Lys Asp Gly Val Ala Thr Phe His Ile His
1105                1110                1115                1120

Thr Ser Ile Asn Pro Asp Pro Gln Thr Gly Ile Asn Arg Arg Ala Leu
            1125                1130                1135

Leu Gln Gly Trp Val Glu Ile Asp Gly Pro Thr Tyr Asn Ala Lys Gln
            1140                1145                1150

Val Thr Asp Pro Thr Ala Ile Ser Asp Arg Asn Tyr Ile Gly Val Tyr
     1155                1160                1165

Tyr Lys Pro Asp Ala Ser Ser His Val Tyr Ser Asn Arg Asp Glu Leu
     1170                1175                1180

Gly Val Asp Asp Phe Thr Asp Glu Gln Ala Asp Val Ser Asp Phe Gly
1185                1190                1195                1200

Pro Ser Lys Phe Leu Tyr Pro Gly His Asn Ala Pro Ser Asp Gly Asn
            1205                1210                1215

Ala Asn Ile Ser Phe Asp Tyr Val Asn Asp Asn Ile Ser Thr Phe
            1220                1225                1230

Gly Gln Glu Ala Val Lys Ala Gly Tyr Tyr Asp Pro Ile Ala Lys Val
     1235                1240                1245

Phe Thr Ile Thr Gly His Val Asp Lys Asp Val Val Ser Leu Val Ala
     1250                1255                1260

Leu Gln Asp Asn Pro Asn Glu Asp Ala Pro Glu Asn Arg Val Ala Ile
1265                1270                1275                1280

Asp Lys Asp Gly Asn Phe Ile Ile Lys Phe His Met Asp Pro Ser
            1285                1290                1295

Thr Arg Gln Leu Thr Tyr Ile Tyr Lys Val Lys Asp Ser Ser Thr Asp
     1300                1305                1310

Lys Ile Asp Thr Val Lys Gly Ser Ile Thr Leu Ile Leu Asp Thr Val

```
                 1315                1320                1325

Leu Pro Thr Leu His Val Asp Gln Leu Asn Gly Ala Asp Asn Leu Thr
    1330                1335                1340

Ile Thr Thr Asn Asn Pro Thr Phe Lys Ile Ser Gly Asn Ala Asn Asp
1345                1350                1355                1360

Asp Leu Asp Asp Tyr Ser Val Tyr Ile Asn Gly Asp Asn Val Phe Thr
                1365                1370                1375

Gln Phe Asn Gly Ser Ser Phe Asn Tyr Ile Pro Gly Met Tyr Gly Asp
            1380                1385                1390

Pro Asn Gln Lys Thr Pro Asn Leu Tyr Gly Gly Tyr Asp Phe Glu Gln
        1395                1400                1405

Glu Val Asn Leu Asp Asp Glu Asn Gly Lys Pro Thr Thr His Ile Phe
    1410                1415                1420

Asn Ile Glu Leu Ile Asp Gln Val Gly Asn Lys Val Phe Lys Thr Leu
1425                1430                1435                1440

Thr Val Asn Tyr Asp Pro Asn Ala Thr Asn Ser Glu Asp Pro Ser Asn
                1445                1450                1455

Gly Thr Gly Asp Ser Gly Ile Glu Val Val Pro Thr Val Pro Arg Lys
            1460                1465                1470

Val Gln Pro Leu Ser Asp Asp Asn Ser Thr Asn Ile Asn Asp Lys Gln
        1475                1480                1485

Thr Leu Ser Thr Glu Leu Thr Ile Thr Leu Pro Arg Asn Ile Phe Ala
    1490                1495                1500

Phe Asp Tyr Gln Gly Lys Val Ala Arg Lys His Gly Lys Asp Ile Ile
1505                1510                1515                1520

Leu Lys Lys Gly Val Val Leu Tyr Asn Pro Lys Glu Val Asn Ile Arg
                1525                1530                1535

Lys His Lys Tyr Tyr Lys Val Ser Lys Asn Val Tyr Ile Lys Val Thr
            1540                1545                1550

Ser Thr Arg Val Asn Lys Lys Leu Lys Arg Leu Ile Leu Ile Lys Asn
        1555                1560                1565

Ser Tyr Val Tyr Asn Leu Asn Gly Lys Ala Asn Lys Val His Asn Lys
    1570                1575                1580

Arg Val Leu Leu Lys Arg Gly Leu Ala Val Asp Val Leu His Gly Gly
1585                1590                1595                1600

Lys Ile Thr Lys Val Gly Lys Tyr Asp Cys Tyr Gln Ile Gly Ile Asn
                1605                1610                1615

Gln Tyr Ile Lys Val Ala Asn Thr Ala Leu Lys
            1620                1625

<210> SEQ ID NO 23
<211> LENGTH: 1643
<212> TYPE: PRT
<213> ORGANISM: Streptococcus thermophilus

<400> SEQUENCE: 23

Met Pro Thr Ile Leu Cys Phe Asn Ile Phe Ile Gly Phe Ala Asn Asn
  1               5                  10                  15

Glu Gly Glu Lys Leu Gly Gly Lys Val Met Lys Lys Glu Thr Phe
             20                  25                  30

Ser Leu Arg Lys Tyr Lys Ile Gly Thr Val Ser Val Leu Leu Gly Ala
         35                  40                  45

Val Phe Leu Phe Ala Gly Ala Pro Ser Val Ala Ala Asp Glu Leu Thr
     50                  55                  60

Ser Leu Val Glu Thr Lys Val Glu Ala Thr Val Pro Asp Ala Ile Val
```

```
                65                  70                  75                  80
Ser Glu Ser Ala Ser Glu Ser Pro Val Ala Glu Glu Leu Val Asp Thr
                    85                  90                  95

Ser Val Glu Ala Thr Ser Thr Asp Val Thr Thr Asp Asn Glu Glu
                100                 105                 110

Glu Thr Leu Gly Ser Glu Ser Pro Val Glu Glu Leu Val Asp Thr
            115                 120                 125

Ser Val Glu Ala Thr Pro Thr Asp Val Thr Thr Asp Asn Val Glu
        130                 135                 140

Glu Thr Leu Gly Ser Glu Ala Leu Glu Asn Ile Thr Asn Thr Glu Val
145                 150                 155                 160

Glu Ala Thr Gln Pro Ala Val Glu Thr Pro Ala Ile Ser Glu Lys Lys
                165                 170                 175

Val Glu Glu Glu Glu Lys Leu Ser Val Ala Asp Glu Thr Thr Ala Ile
                180                 185                 190

Thr Asn Gln Glu Glu Ala Lys Pro Gln Asn Ile Asp Ser Asn Thr Ile
            195                 200                 205

Ile Thr Val Pro Lys Val Trp Asp Ser Gly Tyr Lys Gly Glu Gly Thr
        210                 215                 220

Val Val Ala Ile Ile Asp Ser Gly Leu Asp Val Asp His Asp Val Leu
225                 230                 235                 240

His Ile Ser Asp Leu Ser Thr Ala Lys Tyr Lys Ser Glu Lys Glu Ile
                245                 250                 255

Glu Ala Ala Lys Glu Val Ala Gly Ile Ser Tyr Gly Glu Trp Phe Asn
                260                 265                 270

Asp Lys Val Val Phe Gly Tyr Asn Tyr Val Asp Val Asn Thr Val Leu
            275                 280                 285

Lys Glu Glu Asp Lys Arg Ser His Gly Met His Val Thr Ser Ile Ala
        290                 295                 300

Thr Gly Asn Pro Thr Gln Pro Val Ala Gly Gln Leu Met Tyr Gly Val
305                 310                 315                 320

Ala Pro Glu Ala Gln Val Met Phe Met Arg Val Phe Ser Asp Leu Lys
                325                 330                 335

Ala Thr Thr Gly Ala Ala Leu Tyr Val Lys Ala Ile Glu Asp Ala Val
            340                 345                 350

Lys Leu Gly Ala Asp Ser Ile Asn Leu Ser Leu Gly Ala Asn Gly
        355                 360                 365

Ser Val Val Asn Met Asn Glu Asn Val Thr Ala Ala Ile Glu Ala Ala
        370                 375                 380

Arg Arg Ala Gly Val Ser Val Val Ile Ala Ala Gly Asn Asp Gly Thr
385                 390                 395                 400

Phe Gly Ser Gly His Ser Asn Pro Ser Ala Asp Tyr Pro Asp Tyr Gly
                405                 410                 415

Leu Val Gly Ala Pro Ser Thr Ala Arg Asp Ala Ile Ser Val Ala Ser
            420                 425                 430

Tyr Asn Asn Thr Thr Val Gly Ser Lys Val Ile Asn Ile Ile Gly Leu
        435                 440                 445

Glu Asn Asn Ala Asp Leu Asn Tyr Gly Lys Ser Ser Phe Asp Asn Pro
450                 455                 460

Glu Lys Ser Pro Val Pro Phe Glu Ile Gly Lys Glu Tyr Glu Tyr Val
465                 470                 475                 480

Tyr Ala Gly Ile Gly Gln Ala Ser Asp Phe Asp Gly Leu Asp Leu Thr
                485                 490                 495
```

-continued

Gly Lys Leu Ala Leu Ile Lys Arg Gly Thr Ile Ser Phe Ser Glu Lys
                500                 505                 510

Ile Ala Asn Ala Thr Ala Ala Gly Ala Val Gly Val Val Ile Phe Asn
            515                 520                 525

Ser Arg Pro Asp Glu Ala Asn Val Ser Met Gln Leu Asp Asp Thr Ala
        530                 535                 540

Ile Ala Ile Pro Ser Val Phe Ile Pro Leu Glu Phe Gly Glu Ala Leu
545                 550                 555                 560

Ala Ala Asn Ser Tyr Lys Ile Ala Phe Asn Asn Glu Thr Asp Ile Arg
                565                 570                 575

Pro Asn Pro Glu Ala Gly Leu Leu Ser Asp Phe Ser Ser Trp Gly Leu
            580                 585                 590

Ser Ala Asp Gly Glu Leu Lys Pro Asp Leu Ala Ala Pro Gly Gly Ala
        595                 600                 605

Ile Tyr Ala Ala Ile Asn Asp Asn Asp Tyr Ala Asn Met Gln Gly Thr
610                 615                 620

Ser Met Ala Ser Pro His Val Ala Gly Ala Ala Val Leu Val Lys Gln
625                 630                 635                 640

Tyr Leu Gln Ala Thr Tyr Pro Thr Lys Ser Pro Gln Glu Ile Glu Ala
                645                 650                 655

Leu Val Lys His Leu Leu Met Ser Thr Ala Lys Ala His Val Asn Lys
            660                 665                 670

Glu Thr Thr Ala Tyr Thr Ser Pro Arg Gln Gln Gly Ala Gly Ile Ile
        675                 680                 685

Asp Thr Ala Ala Ala Ile Ser Thr Gly Leu Tyr Leu Thr Gly Glu Asp
690                 695                 700

Gly Tyr Gly Ser Ile Thr Leu Gly Asn Val Glu Asp Thr Phe Ser Phe
705                 710                 715                 720

Thr Val Thr Leu His Asn Ile Thr Asn Glu Asp Lys Thr Leu Asn Tyr
                725                 730                 735

Ser Thr Gln Leu Thr Thr Asp Thr Val Gln Asn Gly Leu Ile Thr Leu
            740                 745                 750

Ala Pro Arg Leu Leu Ala Glu Ile Pro Gly Gly Lys Val Thr Val Gln
        755                 760                 765

Ala Asn Ser Ser Thr Thr Val Thr Ile Asn Val Asp Ala Ser Ser Phe
770                 775                 780

Ala Glu Glu Leu Thr Gly Leu Met Lys Asn Gly Tyr Tyr Leu Glu Gly
785                 790                 795                 800

Phe Val Arg Phe Thr Asp Val Ala Asp Gly Gly Asp Ile Val Ser Ile
                805                 810                 815

Pro Tyr Ile Gly Phe Arg Gly Glu Phe Gln Asn Leu Ala Val Leu Glu
            820                 825                 830

Glu Pro Ile Tyr Asn Leu Ile Ala Asp Gly Lys Gly Phe Tyr Phe
        835                 840                 845

Glu Pro Val Thr Ala Gln Pro Asp Ser Val Asp Ile Ser His His Tyr
850                 855                 860

Thr Gly Leu Val Thr Gly Ser Thr Glu Leu Ile Tyr Ser Thr Asp Lys
865                 870                 875                 880

Arg Ser Asp Phe Ala Ile Lys Lys Thr Leu Gly Thr Phe Lys Asn Glu
                885                 890                 895

Ala Gly Tyr Phe Val Leu Glu Leu Asp Glu Ser Gly Lys Pro His Leu
            900                 905                 910

Ala Ile Ser Pro Asn Gly Asp Asp Asn Gln Asp Ser Leu Ala Phe Lys
        915                 920                 925

```
Gly Val Phe Leu Arg Asn Tyr Thr Asp Leu Val Ala Ser Val Tyr Ala
    930                 935                 940

Ala Asp Asp Thr Glu Arg Thr Asn Pro Leu Trp Glu Ser Gln Pro Gln
945                 950                 955                 960

Ser Gly Asn Lys Asn Phe Tyr Ser Gly Asp Pro Lys Asn Pro Lys Ser
            965                 970                 975

Ser Ile Ile Tyr Pro Thr Glu Trp Asn Gly Thr Asp Ser Glu Gly Asn
        980                 985                 990

Ala Leu Ala Asp Gly Lys Tyr Gln Tyr Val Leu Thr Tyr Ser Ser Glu
    995                 1000                1005

Val Pro Gly Ala Ala Val Gln Thr Met Ile Phe Asp Val Ile Ile Asp
    1010                1015                1020

Arg Glu Ser Pro Val Ile Thr Thr Ala Thr Tyr Asp Glu Thr Asn Phe
1025                1030                1035                1040

Thr Phe Asn Pro Arg Pro Ala Ile Glu Lys Gly Glu Ser Gly Leu Tyr
            1045                1050                1055

Arg Glu Gln Val Phe Tyr Leu Val Ala Asp Ala Ser Gly Val Thr Thr
            1060                1065                1070

Ile Pro Ser Leu Leu Glu Asn Gly Asp Val Thr Val Ser Asp Asn Lys
        1075                1080                1085

Val Phe Val Ala Gln Asn Asp Asp Gly Ser Phe Thr Leu Pro Leu Asp
    1090                1095                1100

Leu Ala Asp Ile Ser Lys Phe Tyr Tyr Thr Val Glu Asp Tyr Ala Gly
1105                1110                1115                1120

Asn Ile Ser Tyr Glu Lys Val Glu Asn Leu Ile Ser Ile Gly Asn Glu
            1125                1130                1135

Lys Gly Leu Val Thr Val Asn Ile Leu Asp Lys Asp Thr Asn Ser Pro
            1140                1145                1150

Val Pro Ile Leu Phe Ser Tyr Ser Val Thr Asp Glu Thr Gly Lys Ile
        1155                1160                1165

Val Ala Glu Leu Pro Arg Tyr Ala Gly Asp Thr Ser Val Leu Lys Leu
    1170                1175                1180

Pro Phe Gly Thr Tyr Thr Phe Asp Leu Phe Leu Tyr Asp Thr Glu Trp
1185                1190                1195                1200

Ser Ser Leu Ala Gly Glu Thr Lys Ala Val Val Thr Ile Leu Glu Asp
            1205                1210                1215

Asn Ser Thr Ala Glu Val Asn Phe Tyr Val Thr Leu Lys Asp Lys Ala
            1220                1225                1230

Asn Leu Leu Ile Asp Ile Asp Ala Leu Leu Pro Ser Gly Ser Thr Ile
        1235                1240                1245

Gln Leu Val Thr Ala Asp Gly Gln Ala Ile Gln Leu Pro Asn Ala Lys
    1250                1255                1260

Tyr Ser Lys Thr Asp Tyr Gly Lys Phe Val Pro Val Gly Thr Tyr Thr
1265                1270                1275                1280

Ile Leu Pro Thr Leu Pro Glu Gly Tyr Glu Phe Leu Glu Glu Leu Asp
            1285                1290                1295

Val Ala Val Leu Ala Asn Gln Ser Asn Val Lys Lys Leu Thr Leu Ile
            1300                1305                1310

Asn Lys Val Ala Leu Lys Glu Leu Ile Ala Glu Leu Ala Gly Leu Glu
            1315                1320                1325

Glu Thr Ala Arg Tyr Tyr Asn Ala Ser Pro Glu Leu Gln Thr Ala Tyr
    1330                1335                1340

Ala Lys Ala Leu Glu Asp Ala Asn Ala Val Tyr Ala Asn Lys His Asn
```

```
                1345                1350                1355                1360
Gln Ala Gln Val Asp Ser Ala Leu Ala Ser Leu Val Ala Ala Arg Glu
            1365                1370                1375
Gln Leu Asn Gly Gln Ala Thr Asp Lys Glu Lys Leu Ile Ala Glu Val
        1380                1385                1390
Ser Asn Tyr Thr Pro Thr Gln Ala Asn Phe Ile Tyr Tyr Asn Ala Glu
        1395                1400                1405
Asn Thr Lys Gln Ile Ala Tyr Asp Thr Ala Val Arg Ser Ala Gln Leu
    1410                1415                1420
Val Leu Asn Gln Glu Asn Val Thr Gln Ala Val Val Asn Gln Ala Leu
1425                1430                1435                1440
Ala Asp Leu Leu Ala Ala Lys Ala Asn Leu Asp Gly Gln Lys Thr Asp
            1445                1450                1455
Ile Ser Ala Leu Arg Ser Ala Val Ser Val Ser Ser Val Leu Lys Ala
        1460                1465                1470
Thr Asp Ala Lys Tyr Leu Asn Ala Ser Glu Asn Val Lys Gln Ala Tyr
        1475                1480                1485
Asp Gln Ala Val Glu Ala Ala Lys Ala Ile Leu Val Asp Glu Ser Ala
    1490                1495                1500
Ser Gln Ala Ser Val Asp Gln Ala Leu Ala Val Leu Thr Ser Ala Gln
1505                1510                1515                1520
Ala Glu Leu Asp Gly Val Ala Thr Ser Thr Asn Asp Ala Lys Glu Pro
            1525                1530                1535
Ala Asn Thr Ala Thr Asp Lys Lys Asp Glu Gly Thr Val Thr Pro Pro
        1540                1545                1550
Pro Ile Asp Ser Glu Ile Val Asp Val Gln Ala Pro Pro Val Lys Asp
    1555                1560                1565
Thr Gly Asn Ser Glu His Val Pro Ile Gly Gln Lys Pro Asn Pro Gln
    1570                1575                1580
Pro Thr Leu Pro Arg Pro Val Thr Leu Gln Ala Ser Leu Ser Ser Pro
1585                1590                1595                1600
Asn Gln Glu Lys Gln Val Thr Gln Leu Pro Asn Thr Gly Glu Asn Asp
            1605                1610                1615
Thr Lys Tyr Tyr Leu Val Pro Gly Val Ile Ile Gly Leu Gly Thr Leu
        1620                1625                1630
Leu Val Ser Ile Arg Arg His Lys Glu Glu Val
        1635                1640

<210> SEQ ID NO 24
<211> LENGTH: 2179
<212> TYPE: PRT
<213> ORGANISM: Lactobacillus johnsonii

<400> SEQUENCE: 24

Met Lys Lys Arg Glu Lys Tyr Thr Trp Leu Leu Leu Ser Thr Ala
  1               5                  10                  15
Leu Ile Thr Ser Gly Gln Ile Leu Gly Gly Glu Gln Ile Ile Lys
            20                  25                  30
Ala Ser Val Glu Ser Gln Thr Asn Ser Val Lys Lys Ser Lys Thr Ala
        35                  40                  45
Val Glu His Ser Thr Thr Ala Leu Ser Arg Gln Ala Val Glu Ala Gln
    50                  55                  60
Leu Ala Ala Gln Gly Val Asn Phe Glu Arg Leu Thr Pro Glu Gln
65                  70                  75                  80
Gln Glu Val Tyr Val Asp Val Ile Val Gln Leu Glu Ala Leu Pro Ala
```

-continued

```
                85                  90                  95
Ser Glu Asn Gly Ser Ile Asp Ser Gln Thr Ala Ser Arg Ala Glu Ile
                100                 105                 110
Glu Gln Ala Ser Asn Lys Val Ile Ala Ala Gln Ser Gly Ile Lys Asp
                115                 120                 125
Glu Val Gln Lys Ile Thr Asn Gln Ala Ile Asp Lys Ser Tyr Gly Tyr
                130                 135                 140
Val Val Asn Gly Phe Ala Thr Lys Ala Lys Val Gly Asp Ile Lys Lys
145                 150                 155                 160
Leu Arg Glu Ile Lys Gly Val Lys Ser Val Thr Leu Ala Lys Val Tyr
                165                 170                 175
Phe Ala Ala Asp Thr Ser Ala Asn Asn Met Ala Asn Val Ser Thr Val
                180                 185                 190
Trp Ser Asn Tyr Gln Tyr Lys Gly Glu Gly Thr Val Ser Ile Ile
                195                 200                 205
Asp Thr Gly Ile Asp Pro Asn His Lys Asp Leu Arg Leu Ser Asp Glu
                210                 215                 220
Ser Lys Val Lys Leu Thr Ala Lys Asp Ile Asp Gly Phe Thr Glu Asn
225                 230                 235                 240
Ser Gly Tyr Gly Arg Tyr Phe Thr Ser Lys Val Pro Phe Gly His Asn
                245                 250                 255
Tyr Ser Asp Asn Asn Asp Ile Ile Thr Asp Asp Pro Lys Glu Gln
                260                 265                 270
His Gly Met His Val Ala Gly Ile Val Ala Ala Asn Gly Thr Gly Lys
                275                 280                 285
Asn Ser Ala Ser Ser Val Val Gly Val Ala Pro Glu Ala Gln Leu Leu
                290                 295                 300
Ala Met Lys Ala Phe Ser Asn Ser Asp Ser Ser Thr Thr Asp Ser
305                 310                 315                 320
Thr Ser Val Ile Gly Ala Val Asp Asp Ser Ala Lys Leu Gly Ala Asp
                325                 330                 335
Val Leu Asn Met Ser Leu Gly Ser Val Ser Gly Glu Gln Thr Glu Asp
                340                 345                 350
Asp Pro Glu Ile Ala Ala Val Glu Lys Ala Val Lys His Gly Thr Ala
                355                 360                 365
Ala Val Ile Ser Gly Thr Ser Arg Ser Ala Thr Thr Val Ala Ser Ala
                370                 375                 380
Glu Asn Thr Lys Val Thr Thr Asp Gly Met Thr Val Ser Thr Ala Asp
385                 390                 395                 400
Gly Lys Lys Ile Phe Gly Pro Ser Val Thr Gln Leu Ser Pro Asn Thr
                405                 410                 415
Ser His Asp Ala Phe Asp Ser Lys Lys Phe Tyr Ile Val Lys Asp Ala
                420                 425                 430
Ser Gly Lys Leu Gly Met Gly Thr Pro Ser Gln Tyr Thr Ala Asp Val
                435                 440                 445
Lys Gly Lys Val Ala Val Ser Arg Gly Glu Ile Thr Phe Thr Asp
450                 455                 460
Lys Gln Lys Tyr Ala Gln Ala Ala Gly Ala Ala Gly Leu Ile Ile Val
465                 470                 475                 480
Asn Asn Ala Gly Gly Asn Thr Pro Leu Thr Ser Val Leu Tyr Asn Glu
                485                 490                 495
Gly Phe Pro Thr Ala Gly Leu Ser Thr Asp Asp Gly Asn Lys Leu Val
                500                 505                 510
```

```
Ala Tyr Val Glu Ala His Pro Asp Glu Leu Leu Arg Val Asn Val Glu
        515                 520                 525

Val Gln Pro Leu Asn Asn Val Ile Arg Glu Glu Asp Leu Met Ser Ser
530                 535                 540

Phe Thr Ser Tyr Gly Pro Val Ser Asp Leu Ser Phe Lys Pro Asp Ile
545                 550                 555                 560

Thr Ala Pro Gly Gly Asn Ile Trp Ser Leu Gln Asn Asn Gly Tyr
                565                 570                 575

Ile Asn Met Ser Gly Thr Ser Met Ala Ser Pro Phe Ile Ala Gly Ser
                580                 585                 590

Gln Ala Leu Leu Val Gln Ala Met Asn Asp Lys Thr Gly Lys Phe Tyr
            595                 600                 605

Glu Thr Tyr Gln Lys Met Ser Gly Ser Glu Arg Ala Ala Leu Ile Lys
        610                 615                 620

Asn Ile Gln Met Asn Thr Ala Asn Ile Glu Val Asp Val Asp His Gly
625                 630                 635                 640

Ser Val Ile Glu Ser Pro Arg Arg Gln Gly Ala Gly Leu Val Asn Val
                645                 650                 655

Glu Ala Ala Ile Asn Ala Ile Leu His Asn Pro Ser Thr Val Ser Gly
            660                 665                 670

Ser Asn Gly Tyr Pro Gly Val Glu Leu Lys Asp Phe Gln Asp Arg Gln
        675                 680                 685

His Gln Phe Thr Ile Lys Phe Thr Asn Arg Thr Asn Lys Asp Ile Glu
    690                 695                 700

Tyr Gly Leu Asn Glu Asn Gly Lys Phe Ser Asp Val Tyr Thr Ser Glu
705                 710                 715                 720

Thr Asp Pro Lys Thr Gly Val Leu Phe Glu Lys Lys Ile Asp Gly Ala
                725                 730                 735

Ser Leu Thr Pro Ser Glu Lys Ile Val Val Pro Ala Asn Ser Thr Lys
            740                 745                 750

Glu Val Thr Ile Asn Leu Ser Leu Pro Asp Asn Phe Lys Glu Asn Gln
        755                 760                 765

Tyr Val Glu Gly Phe Met Ala Phe Thr Gly Ser Asp Asn Ser His Leu
    770                 775                 780

Lys Ile Pro Tyr Met Gly Phe Phe Gly Asp Trp Ala Ala Pro Ala Ile
785                 790                 795                 800

Phe Asp Gly Leu Asn Gly Leu Ala Phe Asn Pro Gly Asn Asn Asn Leu
                805                 810                 815

Gly Thr Ile Val Thr Ala Gly Asn Lys Asn Gly Ala Val Gly Tyr Ala
            820                 825                 830

Gly Leu Asn Gln Asp Glu Asp Gly Asn Tyr Arg Val Asp Pro Asp Ala
        835                 840                 845

Ile Ala Leu Ser Thr Ala Asp Gly Ala Ser Val Ser Trp Val Arg Pro
    850                 855                 860

Gln Tyr Phe Leu Phe Arg Asn Ala Asn Asp Val Lys Ala Glu Ile Leu
865                 870                 875                 880

Asn Gln Asp Gly Glu Val Ile Asn Thr Leu Val Ser Leu Ala His Val
                885                 890                 895

Thr Lys Ser Tyr Trp Ala Ala Ser Ser Gln Arg Tyr Ala Lys Phe Asn
            900                 905                 910

Tyr Ala Pro Ala Trp Asp Gly Thr Tyr Phe Asn Gln Gln Thr Asn Lys
        915                 920                 925

Thr Glu Lys Val Pro Asp Gly Thr Tyr Thr Tyr Arg Val Thr Gly Thr
    930                 935                 940
```

Val Asp Gly Thr Lys Lys Gln Gln His Tyr Asp Ile Lys Val Lys Val
945                 950                 955                 960

Asp Ser Val Lys Pro Glu Val Lys Asn Leu Lys Leu Gly Ser His Lys
        965                 970                 975

Asp Gln Thr Gly Lys Val Ser Tyr Val Leu Lys Ala Glu Ala Lys Asp
        980                 985                 990

Asn Phe Ser Gly Leu Asn Gly Gln Ala Asn Thr Tyr Val Asn Gly Glu
        995                 1000                1005

Leu Asn Arg Ser Val Ala Tyr Asp Ile Val Gly Ser Ser Asp Gly
    1010                1015                1020

Tyr Gln Lys Ile Glu Val Pro Leu Ser Asp Glu Gln Val Lys Thr Leu
1025                1030                1035                1040

Arg Ala Gly Lys Asn Asp Leu Ala Ile Ala Val Phe Asp Asn Ala Thr
            1045                1050                1055

Asn Ala Gly Thr Asn Ser Gly Thr Ser Asn Lys Pro Gly Glu Ile Asn
            1060                1065                1070

Phe Gly Leu Ile Ile Asp Asn Asn Leu Pro Gln Lys Ile Thr Thr Val
        1075                1080                1085

Ser Asp Gly Tyr Asp Met Thr Asp Ser Tyr Thr Ile Ser Gly Thr
    1090                1095                1100

Tyr Pro Glu Lys Val Tyr Gly Thr Tyr Thr Asp Lys Asp Gly Lys Glu
1105                1110                1115                1120

His Asp Leu Asn Ile Ser Tyr Asp Glu Ala Ser Glu Arg Phe Val Thr
            1125                1130                1135

Lys Leu Pro Leu Ser Val Ser Asp Tyr Asp Thr Asn Val Lys Phe Tyr
            1140                1145                1150

Ala Asp Glu Glu His Glu Thr Leu Ile Thr Gln Lys Arg Ile Asn Val
        1155                1160                1165

Ser Leu Val Pro Pro Lys Leu Glu Ser Leu Lys Val Asp Asp Gln Glu
    1170                1175                1180

Thr Tyr Thr Gly Asn Glu Glu Ala Lys Leu Ser Gln Thr Ser Glu Asp
1185                1190                1195                1200

Thr Val Glu Val Ser Gly Lys Val Ser Asp Thr Asp Lys Val Ala
        1205                1210                1215

Val Lys Val Ala Gly Lys Thr Tyr Ser Ala Lys Pro Thr Lys Glu His
        1220                1225                1230

Thr Phe Lys Val Lys Val Pro Val Ser Tyr Gly Glu Asn Thr Met Asn
        1235                1240                1245

Ile Val Leu Thr Asp Lys Asp Gly Asn Ser Ser Ser Val Lys Gln Ile
1250                1255                1260

Val Lys Ser Ser Asp Arg Gly Lys Thr Val Val Ser Ala Lys Asp Val
1265                1270                1275                1280

Thr Phe Asp Asn Gly Ile Lys Phe Gly Thr Thr Ser Val Asn Thr Glu
        1285                1290                1295

Thr Glu Asn Tyr Asp Pro Lys Thr Gly Lys Leu Thr Leu Thr Gly Lys
        1300                1305                1310

Val Asn Arg Pro Thr Thr Thr Val Arg Ile Gly Asp His Thr Val Lys
        1315                1320                1325

Val Lys Ala Asp Gly Thr Phe Lys Leu Val Leu Asp Leu Gly Lys His
        1330                1335                1340

Gly Ala Lys Val Phe Pro Val Leu Ile Gly Asp Thr Thr Val Asn Asp
1345                1350                1355                1360

Thr Val Gln Glu Arg Leu Thr Phe Tyr Val Asp Ser Asn Asn Pro Glu

-continued

Leu Thr Leu Asn Gln Glu Lys Asp Gln Ser Gly Tyr Val Pro Val Tyr
    1365                1370                1375
Thr Asn Lys Glu Glu Phe Lys Leu Gln Gly Thr Ile Ser Asp Asp Tyr
        1380                1385                1390
Pro Tyr Tyr Ser Leu Leu Ile Asn Asp Asn Val Asp Ala Asn Trp
    1395                1400                1405
Asp Asp Val Asp Tyr Asn Gly Asn Lys Asn Leu Lys Lys Ser Phe Ser
    1410                1415                1420
His Ser Val Lys Leu Lys Glu Gly Lys Asn Thr Phe Asn Val Val Val
1425                1430                1435                1440
Val Asp Asn Asn Asp Asn Arg Ser Glu Val Gln Thr Leu Val Val Tyr
        1445                1450                1455
Tyr Lys Lys Ala Gln Lys Leu Ala Ser Pro Gln Ile Thr Ala Thr Thr
    1460                1465                1470
Ala Ser Asp Lys Lys Ser Val Thr Val Thr Gly Lys Ala Lys Asp Gly
        1475                1480                1485
Asn Val Leu Tyr Ser Thr Asp Asn Gly Asn Lys Tyr Asn Val Leu Pro
1490                1495                1500
Glu Asp Gly Val Thr Val Lys Asn Asn Gly Lys Leu Leu Phe Lys Thr
    1505                1510                1515                1520
Val Asp Lys Tyr Gly Asn Glu Ser Glu Val Val Glu Tyr Asp Val Lys
        1525                1530                1535
Thr Ile Gly Lys Glu Glu Ser Thr Val Asp Lys Ser Val Ala Gln Ala
    1540                1545                1550
Arg Lys Asp Leu Arg Lys Lys Leu Asp Gln Ala Arg Ala Leu Gly Asn
    1555                1560                1565
Thr Gly Lys Tyr Thr His Glu Ser Ala Lys Lys Leu Ala Gln Ala Arg
1570                1575                1580
Gln Glu Ala Ser Lys Ala Leu Lys Asp Lys Asn Ala Thr Leu Gln Glu
    1585                1590                1595                1600
Leu Lys Gln Ala Ser Glu Gln Leu Glu Glu Ala Ile Lys Asn Leu Val
        1605                1610                1615
Glu Lys Pro Val Asp Gln Asn Lys Asp Lys Asp Lys Val Glu Asp Lys
    1620                1625                1630
Asp Ser Gln Val Asn Ala Leu Lys Glu Lys Leu Glu Glu Thr Val Lys
        1635                1640                1645
Ala Gly Glu Lys Phe Asp Lys Asp Lys Tyr Thr Asp Asp Ser Val Glu
1650                1655                1660
Lys Val Thr Lys Ala Leu Asp Glu Ala Lys Val Val Leu Ala Asn Lys
    1665                1670                1675                1680
Asp Ala Asn Ser Thr Asp Val Gln Asp Ala Ile Asp Ser Ile Val Asn
        1685                1690                1695
Ala Thr Lys Ser Leu Lys Glu Lys Gln Val Ser Pro Glu Lys Thr Thr
    1700                1705                1710
Gln Gln Glu Asp Thr Pro Lys Glu Asn Lys Asp Thr Glu Glu Val Leu
    1715                1720                1725
Ala Ala Lys Asn Ala Leu Lys Glu Lys Ala Asp Lys Leu Ser His Leu
1730                1735                1740
Asp Thr Thr Lys Tyr Thr Ser Glu Ser Ala Glu Asn Leu Ser Asn Ala
    1745                1750                1755                1760
Leu Lys Lys Val Asn Gln Val Leu Thr Asn Lys Asp Ala Asn Lys Ala
        1765                1770                1775

```
Gln Val Gln Glu Ala Leu Asp Ser Leu Ser Gln Ala Glu Lys Asp Leu
        1795                1800                1805

Val Glu Lys Thr Glu Ser Asn Lys Asp Val Glu Thr Ala Lys Glu Gln
    1810                1815                1820

Leu Arg Glu Glu Leu Asn Lys His Lys Asp Glu Asp Lys Ser Gln Tyr
1825                1830                1835                1840

Thr Asp Asp Ser Ala Lys Val Lys Asp Asn Ala Glu Lys Ile Ser Glu
                1845                1850                1855

Gly Val Leu Asp Ser Lys Asp Ala Gln Ala Asp Glu Val Asn Lys Ala
            1860                1865                1870

Lys Asp Ser Leu Val Glu Ala Glu Lys Gly Leu Val Lys Lys Glu Glu
        1875                1880                1885

Asn Lys Pro Ala Glu Ser Asp Thr Gln Glu Val Asp Lys Ala Arg Glu
    1890                1895                1900

Ala Leu Glu Gln Glu Val Asn Lys Asn Ala Asn Val Asn Leu Asp Gly
1905                1910                1915                1920

Tyr Thr Pro Glu Ser Gln Asp Lys Phe Lys Glu Ile Leu Asn Gly Val
                1925                1930                1935

Arg Asp Val Leu Asn Asp Lys Asn Ala Ser Ala Ser Leu Glu Lys
            1940                1945                1950

Ala Glu Lys Val Leu Glu Thr Ala Thr Gly Val Leu Thr Gln Val Glu
        1955                1960                1965

His Gln Val Glu Leu Pro Lys Val Glu Gln Pro Val Thr Pro Glu
    1970                1975                1980

Lys Lys Gln Thr Glu Gln Glu Glu Ala Lys Lys Ser Glu Ser Ser Ser
1985                1990                1995                2000

Val Ser Thr Ser Lys Asp Glu Val Lys Glu Pro Glu Glu Lys Lys Gln
                2005                2010                2015

Asp Ala His Ser Val Ser Asp Lys Gly Thr Gly Thr Ser Val Glu Lys
            2020                2025                2030

Lys Gly Gln Thr Pro Ala Asp Ala Leu Ser Gln Val Glu His Gln Ala
        2035                2040                2045

Glu Leu Ser Lys Asn Glu Gln Glu Glu Ala Lys Lys Ser Glu Ser His
    2050                2055                2060

Ser Ala Ser Thr Ser Lys Asp Glu Val Lys Glu Pro Glu Glu Lys Lys
2065                2070                2075                2080

Gln Asp Ala Glu Ser Val Ser Asp Lys Glu Ser Ser Thr Leu Val Gly
                2085                2090                2095

Lys Lys His Gln Val Ala Arg Ser Ala Gln Glu Ser Ser Lys Lys Asn
            2100                2105                2110

Ala Asp Asn Lys Val Pro Thr His Lys Asn Ser Asn Lys Ala Gln Asn
        2115                2120                2125

Thr Thr Asn Ser Ser Thr Arg Ser Thr Lys Ser Ser Asn Asn Lys Glu
    2130                2135                2140

Leu Pro Lys Thr Gly Glu Arg Glu Thr Phe Phe Gly Leu Leu Val Thr
2145                2150                2155                2160

Gly Ile Thr Ala Leu Phe Ala Ser Leu Gly Thr Val Leu Arg Ile Lys
                2165                2170                2175

Asn Lys Lys

<210> SEQ ID NO 25
<211> LENGTH: 1774
<212> TYPE: PRT
<213> ORGANISM: Lactobacillus sp.
```

-continued

<400> SEQUENCE: 25

```
Met Ala Glu Leu Ala Ala Leu Leu Ser Ala Ser Pro Leu Ala
 1               5                  10                  15

Gly Thr Phe Gln Ser Ala Ala Phe Val Gln Ala Ala Ser Gln Glu Thr
             20                  25                  30

Val Ser Pro Arg Ser Ala Ser Arg Ala Ala Leu Thr Lys Tyr Leu Gln
         35                  40                  45

Gln Glu Gln Arg Tyr Asn Ala Lys Lys Ser Tyr Ser Lys Phe Gln Glu
     50                  55                  60

Ala Ala Lys Glu Gln Arg Gln Ala Ser Gly Gln Ala Val Ser Lys Lys
 65                  70                  75                  80

Asn Glu Ser Ser Val Arg Val Ile Val Ser Leu Asn Lys Ser Ala Ala
                 85                  90                  95

Phe Asp His Thr Ser Lys Pro Thr Gly Ser Ala Ala Ser Val Lys Lys
             100                 105                 110

Ile Glu Gln Ala Ser Asp Gln Val Lys Asp Gly Gln Glu Lys Val Ile
         115                 120                 125

Lys Gln Val Glu Glu Ile Thr Gly Asn Lys Val Arg Arg Gln Phe Gly
     130                 135                 140

Tyr Leu Val Asn Ala Phe Ser Ile Asp Met Asp Leu Asp Asp Ile Asp
145                 150                 155                 160

Lys Val Lys Asp Leu Pro Gln Val Lys Asn Val Thr Pro Val Lys Val
                165                 170                 175

Tyr His Pro Thr Asp Glu Ser Ala Asp Gln Met Ala Gln Val Gln Asp
            180                 185                 190

Val Trp Gln Glu Gln Lys Leu Lys Gly Glu Gly Met Val Ile Ser Ile
        195                 200                 205

Ile Asp Thr Gly Ile Asp Ser Ser His Gln Asp Leu Lys Leu Asp Ser
210                 215                 220

Gly Val Ser Gly Tyr Asn Tyr Ala Asp Lys Asn Asp Gln Ile Val Asp
225                 230                 235                 240

Asn Gly Cys Gly Glu Met His Gly Gln His Val Ala Gly Ile Ala Gly
                245                 250                 255

Ala Asn Gly Gln Val Lys Gly Val Ala Pro Asp Ala Gln Leu Leu Ala
            260                 265                 270

Met Lys Val Phe Ser Asn Asn Ala Lys Asn Ser Gly Ala Tyr Asp Asp
        275                 280                 285

Asp Ile Ile Ser Ala Ile Glu Asp Ser Val Lys Leu Gly Ala Asp Val
    290                 295                 300

Ile Asn Met Ser Leu Gly Ser Val Ser Ser Asp Val Asp Pro Ser Asp
305                 310                 315                 320

Pro Gln Gln Gln Ala Val Ala Lys Ala Ser Glu Ala Gly Val Ile Asn
                325                 330                 335

Val Ile Ser Ala Gly Asn Ser Gly Val Ala Gly Ser Thr Ala Asp Gly
            340                 345                 350

Asn Pro Val Asn Asn Thr Gly Thr Ser Glu Leu Ser Thr Val Gly Thr
        355                 360                 365

Pro Gly Val Thr Pro Asp Ala Leu Thr Val Ala Ser Ala Glu Asn Ser
    370                 375                 380

Lys Val Thr Thr Asp Thr Val Lys Asp Glu Leu Gly Val Thr Phe
385                 390                 395                 400

Ser Ser Asn Ser Glu Leu Lys Gly Ala Ala Gln Val Thr Thr Gln Leu
                405                 410                 415
```

-continued

```
Glu Ser Asn Tyr Ser Val Leu Thr Lys Lys Leu Lys Leu Val Asp Met
            420                 425                 430

Gly Leu Gly Gly Ala Asp Asp Tyr Thr Ala Glu Lys Lys Ala Glu Val
        435                 440                 445

Lys Gly Gln Leu Ala Val Val Glu Arg Gly Ser Tyr Thr Phe Ser Ala
    450                 455                 460

Lys Val Ala Asn Ala Lys Ala Ala Gly Ala Ala Gly Ile Val Ile Tyr
465                 470                 475                 480

Asn Ser Glu Asp Asp Gly Leu Leu Ser Met Ser Leu Asp Asp Lys Thr
                485                 490                 495

Phe Pro Thr Leu Gly Met Ser Lys Ala Asp Gly Glu Val Leu Ala Lys
            500                 505                 510

Ala Ala Lys Glu Gly Lys Ser Ile Lys Leu Lys Phe Gly Thr Ala Leu
        515                 520                 525

Ile Asp Asn Ser Ser Ala Gly Lys Met Ser Asp Phe Thr Ser Trp Gly
    530                 535                 540

Pro Thr Pro Asp Leu Asp Phe Lys Pro Glu Ile Thr Ala Pro Gly Gly
545                 550                 555                 560

Lys Ile Tyr Ser Leu Ala Asn Asp Asn Lys Tyr Gln Gln Met Ser Gly
                565                 570                 575

Thr Ser Met Ala Ser Pro Phe Val Ala Gly Ser Glu Ala Leu Ile Leu
            580                 585                 590

Gln Gly Ile Lys Lys Gln Gly Leu Asn Leu Ser Gly Glu Glu Leu Val
        595                 600                 605

Gln Phe Ala Lys Asn Ser Ala Met Asn Thr Ser His Pro Val Tyr Asp
    610                 615                 620

Thr Glu His Thr Lys Glu Ile Ile Ser Pro Arg Arg Gln Gly Ser Gly
625                 630                 635                 640

Glu Ile Asn Val Lys Asp Ala Ile Asn Asn Thr Val Glu Val Lys Ala
                645                 650                 655

Ala Asn Gly Asn Gly Ala Ala Ala Leu Lys Glu Ile Gly Arg Gln Thr
            660                 665                 670

Thr Phe Lys Val Thr Leu Thr Asn His Gly Lys Lys Ala Gln Thr Tyr
        675                 680                 685

Ala Val Asp Asn Tyr Gly Gly Pro Tyr Thr Gln Ala Thr Glu Ala Lys
    690                 695                 700

Ser Gly Glu Ile Tyr Asp Thr Lys Ile Val Lys Gly Gln Leu Thr Thr
705                 710                 715                 720

Glu Thr Pro Lys Val Thr Val Gln Pro Gly Glu Ser Val Asp Val Ser
                725                 730                 735

Phe Thr Leu Thr Leu Pro Tyr Ser Phe Gln Arg Gln Asn Phe Val Glu
            740                 745                 750

Gly Tyr Val Gly Phe Glu Ala Glu Asp Gln Ala Thr Pro Asn Leu Val
        755                 760                 765

Leu Pro Tyr Met Gly Phe Phe Gly Ser Tyr Ser Gln Ala Ser Val Ser
    770                 775                 780

Ala Pro Met Leu Tyr Glu Gly Gly Asn Ser Asn Leu Ile Asn Thr Ile
785                 790                 795                 800

His Ser Leu Val Gly Val Met Phe Ser Asn Asn Asn Asp Ile Leu Gly
                805                 810                 815

His Thr Gly Tyr Glu Gly Asp Asp Tyr Ser Lys Tyr Thr Asp Pro Asp
            820                 825                 830

Leu Ile Ala Ile Ser Pro Asn Gly Asp Gly Ser Arg Asp Tyr Ala Tyr
        835                 840                 845
```

```
Pro Val Leu Phe Phe Asp Arg Asn Tyr Lys Glu Tyr Thr Glu Thr Ile
    850                 855                 860

Thr Asp Ala Gln Gly Asn Lys Val Lys Ser Leu Gly Val Gly Lys Glu
865                 870                 875                 880

Gly Thr Lys Asp Tyr Tyr Ser Ser Ser Gly Glu Trp Thr Thr His
                    885                 890                 895

Ser Leu Asp Lys Trp Asp Gly Thr Asp Ala Asp Gly Gln Val Val Lys
                900                 905                 910

Asp Gly Gln Tyr Ile Tyr Lys Val Glu Phe Thr Pro Ala Ile Gly Gly
            915                 920                 925

Ser Lys Gln Glu Leu Asn Ile Pro Val Lys Val Asp Thr Gln Ala Pro
    930                 935                 940

Glu Val Ser Asp Leu Gln Val Thr Lys Asp Gly Lys Leu Arg Leu Lys
945                 950                 955                 960

Ala Lys Asp Ser Gly Ser Gly Leu Asp Met Thr Met Phe Val Ala Ala
                    965                 970                 975

Val Asn Gly Glu Glu Gln Lys Leu Ala Leu Ala Pro Val Lys Gly Glu
                980                 985                 990

Ser Asn Val Tyr Glu Ser Thr Ser Ala Leu Thr Gly Leu Lys Asp Gly
            995                 1000                1005

Lys Asn Gln Val Glu Thr Val Leu Ala Asp Tyr Ala Gly Asn Val Gly
    1010                1015                1020

Tyr Ala Ala Thr Phe Ser Ser Gln Asn Asn Asp Ala Asp Asn Lys Leu
1025                1030                1035                1040

Leu Leu Phe Asn Leu Ala Asp Gly Gln Lys Ile Thr Ser Gln Ser Pro
                    1045                1050                1055

Ala Tyr Asp Gln Glu Lys Glu Thr Tyr Thr Val Thr Gly Thr Tyr Lys
                1060                1065                1070

Lys Asn Ala Lys Leu Lys Phe Asn Asp Val Glu Ala Glu Ser Asp Lys
            1075                1080                1085

Asn Gly Tyr Phe Glu Val Lys Leu Pro Val Lys Asp Gly Gln Asn Gln
    1090                1095                1100

Leu Leu Ile Lys Asp Gly Asp Gln Ile Leu Glu Ala Val Asn Phe Thr
1105                1110                1115                1120

Val Lys Ala Glu Gly Pro Lys Val Ser Val Asp Glu Glu Arg Ser Gly
                    1125                1130                1135

Arg Ile Leu Ala Lys Asp Asp Ser Tyr Thr Leu Ser Gly Thr Val Ser
                1140                1145                1150

Gly Leu Gly Glu Ser Gly Lys Leu Glu Leu Thr Asn Leu Ser Asp Lys
            1155                1160                1165

Ser Lys Thr Asn Lys Leu Thr Val Asp Gln Asp Gly Lys Phe Ser Gln
    1170                1175                1180

Lys Val Asp Leu Asn Tyr Gly Asp Asn Pro Phe Glu Leu Thr Ala Thr
1185                1190                1195                1200

Asp Ala Asp Gly Asn Val Thr Lys Lys Asp Val Thr Ile Phe Thr Ala
                    1205                1210                1215

Arg Ser Tyr Thr Tyr Asn Lys Asp Met Leu Thr Phe Asp Asn Ile Ala
                1220                1225                1230

Ser Asp Leu Thr Val Ile Gly Lys Thr Pro Asp Tyr Asp Glu Lys
            1235                1240                1245

Asp His Ser Phe Thr Val Thr Gly Lys Leu Ala Tyr Pro Val Ala Arg
    1250                1255                1260

Phe Gln Leu Asn Gly Asp Asp Val Lys Tyr Asp Pro Asp Thr Leu Lys
```

```
                 1265                1270                1275                1280
Phe Ser Tyr Thr Ile Lys Asp Leu Lys Asn Gly Asn His Ser Leu Thr
                 1285                1290                1295
Ala Leu Val Gln Asp Pro Arg Leu Asn Asp Gly Lys Pro Val Val Glu
         1300                1305                1310
Trp Gly Tyr Lys Leu Trp Val Asp Leu Ala Ala Pro Ser Leu Gln Leu
         1315                1320                1325
Glu Gly Met Ser Leu Gly Glu Asp Gly Gln Leu Ala Val Tyr Thr Asn
         1330                1335                1340
Lys Asp Val Tyr Asp Leu Lys Ala Thr Ile Asn Asp Asn Leu Ser Gly
1345                1350                1355                1360
Tyr Ser Leu Gln Val Gly Ser Asp Thr Ala Tyr Gln Asp Lys Thr Tyr
         1365                1370                1375
Lys Val Phe Asn Glu Asp Phe Phe Lys Asn Arg Asp Ala Val Lys Val
         1380                1385                1390
Ser Tyr Pro Ile Lys Ala Glu Lys Asp Gly Phe Arg Lys Val Lys Val
         1395                1400                1405
Thr Leu Thr Asp Gly Ser Asp Asn Lys Thr Glu Gln Asp Phe Ile Leu
         1410                1415                1420
Tyr Asn His Gln Ala Asp Leu Glu Ala Pro Glu Val Ser Ala Ser Glu
1425                1430                1435                1440
Ser Lys Lys Thr Asn Gln Ala Val Gln Leu Lys Val Gly Asn Leu Ser
                 1445                1450                1455
Asp Val Gln Lys Ser Ala Gly Lys Phe Lys Ala Ala Asp Leu Tyr Tyr
         1460                1465                1470
Ser Val Asp Gly Lys Thr Trp Thr Lys Leu Asp Lys Asp Thr Val Gln
         1475                1480                1485
Val Ala Glu Asn Gly Lys Val Glu Phe Lys Tyr Gln Asp Val Tyr Gly
         1490                1495                1500
Asn Glu Ser Lys Val Thr Thr Tyr Glu Val Lys Asn Ile Val Lys Glu
1505                1510                1515                1520
Val Ala Ala Gln Pro Glu Leu Lys Leu Thr Pro Asp Gly Glu Gly Lys
                 1525                1530                1535
Val Lys Ala Val Leu Ala Phe Asp Lys Lys Asp Val Asp Lys Asp Phe
         1540                1545                1550
Asn His Ile Lys Tyr Ser Leu Asp Gly Gly Lys Ser Trp Thr Asp Tyr
         1555                1560                1565
Lys Asp Ala Phe Thr Leu Thr His Asn Gly Thr Val Glu Phe Lys Ser
         1570                1575                1580
Tyr Asp Asp Ala Gly Asn Glu Gly Gln Val Tyr Thr Ser Val Val Lys
1585                1590                1595                1600
Val Glu Arg Lys Leu Pro Ala Pro Asp Leu Thr Gly Thr Val Glu Ala
         1605                1610                1615
Asp Lys Ser Val Glu Val Lys Ala Gly Asn Ser Ser Ala Lys Lys Thr
         1620                1625                1630
Ser Ala Lys Lys Asn Lys Lys Ala Ser Lys Ala Ser Lys Lys Thr
         1635                1640                1645
Val Lys Lys Thr Lys Thr Tyr Lys Lys Val Lys Leu Thr Lys Leu Thr
         1650                1655                1660
Lys Val Tyr Asn Lys Lys Gly Lys Val Val Gly Lys Leu Lys Lys
1665                1670                1675                1680
Thr Ser Ile Lys Leu Leu Ser Lys Gln Lys Leu His Gly Lys Tyr
         1685                1690                1695
```

```
Tyr Tyr Arg Val Gly Lys Asn Arg Tyr Ile Leu Ala Ser Asn Leu Pro
        1700                1705                1710

Lys Lys Thr Lys Lys Val Lys Gln Val Arg Ala Arg Lys Asn Ala Lys
        1715                1720                1725

Val Tyr Asn Lys Gly Lys Val Val Gly His Leu Lys Lys Lys Gln
    1730                1735                1740

Lys Val Lys Leu Leu Ser Lys Lys Gln Lys Leu His Gly Lys Tyr Tyr
1745                1750                1755                1760

Tyr Arg Ile Gly Lys Asn Arg Tyr Val Asn Ala Asn Val Leu
        1765                1770

<210> SEQ ID NO 26
<211> LENGTH: 485
<212> TYPE: PRT
<213> ORGANISM: Lactobacillus acidophilus

<400> SEQUENCE: 26

Met Val Glu Asn Lys Trp Leu His Ala Arg Lys Met Glu Val Arg Met
1               5                   10                  15

Leu Ile Ile Glu Ala Ile Tyr Val Phe Ser Met Phe Leu Ser Leu Val
            20                  25                  30

Phe Tyr Phe Pro Leu Phe Val Ile Glu Phe Lys Ile Ala Ile Ala Phe
        35                  40                  45

Thr Phe Leu Val Met Ile Gly Glu Leu Phe Glu Ile Lys Phe Lys Asn
    50                  55                  60

Glu Glu Ser Lys Asp Arg Ile Asp Ile Lys Glu His Gly Leu Met Lys
65                  70                  75                  80

Pro Cys Phe Phe His Lys Glu Glu Lys Arg Val Lys Ala Lys Ser Trp
                85                  90                  95

Asn Trp Asn Met Ile Leu Asn Ile Gln Leu Ile Ile Asn Ile Leu Ile
            100                 105                 110

Ala Gly Tyr Leu Leu Val Arg Glu Asn Lys Asn Leu Asp Ile Gln Ile
        115                 120                 125

Ile Phe Gly Ile Ile Leu Leu Tyr Ile Ile Ala Arg Leu Phe Ile
    130                 135                 140

Lys Asn Gln Tyr Ile Glu Lys Phe Asn Leu Val Leu Glu Ile Cys
145                 150                 155                 160

Leu Pro Ile Leu Leu Thr Tyr Tyr Leu Asn Trp Leu Val Ile Ser Leu
                165                 170                 175

Val His Phe Leu Pro Ala Ile Lys Leu Glu Ile Thr Ile Tyr Leu
            180                 185                 190

Val Val Ile Leu Leu Tyr Leu Leu Pro Thr Ser Val Val Ala Phe Gly
        195                 200                 205

Lys Ile His Asn Gly Tyr Leu Arg Ile Ala Ala Ser Ile Tyr Leu Phe
    210                 215                 220

Leu Val Phe Leu Ser Ser Ile Asn Ser Ser Leu Ser Val Asn Val Asp
225                 230                 235                 240

Phe Ile Asp Asn Leu Leu Lys Val Asn Val Ser Gly Met Ala Phe
                245                 250                 255

Leu Ile Leu Thr Pro Phe Leu Leu Arg Gln Trp Gly Phe Lys Phe Arg
            260                 265                 270

Met Asn Val Phe Pro Arg Lys Gln Glu Asn Phe Gln Leu Leu Val Leu
        275                 280                 285

Ile Leu Leu Val Leu Phe Ala Ala Trp Leu Thr Phe Phe Asn Thr Tyr
    290                 295                 300
```

```
Val Tyr Ile Ala Thr Val Pro Glu Gln Leu Phe Phe Asn Trp Asp Leu
305                 310                 315                 320

Ser Ile Leu Ala Pro Thr Gln Trp Thr Val Leu Arg Ser Ala Gly Ala
                325                 330                 335

Ala Ile Phe Glu Glu Thr Glu Arg Tyr Leu Ile Leu Ile Leu Leu Leu
            340                 345                 350

Tyr Ile Ala Arg Asn Ser Arg Phe Gln Ile Gln Ile Ala Ile Phe Phe
        355                 360                 365

Ser Ala Val Gln Phe Gly Leu Leu His Met Thr His Phe Leu Asp Ala
    370                 375                 380

Asp Ala Asn Val Ser Ser Ile Phe Tyr Glu Val Leu Tyr Thr Phe Gly
385                 390                 395                 400

Tyr Gly Cys Phe Leu Ala Val Leu Tyr Leu Tyr Ser Gly Gln Ile Trp
                405                 410                 415

Leu Ser Met Leu Ser His Phe Thr Leu Asp Leu Val Ser Tyr Ser Val
                420                 425                 430

Gly Asn Gly Gly Val Gly Phe Leu Ser Leu Tyr Gly Asn Val Glu Gly
            435                 440                 445

Ile Gly Ala Ala Leu Val Leu Ala Val Asn Leu Leu Val Val Phe Leu
    450                 455                 460

Met Leu Trp Gly Lys Arg Lys Ile Val Met Gln Asn Asn Ala Arg Ile
465                 470                 475                 480

Leu Ile Glu Arg Ile
                485

<210> SEQ ID NO 27
<211> LENGTH: 407
<212> TYPE: PRT
<213> ORGANISM: Lactococcus lactis

<400> SEQUENCE: 27

Met Ala Lys Ala Asn Ile Gly Lys Leu Leu Thr Gly Val Val Gly
  1               5                  10                  15

Gly Ala Ile Ala Leu Gly Gly Ser Ala Ile Tyr Gln Ser Thr Thr Asn
            20                  25                  30

Gln Leu Gly Asn Ala Asn Arg Ser Asn Thr Thr Ser Thr Lys Val Ser
        35                  40                  45

Asn Val Ser Val Asn Val Asn Thr Asp Val Thr Ser Ala Ile Lys Lys
    50                  55                  60

Val Ser Asn Ser Val Val Ser Val Met Asn Tyr Gln Lys Gln Asn Ser
65                  70                  75                  80

Gln Ser Asp Phe Ser Ser Ile Phe Gly Gly Asn Ser Gly Ser Ser Ser
                85                  90                  95

Ala Asn Asp Gly Leu Gln Leu Ser Ser Glu Gly Ser Gly Val Ile Tyr
            100                 105                 110

Lys Lys Ser Gly Gly Asp Ala Tyr Val Val Thr Asn Tyr His Val Ile
        115                 120                 125

Ala Gly Asn Ser Ser Leu Asp Val Leu Leu Ser Gly Gly Gln Lys Val
    130                 135                 140

Lys Ala Thr Val Val Gly Tyr Asp Glu Tyr Thr Asp Leu Ala Val Leu
145                 150                 155                 160

Lys Ile Ser Ser Asp His Val Lys Asp Val Ala Thr Phe Ala Asp Ser
                165                 170                 175

Ser Lys Leu Thr Ile Gly Glu Pro Ala Ile Ala Val Gly Ser Pro Leu
            180                 185                 190
```

```
Gly Ser Gln Phe Ala Asn Thr Ala Thr Glu Gly Ile Leu Ser Ala Thr
            195                 200                 205

Ser Arg Gln Val Thr Leu Thr Gln Glu Asn Gly Gln Thr Thr Ser Ile
210                 215                 220

Asn Ala Ile Gln Thr Asp Ala Ala Ile Asn Pro Gly Asn Ser Gly Gly
225                 230                 235                 240

Ala Leu Ile Asn Ile Glu Gly Gln Val Ile Gly Ile Thr Gln Ser Lys
            245                 250                 255

Ile Thr Thr Thr Glu Asp Gly Ser Thr Ser Val Glu Gly Leu Gly Phe
            260                 265                 270

Ala Ile Pro Ser Asn Asp Val Val Asn Ile Ile Asn Lys Leu Glu Thr
            275                 280                 285

Asp Gly Lys Ile Ser Arg Pro Ala Leu Gly Ile Arg Met Val Asp Leu
290                 295                 300

Ser Gln Leu Ser Thr Asn Asp Ser Ser Gln Leu Lys Leu Pro Ser Ser
305                 310                 315                 320

Val Thr Gly Gly Val Val Tyr Ser Val Gln Ala Gly Leu Pro Ala
            325                 330                 335

Ala Thr Ala Gly Leu Lys Ala Gly Asp Val Ile Thr Lys Val Gly Asp
            340                 345                 350

Thr Ala Val Thr Ser Ser Thr Asp Leu Gln Ser Ala Leu Tyr Ser His
            355                 360                 365

Asn Ile Asn Asp Thr Val Lys Val Thr Tyr Tyr Arg Asp Gly Lys Ser
370                 375                 380

Ala Thr Ala Asn Val Lys Leu Ser Lys Ser Thr Ser Asp Leu Glu Thr
385                 390                 395                 400

Asn Ser Pro Ser Ser Asn
            405

<210> SEQ ID NO 28
<211> LENGTH: 409
<212> TYPE: PRT
<213> ORGANISM: Lactococcus lactis

<400> SEQUENCE: 28

Met Ala Lys Ala Asn Ile Gly Lys Leu Leu Leu Thr Gly Val Val Gly
1               5                   10                  15

Gly Ala Ile Ala Leu Gly Gly Ser Ala Ile Tyr Gln Ser Thr Thr Asn
            20                  25                  30

Gln Ser Ala Asn Asn Ser Arg Ser Asn Thr Thr Ser Thr Lys Val Ser
            35                  40                  45

Asn Val Ser Val Asn Val Asn Thr Asp Val Thr Ser Ala Ile Lys Lys
    50                  55                  60

Val Ser Asn Ser Val Val Ser Val Met Asn Tyr Gln Lys Asp Asn Ser
65                  70                  75                  80

Gln Ser Ser Asp Phe Ser Ser Ile Phe Gly Gly Asn Ser Gly Ser Ser
            85                  90                  95

Ser Ser Thr Asp Gly Leu Gln Leu Ser Ser Glu Gly Ser Gly Val Ile
            100                 105                 110

Tyr Lys Lys Ser Gly Gly Asp Ala Tyr Val Val Thr Asn Tyr His Val
            115                 120                 125

Ile Ala Gly Asn Ser Ser Leu Asp Val Leu Leu Ser Gly Gly Gln Lys
            130                 135                 140

Val Lys Ala Ser Val Val Gly Tyr Asp Glu Tyr Thr Asp Leu Ala Val
145                 150                 155                 160
```

-continued

Leu Lys Ile Ser Ser Glu His Val Lys Asp Val Ala Thr Phe Ala Asp
            165                 170                 175

Ser Ser Lys Leu Thr Ile Gly Glu Pro Ala Ile Ala Val Gly Ser Pro
        180                 185                 190

Leu Gly Ser Gln Phe Ala Asn Thr Ala Thr Glu Gly Ile Leu Ser Ala
    195                 200                 205

Thr Ser Arg Gln Val Thr Leu Thr Gln Glu Asn Gly Gln Thr Thr Asn
210                 215                 220

Ile Asn Ala Ile Gln Thr Asp Ala Ala Ile Asn Pro Gly Asn Ser Gly
225                 230                 235                 240

Gly Ala Leu Ile Asn Ile Glu Gly Gln Val Ile Gly Ile Thr Gln Ser
                245                 250                 255

Lys Ile Thr Thr Thr Glu Asp Gly Ser Thr Ser Val Glu Gly Leu Gly
            260                 265                 270

Phe Ala Ile Pro Ser Asn Asp Val Val Asn Ile Ile Asn Lys Leu Glu
        275                 280                 285

Ala Asp Gly Lys Ile Ser Arg Pro Ala Leu Gly Ile Arg Met Val Asp
    290                 295                 300

Leu Ser Gln Leu Ser Thr Asn Asp Ser Ser Gln Leu Lys Leu Pro Ser
305                 310                 315                 320

Ser Val Thr Gly Gly Val Val Val Tyr Ser Val Gln Ser Gly Leu Pro
                325                 330                 335

Ala Ala Ser Ala Gly Leu Lys Ala Gly Asp Val Ile Thr Lys Val Gly
            340                 345                 350

Asp Thr Ala Val Thr Ser Ser Thr Asp Leu Gln Ser Ala Leu Tyr Ser
        355                 360                 365

His Asn Ile Asn Asp Thr Val Lys Val Thr Tyr Tyr Arg Asp Gly Lys
    370                 375                 380

Ser Asn Thr Ala Asp Val Lys Leu Ser Lys Thr Ser Asp Leu Glu
385                 390                 395                 400

Thr Ser Ser Pro Ser Ser Ser Asn Tyr
                405

<210> SEQ ID NO 29
<211> LENGTH: 402
<212> TYPE: PRT
<213> ORGANISM: Streptococcus mutans

<400> SEQUENCE: 29

Met Asn Asn Thr Lys Ser His Pro Phe Leu Lys Trp Phe Ile Pro Phe
1               5                   10                  15

Leu Val Ile Phe Leu Thr Phe Ile Leu Gly Val Ile Ser Thr Leu Thr
            20                  25                  30

Phe Asn Trp Ile Thr Gly Asn Lys Ser Phe Ser Asn Asn Gly Lys Thr
        35                  40                  45

Thr Val Ser Asn Val Ile Tyr Asp Thr Lys Ser Asn Thr Thr Lys Ala
    50                  55                  60

Val Lys Asn Val Lys Asn Thr Val Val Ser Val Ile Asn Tyr Gln Lys
65                  70                  75                  80

Thr Asp Asn Ser Tyr Tyr Asn Tyr Asp Ser Gly Ser Gln Glu Lys Asn
                85                  90                  95

Lys Ser Glu Asp Gly Leu Gly Val Tyr Gly Glu Gly Ser Gly Val Ile
            100                 105                 110

Tyr Lys Lys Asp Gly Asp Ser Ala Tyr Leu Val Thr Asn Asn His Val
        115                 120                 125

```
Val Lys Asp Ala Glu Lys Leu Glu Ile Met Met Ala Asn Gly Lys Lys
    130             135                 140

Val Val Gly Lys Leu Val Gly Ser Asp Thr Tyr Ser Asp Leu Ala Val
145             150                 155                 160

Ile Lys Ile Ser Ser Lys Tyr Val Thr Thr Val Ala Glu Phe Ala Asn
                165                 170                 175

Ser Asp Lys Ile Lys Val Gly Glu Pro Ala Ile Ala Ile Gly Ser Pro
            180                 185                 190

Leu Gly Ser Asp Tyr Ala Asn Ser Val Thr Glu Gly Ile Val Ser Ser
        195                 200                 205

Leu Ser Arg Thr Val Thr Ser Gln Asn Glu Asn Gly Thr Ile Ser
    210                 215                 220

Thr Asn Ala Ile Gln Thr Asp Ala Ala Ile Asn Pro Gly Asn Ser Gly
225                 230                 235                 240

Gly Ala Leu Ile Asn Ile Lys Gly Gln Val Ile Gly Ile Asn Ser Ser
                245                 250                 255

Lys Ile Ala Ser Ser Asn Asn Ser Asn Ser Gly Val Ala Val Glu Gly
            260                 265                 270

Met Gly Phe Ala Ile Pro Ser Asn Asp Val Val Ser Ile Ile Asn Gln
        275                 280                 285

Leu Glu Glu Asn Gly Glu Val Val Arg Pro Ala Leu Gly Ile Ser Met
    290                 295                 300

Ala Asn Leu Ser Glu Ala Ser Thr Ser Gly Arg Asp Thr Leu Lys Ile
305                 310                 315                 320

Pro Ser Asp Val Thr Ser Gly Ile Val Val Leu Ser Thr Gln Ser Gly
                325                 330                 335

Met Pro Ala Asp Gly Lys Leu Lys Lys Tyr Asp Val Ile Thr Glu Ile
            340                 345                 350

Asp Gly Lys Lys Val Ala Ser Ile Ser Asp Leu Gln Ser Ile Leu Tyr
        355                 360                 365

Lys His Lys Lys Gly Asp Lys Ile Lys Leu Thr Phe Tyr Arg Glu Lys
    370                 375                 380

Asp Lys Gln Thr Val Glu Ile Gln Leu Thr Lys Thr Ser Gln Asp Leu
385                 390                 395                 400

Asn His

<210> SEQ ID NO 30
<211> LENGTH: 413
<212> TYPE: PRT
<213> ORGANISM: Lactobacillus helveticus

<400> SEQUENCE: 30

Met Val Glu Asn Gln Asn Asn Gln Asn Gln Pro Arg Lys Lys Ser
  1               5                  10                  15

Gly Asn Lys Ile Ile Ala Thr Ala Ala Ile Phe Gly Val Val Gly Gly
                20                  25                  30

Leu Val Gly Gly Gly Val Ser Tyr Tyr Ala Met Asp Gln Met Asn Asn
        35                  40                  45

Gly Gln Gly Asn Gly Ala Ala Gln Ile Ser Ile Ser Ser Ser Ser Ser
    50                  55                  60

Lys Val Ser Glu Lys Ser Ala Lys Asn Gly Thr Met Thr Ala Ala
65                  70                  75                  80

Tyr Asn Asp Val Lys Gly Ala Val Val Ser Val Ile Asn Leu Lys Arg
                85                  90                  95

Gln Ser Ala Ser Ser Gly Thr Asp Ser Leu Tyr Asn Ser Leu Phe Gly
```

```
                      100                 105                 110
Asp Asp Ser Asp Ser Ser Ser Lys Asn Gly Lys Leu Glu Thr Tyr
            115                 120                 125
Ser Glu Gly Ser Gly Val Val Tyr Met Lys Ser Asn Gly Lys Gly Tyr
        130                 135                 140
Ile Val Thr Asn Asn His Val Ile Ser Gly Ser Asp Ala Val Gln Val
145                 150                 155                 160
Leu Leu Ala Asn Gly Lys Thr Val Asn Ala Lys Val Val Gly Lys Asp
                165                 170                 175
Ser Thr Thr Asp Leu Ala Val Leu Ser Ile Asp Ala Lys Tyr Val Thr
            180                 185                 190
Gln Thr Ala Gln Phe Gly Asp Ser Lys His Leu Glu Ala Gly Gln Thr
                195                 200                 205
Val Ile Ala Val Gly Ser Pro Leu Gly Ser Glu Tyr Ala Ser Thr Val
        210                 215                 220
Thr Gln Gly Ile Ile Ser Ala Pro Ala Arg Thr Ile Ser Thr Ser Ser
225                 230                 235                 240
Gly Asn Gln Gln Thr Val Ile Gln Thr Asp Ala Ala Ile Asn Pro Gly
                245                 250                 255
Asn Ser Gly Gly Ala Leu Val Asn Ser Ala Gly Gln Val Ile Gly Ile
            260                 265                 270
Asn Ser Met Lys Leu Ala Gln Ser Ser Asp Gly Thr Ser Val Glu Gly
                275                 280                 285
Met Ala Phe Ala Ile Pro Ser Asn Glu Val Val Thr Ile Val Asn Glu
        290                 295                 300
Leu Val Lys Lys Gly Lys Ile Thr Arg Pro Gln Leu Gly Val Arg Val
305                 310                 315                 320
Ile Ala Leu Gln Gly Ile Pro Glu Gly Tyr Arg Ser Arg Leu Lys Ile
                325                 330                 335
Lys Ser Asn Leu Lys Asn Gly Ile Tyr Ile Ala Phe Val Ser Arg Asn
                340                 345                 350
Gly Ser Ala Ala Asn Ala Gly Ile Lys Ser Gly Asp Val Ile Thr Lys
            355                 360                 365
Val Asp Gly Lys Lys Val Glu Asp Val Ala Ser Leu His Ser Ile Leu
370                 375                 380
Tyr Ser His Lys Val Gly Asp Thr Val Asn Val Thr Val Asn Arg Asn
385                 390                 395                 400
Gly Lys Asp Val Asp Met Lys Val Lys Leu Glu Gly Asn
                405                 410

<210> SEQ ID NO 31
<211> LENGTH: 423
<212> TYPE: PRT
<213> ORGANISM: Lactobacillus acidophilus

<400> SEQUENCE: 31

Met Ile Leu Gly Asn Met Arg Gly Glu Leu Ser Met Val Glu Asn Gln
1               5                   10                  15
Asn Asn Asn Gln Arg Pro Arg Lys Asn Ser Asn Ala Lys Ile Ile Thr
            20                  25                  30
Thr Ala Ala Ile Val Gly Val Val Gly Leu Ile Gly Gly Val
        35                  40                  45
Ser Tyr Tyr Ala Ala Asp Gln Met Asn Asn Ala Thr Asp Thr Thr Thr
    50                  55                  60
Ala Gln Thr Ser Val Ser Ser Asn Ser Ser Lys Val Ser Glu Lys Ser
```

```
                65                  70                  75                  80
Ala Lys Thr Ser Gly Thr Met Thr Thr Ala Tyr Asn Asp Val Lys Gly
                    85                  90                  95

Ala Val Val Ser Val Ile Asn Leu Lys Arg Gln Ser Ser Ser Ser Ser
                    100                 105                 110

Ala Asn Ser Leu Tyr Ser Ser Leu Phe Gly Asp Asp Ser Asp Ser Ser
                    115                 120                 125

Ser Gly Lys Ser Gly Lys Leu Glu Thr Tyr Ser Glu Gly Ser Ser Val
                130                 135                 140

Val Tyr Met Lys Ser Asn Gly Lys Gly Tyr Ile Val Thr Asn Asn His
145                 150                 155                 160

Val Ile Ser Gly Ser Asp Ala Val Gln Val Gln Leu Ala Asn Gly Lys
                    165                 170                 175

Thr Val Ser Ala Lys Val Val Gly Lys Asp Ser Thr Thr Asp Leu Ala
                    180                 185                 190

Val Leu Ser Ile Asp Ala Lys Tyr Val Thr Gln Thr Ala Glu Phe Gly
                    195                 200                 205

Asp Ser Lys Ser Leu Gln Ala Gly Gln Thr Val Ile Ala Val Gly Ser
                210                 215                 220

Pro Leu Gly Ser Glu Tyr Ala Ser Thr Val Thr Gln Gly Ile Ile Ser
225                 230                 235                 240

Ala Pro Ala Arg Thr Ile Ser Thr Ser Ser Gly Asn Gln Gln Thr Val
                    245                 250                 255

Ile Gln Thr Asp Ala Ala Ile Asn Pro Gly Asn Ser Gly Gly Ala Leu
                    260                 265                 270

Val Asn Ser Ala Gly Gln Val Ile Gly Ile Asn Ser Met Lys Leu Ala
                    275                 280                 285

Gln Ser Ser Asp Gly Thr Ser Val Glu Gly Met Gly Phe Ala Ile Pro
                290                 295                 300

Ser Asn Glu Val Val Thr Ile Val Asn Glu Leu Val Lys Lys Gly Lys
305                 310                 315                 320

Ile Thr Arg Pro Gln Leu Gly Val Arg Val Ala Leu Glu Gly Ile
                    325                 330                 335

Pro Glu Ala Tyr Arg Ser Arg Leu Lys Ile Lys Ser Asn Leu Lys Ser
                    340                 345                 350

Gly Ile Tyr Val Ala Ser Ile Asn Lys Asn Ser Ser Ala Ala Asn Ala
                    355                 360                 365

Gly Met Lys Ser Gly Asp Val Ile Thr Lys Val Asp Gly Lys Lys Val
                    370                 375                 380

Asp Asp Val Ala Ser Leu His Ser Ile Leu Tyr Ser His Lys Val Gly
385                 390                 395                 400

Asp Thr Val Asn Ile Thr Ile Asn Arg Asn Gly Arg Asp Val Asn Leu
                    405                 410                 415

Lys Val Lys Leu Glu Gly Asn
                420

<210> SEQ ID NO 32
<211> LENGTH: 420
<212> TYPE: PRT
<213> ORGANISM: Lactobacillus plantarum

<400> SEQUENCE: 32

Met Ala Asn Lys Ser Leu Ile Lys Val Ala Val Thr Ala Leu Val Ala
1                   5                   10                  15

Gly Leu Ile Gly Gly Gly Val Ala Tyr Gly Gly Ile Asn Tyr Phe Gln
```

```
                    20                  25                  30
Asn Asn Asn Ile Ala Thr Ser Ser Thr Ser Val Pro Thr Gly Ser Asn
                35                  40                  45

Lys Ser Gly Ser Thr Ser Thr Thr Asn Val Lys Val Asn Val Ser Ser
     50                  55                  60

Gln Ala Thr Lys Val Phe Glu Asn Asn Lys Ala Ala Val Val Ser Val
 65                  70                  75                  80

Ile Asn Leu Gln Lys Lys Ser Ser Ser Ser Trp Ser Gly Ile Leu
                 85                  90                  95

Gly Gly Asp Asp Ser Ser Gly Ser Asp Ser Ser Ser Ser Asp Ser
                100                 105                 110

Ser Ser Ser Lys Leu Glu Glu Tyr Ser Glu Gly Ser Gly Leu Ile Tyr
        115                 120                 125

Lys Lys Ser Gly Asp Ala Ala Tyr Ile Val Thr Asn Asn His Val Val
        130                 135                 140

Ser Gly Ser Ser Ala Ile Arg Val Ile Met Ser Asp Gly Thr Lys Leu
145                 150                 155                 160

Ser Ala Lys Ile Val Gly Thr Asp Ser Val Thr Asp Leu Ala Val Leu
                165                 170                 175

Lys Ile Asn Ser Ser Lys Val Thr Lys Thr Ala Ser Phe Gly Asn Ser
                180                 185                 190

Asp Asn Ile Lys Val Gly Glu Thr Ala Leu Ala Ile Gly Ser Pro Met
                195                 200                 205

Gly Ser Asn Tyr Ala Thr Thr Leu Thr Gln Gly Ile Ile Ser Ala Lys
        210                 215                 220

Lys Arg Thr Val Ala Thr Thr Asn Thr Ser Gly Gln Thr Thr Gly Tyr
225                 230                 235                 240

Ala Thr Val Ile Gln Thr Asp Thr Ala Ile Asn Ser Gly Asn Ser Gly
                245                 250                 255

Gly Pro Leu Phe Asn Ile Ala Gly Gln Val Ile Gly Ile Asn Ser Met
                260                 265                 270

Lys Leu Ala Ser Asp Asn Ser Gly Thr Ser Val Glu Gly Met Gly Phe
        275                 280                 285

Ala Ile Pro Ser Asn Glu Val Val Lys Ile Ile Asn Glu Leu Val Gln
        290                 295                 300

Lys Gly Glu Val Val Arg Pro Ala Leu Gly Val Ala Thr Tyr Asp Leu
305                 310                 315                 320

Ser Asn Ile Ser Ser Asp Gln Lys Ser Val Leu Lys Leu Pro Thr
                325                 330                 335

Ser Val Thr Lys Gly Val Val Ile Met Lys Thr Tyr Ser Gly Ser Pro
        340                 345                 350

Ala Lys Ala Ala Gly Leu Thr Lys Tyr Asp Val Ile Thr Glu Leu Gly
        355                 360                 365

Gly Lys Lys Val Thr Ser Leu Ala Thr Leu Arg Ser Ala Leu Tyr Ala
        370                 375                 380

His Ser Val Asn Asp Thr Val Thr Val Lys Tyr Tyr His Asn Gly Lys
385                 390                 395                 400

Leu Lys Thr Ala Asn Met Lys Leu Thr Glu Thr Thr Lys Thr Leu Thr
                405                 410                 415

Lys Gln Ser Asn
        420

<210> SEQ ID NO 33
<211> LENGTH: 411
```

```
<212> TYPE: PRT
<213> ORGANISM: Streptococcus thermophilus

<400> SEQUENCE: 33

Met Glu Lys Phe Asn Trp Lys Lys Ile Val Ala Pro Ile Ala Met Leu
1               5                   10                  15

Ile Ile Gly Leu Leu Gly Gly Leu Leu Gly Ala Phe Ile Leu Leu Thr
                20                  25                  30

Ala Ala Gly Val Ser Phe Thr Asn Thr Thr Asp Thr Gly Val Lys Thr
            35                  40                  45

Ala Lys Thr Val Tyr Thr Asn Ile Thr Asp Thr Lys Ala Val Lys
        50                  55                  60

Lys Val Gln Asn Ala Val Val Ser Val Ile Asn Tyr Gln Glu Gly Ser
65                  70                  75                  80

Ser Ser Asp Ser Leu Asn Asp Leu Tyr Gly Arg Ile Phe Gly Gly Gly
                85                  90                  95

Asp Ser Ser Asp Ser Ser Gln Glu Asn Ser Lys Asp Ser Asp Gly Leu
            100                 105                 110

Gln Val Ala Gly Glu Gly Ser Gly Val Ile Tyr Lys Lys Asp Gly Lys
        115                 120                 125

Glu Ala Tyr Ile Val Thr Asn Asn His Val Val Asp Gly Ala Lys Lys
130                 135                 140

Leu Glu Ile Met Leu Ser Asp Gly Ser Lys Ile Thr Gly Glu Leu Val
145                 150                 155                 160

Gly Lys Asp Thr Tyr Ser Asp Leu Ala Val Val Lys Val Ser Ser Asp
                165                 170                 175

Lys Ile Thr Thr Val Ala Glu Phe Ala Asp Ser Asn Ser Leu Thr Val
            180                 185                 190

Gly Glu Lys Ser Ile Ala Ile Gly Ser Pro Leu Gly Thr Glu Tyr Ala
        195                 200                 205

Asn Ser Val Thr Glu Gly Ile Val Ser Ser Leu Ser Arg Thr Ile Thr
210                 215                 220

Met Gln Asn Asp Asn Gly Glu Thr Val Ser Thr Ile Ala Ile Gln Thr
225                 230                 235                 240

Asp Ala Ala Ile Asn Pro Gly Asn Ser Gly Gly Ala Leu Val Asn Ile
                245                 250                 255

Glu Gly Gln Val Ile Gly Ile Asn Ser Ser Lys Ile Ser Ser Thr Ser
            260                 265                 270

Ala Val Ala Gly Ser Ala Val Glu Gly Met Gly Phe Ala Ile Pro Ser
        275                 280                 285

Asn Asp Val Val Glu Ile Ile Asn Gln Leu Glu Lys Asp Gly Lys Val
290                 295                 300

Thr Arg Pro Ala Leu Gly Ile Ser Ile Ala Asp Leu Asn Ser Leu Ser
305                 310                 315                 320

Ser Ser Ala Thr Ser Lys Leu Asp Leu Pro Asp Glu Val Lys Ser Gly
                325                 330                 335

Val Val Val Gly Ser Val Gln Lys Gly Met Pro Ala Asp Gly Lys Leu
            340                 345                 350

Gln Glu Tyr Asp Val Ile Thr Glu Ile Asp Gly Lys Lys Ile Gly Ser
        355                 360                 365

Lys Thr Asp Ile Gln Thr Asn Leu Tyr Ser His Ser Ile Gly Asp Thr
370                 375                 380

Ile Lys Val Thr Phe Tyr Arg Gly Lys Asp Lys Lys Thr Val Asp Leu
385                 390                 395                 400
```

Lys Leu Thr Lys Ser Thr Glu Asp Ile Ser Asp
        405                 410

<210> SEQ ID NO 34
<211> LENGTH: 411
<212> TYPE: PRT
<213> ORGANISM: Streptococcus thermophilus

<400> SEQUENCE: 34

Met Lys Lys Phe Asn Trp Lys Lys Ile Val Ala Pro Ile Ala Met Leu
 1               5                  10                  15

Ile Ile Gly Leu Leu Gly Gly Leu Leu Gly Ala Phe Ile Leu Leu Thr
            20                  25                  30

Ala Ala Gly Val Ser Phe Thr Asn Thr Thr Asp Thr Gly Val Lys Thr
        35                  40                  45

Ala Lys Thr Val Tyr Thr Asn Ile Thr Asp Thr Thr Lys Ala Val Lys
    50                  55                  60

Lys Val Gln Asn Ala Val Val Ser Val Ile Asn Tyr Gln Glu Gly Ser
65                  70                  75                  80

Ser Ser Asp Ser Leu Asn Asp Leu Tyr Gly Arg Ile Phe Gly Gly Gly
                85                  90                  95

Asp Ser Ser Asp Ser Ser Gln Glu Asn Ser Lys Asp Ser Asp Gly Leu
            100                 105                 110

Gln Val Ala Gly Glu Gly Ser Gly Val Ile Tyr Lys Lys Asp Gly Lys
        115                 120                 125

Glu Ala Tyr Ile Val Thr Asn Asn His Val Val Asp Gly Ala Lys Lys
    130                 135                 140

Leu Glu Ile Met Leu Ser Asp Gly Ser Lys Ile Thr Gly Glu Leu Val
145                 150                 155                 160

Gly Lys Asp Thr Tyr Ser Asp Leu Ala Val Val Lys Val Ser Ser Asp
                165                 170                 175

Lys Ile Thr Thr Val Ala Glu Phe Ala Asp Ser Asn Ser Leu Thr Val
            180                 185                 190

Gly Glu Lys Ala Ile Ala Ile Gly Ser Pro Leu Gly Thr Glu Tyr Ala
        195                 200                 205

Asn Ser Val Thr Glu Gly Ile Val Ser Ser Leu Ser Arg Thr Ile Thr
    210                 215                 220

Met Gln Asn Asp Asn Gly Glu Thr Val Ser Thr Asn Ala Ile Gln Thr
225                 230                 235                 240

Asp Ala Ala Ile Asn Pro Gly Asn Ser Gly Gly Ala Leu Val Asn Ile
                245                 250                 255

Glu Gly Gln Val Ile Gly Ile Asn Ser Ser Lys Ile Ser Ser Thr Ser
            260                 265                 270

Ala Val Ala Gly Ser Ala Val Glu Gly Met Gly Phe Ala Ile Pro Ser
        275                 280                 285

Asn Asp Val Val Glu Ile Ile Asn Gln Leu Glu Lys Asp Gly Lys Val
    290                 295                 300

Thr Arg Pro Ala Leu Gly Ile Ser Ile Ala Asp Leu Asn Ser Leu Ser
305                 310                 315                 320

Ser Ser Ala Thr Ser Lys Leu Asp Leu Pro Asp Glu Val Lys Ser Gly
                325                 330                 335

Val Val Val Gly Ser Val Gln Lys Gly Met Pro Ala Asp Gly Lys Leu
            340                 345                 350

Gln Glu Tyr Asp Val Ile Thr Glu Ile Asp Gly Lys Lys Ile Ser Ser
        355                 360                 365

-continued

Lys Thr Asp Ile Gln Thr Asn Leu Tyr Ser His Ser Ile Gly Asp Thr
            370                 375                 380

Ile Lys Val Thr Phe Tyr Arg Gly Lys Asp Lys Thr Val Asp Leu
385                 390                 395                 400

Lys Leu Thr Lys Ser Thr Glu Asp Ile Ser Asp
            405                 410

<210> SEQ ID NO 35
<211> LENGTH: 407
<212> TYPE: PRT
<213> ORGANISM: Lactococcus lactis

<400> SEQUENCE: 35

Met Ala Lys Ala Asn Ile Gly Lys Leu Leu Thr Gly Val Val Gly
  1               5                  10                  15

Gly Ala Ile Ala Leu Gly Gly Ser Ala Ile Tyr Gln Ser Thr Thr Asn
                 20                  25                  30

Gln Leu Gly Asn Ala Asn Arg Ser Asn Thr Thr Ser Thr Lys Val Ser
             35                  40                  45

Asn Val Ser Val Asn Val Asn Thr Asp Val Thr Ser Ala Ile Lys Lys
 50                  55                  60

Val Ser Asn Ser Val Val Ser Val Met Asn Tyr Gln Lys Gln Asn Ser
 65                  70                  75                  80

Gln Ser Asp Phe Ser Ser Ile Phe Gly Gly Asn Ser Gly Ser Ser Ser
                 85                  90                  95

Ala Asn Asp Gly Leu Gln Leu Ser Ser Glu Gly Ser Gly Val Ile Tyr
                100                 105                 110

Lys Lys Ser Gly Gly Asp Ala Tyr Val Val Thr Asn Tyr His Val Ile
            115                 120                 125

Ala Gly Asn Ser Ser Leu Asp Val Leu Leu Ser Gly Gly Gln Lys Val
130                 135                 140

Lys Ala Thr Val Val Gly Tyr Asp Glu Tyr Thr Asp Leu Ala Val Leu
145                 150                 155                 160

Lys Ile Ser Ser Asp His Val Lys Asp Val Ala Thr Phe Ala Asp Ser
                165                 170                 175

Ser Lys Leu Thr Ile Gly Glu Pro Ala Ile Ala Val Gly Ser Pro Leu
            180                 185                 190

Gly Ser Gln Phe Ala Asn Thr Ala Thr Glu Gly Ile Leu Ser Ala Thr
            195                 200                 205

Ser Arg Gln Val Thr Leu Thr Gln Glu Asn Gly Gln Thr Thr Ser Ile
        210                 215                 220

Asn Ala Ile Gln Thr Asp Ala Ala Ile Asn Pro Gly Asn Ser Gly Gly
225                 230                 235                 240

Ala Leu Ile Asn Ile Glu Gly Gln Val Ile Gly Ile Thr Gln Ser Lys
                245                 250                 255

Ile Thr Thr Thr Glu Asp Gly Ser Thr Ser Val Glu Gly Leu Gly Phe
            260                 265                 270

Ala Ile Pro Ser Asn Asp Val Val Asn Ile Asn Lys Leu Glu Thr
            275                 280                 285

Asp Gly Lys Ile Ser Arg Pro Ala Leu Gly Ile Arg Met Val Asp Leu
        290                 295                 300

Ser Gln Leu Ser Thr Asn Asp Ser Ser Gln Leu Lys Leu Pro Ser Ser
305                 310                 315                 320

Val Thr Gly Gly Val Val Val Tyr Ser Val Gln Ala Gly Leu Pro Ala
                325                 330                 335

```
Ala Thr Ala Gly Leu Lys Ala Gly Asp Val Ile Thr Lys Val Gly Asp
            340                 345                 350

Thr Ala Val Thr Ser Ser Thr Asp Leu Gln Ser Ala Leu Tyr Ser His
        355                 360                 365

Asn Ile Asn Asp Thr Val Lys Val Thr Tyr Tyr Arg Asp Gly Lys Ser
    370                 375                 380

Ala Thr Ala Asn Val Lys Leu Ser Lys Ser Thr Ser Asp Leu Glu Thr
385                 390                 395                 400

Asn Ser Pro Ser Ser Ser Asn
                405

<210> SEQ ID NO 36
<211> LENGTH: 361
<212> TYPE: PRT
<213> ORGANISM: Actinobacillus actinomycetemcomitans

<400> SEQUENCE: 36

Asn Cys Cys Val Lys Gly Asn Ser Ile Tyr Pro Gln Lys Thr Ser Thr
1               5                   10                  15

Lys Gln Thr Gly Leu Met Leu Asp Ile Ala Arg His Phe Tyr Ser Pro
            20                  25                  30

Glu Val Ile Lys Ser Phe Ile Asp Thr Ile Ser Leu Ser Gly Gly Asn
        35                  40                  45

Phe Leu His Leu His Phe Ser Asp His Glu Asn Tyr Ala Ile Glu Ser
    50                  55                  60

His Leu Leu Asn Gln Arg Ala Glu Asn Ala Val Gln Gly Lys Asp Gly
65                  70                  75                  80

Ile Tyr Ile Asn Pro Tyr Thr Gly Lys Pro Phe Leu Ser Tyr Arg Gln
                85                  90                  95

Leu Asp Asp Ile Lys Ala Tyr Ala Lys Ala Lys Gly Ile Glu Leu Ile
            100                 105                 110

Pro Glu Leu Asp Ser Pro Asn His Met Thr Ala Ile Phe Lys Leu Val
        115                 120                 125

Gln Lys Asp Arg Gly Val Lys Tyr Leu Gln Gly Leu Lys Ser Arg Gln
    130                 135                 140

Val Asp Asp Glu Ile Asp Ile Thr Asn Ala Asp Ser Ile Thr Phe Met
145                 150                 155                 160

Gln Ser Leu Met Ser Glu Val Ile Asp Ile Phe Gly Asp Thr Ser Gln
                165                 170                 175

His Phe His Ile Gly Gly Asp Glu Phe Gly Tyr Ser Val Glu Ser Asn
            180                 185                 190

His Glu Phe Ile Thr Tyr Ala Asn Lys Leu Ser Tyr Phe Leu Glu Lys
        195                 200                 205

Lys Gly Leu Lys Thr Arg Met Trp Asn Asp Gly Leu Ile Lys Asn Thr
    210                 215                 220

Phe Glu Gln Ile Asn Pro Asn Ile Glu Ile Thr Tyr Trp Ser Tyr Asp
225                 230                 235                 240

Gly Asp Thr Gln Asp Lys Asn Glu Ala Ala Glu Arg Arg Asp Met Arg
                245                 250                 255

Val Ser Leu Pro Glu Leu Leu Ala Lys Gly Phe Thr Val Leu Asn Tyr
            260                 265                 270

Asn Ser Tyr Tyr Leu Tyr Ile Val Pro Lys Ala Ser Pro Thr Phe Ser
        275                 280                 285

Gln Asp Ala Ala Phe Ala Ala Lys Asp Val Ile Lys Asn Trp Asp Leu
    290                 295                 300
```

```
Gly Val Trp Asp Gly Arg Asn Thr Lys Asn Arg Val Gln Asn Thr His
305                 310                 315                 320

Glu Ile Ala Gly Ala Ala Leu Ser Ile Trp Gly Glu Asp Ala Lys Ala
                325                 330                 335

Leu Lys Asp Glu Thr Ile Gln Lys Asn Thr Lys Ser Leu Leu Glu Ala
            340                 345                 350

Val Ile His Lys Thr Asn Gly Asp Glu
        355                 360

<210> SEQ ID NO 37
<211> LENGTH: 377
<212> TYPE: PRT
<213> ORGANISM: Actinobacillus pleuropneumoniae

<400> SEQUENCE: 37

Met Lys Lys Ala Ile Thr Leu Phe Thr Leu Leu Cys Ala Val Leu Leu
1               5                   10                  15

Ser Phe Ser Thr Ala Thr Tyr Ala Asn Ala Met Asp Leu Pro Lys Lys
            20                  25                  30

Glu Ser Gly Leu Thr Leu Asp Ile Ala Arg Arg Phe Tyr Thr Val Asp
        35                  40                  45

Thr Ile Lys Gln Phe Ile Asp Thr Ile His Gln Ala Gly Gly Thr Phe
    50                  55                  60

Leu His Leu His Phe Ser Asp His Glu Asn Tyr Ala Leu Glu Ser Ser
65                  70                  75                  80

Tyr Leu Glu Gln Arg Glu Glu Asn Ala Thr Glu Lys Asn Gly Thr Tyr
                85                  90                  95

Phe Asn Pro Lys Thr Asn Lys Pro Phe Leu Thr Tyr Lys Gln Leu Asn
            100                 105                 110

Glu Ile Ile Tyr Tyr Ala Lys Glu Arg Asn Ile Glu Ile Val Pro Glu
        115                 120                 125

Val Asp Ser Pro Asn His Met Thr Ala Ile Phe Asp Leu Leu Thr Leu
    130                 135                 140

Lys His Gly Lys Glu Tyr Val Lys Gly Leu Lys Ser Pro Tyr Ile Ala
145                 150                 155                 160

Glu Glu Ile Asp Ile Asn Asn Pro Glu Ala Val Glu Val Ile Lys Thr
                165                 170                 175

Leu Ile Gly Glu Val Ile Tyr Ile Phe Gly His Ser Ser Arg His Phe
            180                 185                 190

His Ile Gly Gly Asp Glu Phe Ser Tyr Ala Val Glu Asn Asn His Glu
        195                 200                 205

Phe Ile Arg Tyr Val Asn Thr Leu Asn Asp Phe Ile Asn Ser Lys Gly
    210                 215                 220

Leu Ile Thr Arg Val Trp Asn Asp Gly Leu Ile Lys Asn Asn Leu Ser
225                 230                 235                 240

Glu Leu Asn Lys Asn Ile Glu Ile Thr Tyr Trp Ser Tyr Asp Gly Asp
                245                 250                 255

Ala Gln Ala Lys Glu Asp Ile Gln Tyr Arg Arg Glu Ile Arg Ala Asp
            260                 265                 270

Leu Pro Glu Leu Leu Ala Asn Gly Phe Lys Val Leu Asn Tyr Asn Ser
        275                 280                 285

Tyr Tyr Leu Tyr Phe Val Pro Lys Ser Gly Ser Asn Ile His Asn Asp
    290                 295                 300

Gly Lys Tyr Ala Ala Glu Asp Val Leu Asn Asn Trp Thr Leu Gly Lys
305                 310                 315                 320
```

```
Trp Asp Gly Lys Asn Ser Ser Asn His Val Gln Asn Thr Gln Asn Ile
            325                 330                 335

Ile Gly Ser Ser Leu Ser Ile Trp Gly Glu Arg Ser Ser Ala Leu Asn
            340                 345                 350

Glu Gln Thr Ile Gln Ala Ser Lys Asn Leu Leu Lys Ala Val Ile
            355                 360                 365

Gln Lys Thr Asn Asp Pro Lys Ser His
            370                 375

<210> SEQ ID NO 38
<211> LENGTH: 325
<212> TYPE: PRT
<213> ORGANISM: Lactococcus lactis

<400> SEQUENCE: 38

Met Glu Lys Gly Leu Leu Val Asp Ile Gly Arg Lys Tyr Trp Ser Ile
  1               5                  10                  15

Ala Glu Leu Lys Arg Leu Val Leu Leu Gln Glu His Lys Leu Thr
                 20                  25                  30

His Leu Gln Leu His Leu Asn Glu Asn Glu Gly Phe Ala Leu Asn Phe
             35                  40                  45

Thr Asp Ser Pro Val Ser Lys Lys Tyr Ser Glu Asn Met Leu Lys Glu
         50                  55                  60

Leu Lys Glu Phe Ala Lys Thr His Glu Ile Thr Leu Ile Pro Asp Phe
 65                  70                  75                  80

Asp Ser Pro Gly His Met Gly Ser Leu Leu Glu Gln Asn Pro Glu Phe
                 85                  90                  95

Ala Leu Pro Asp Ser Asn Gln Gln Ala Val Asp Val Thr Asn Pro Ala
            100                 105                 110

Val Ile Asp Trp Ile Met Gly Ile Ile Asp Lys Ile Val Asp Ile Phe
            115                 120                 125

Pro Asp Ser Asp Thr Phe His Ile Gly Ala Asp Glu Phe Ile Asp Phe
        130                 135                 140

Arg Gln Ile Glu Lys Tyr Pro Tyr Leu Val Glu Lys Thr Arg Glu Lys
145                 150                 155                 160

Tyr Gly Asn Lys Ala Ser Gly Leu Glu Phe Tyr Tyr Asp Tyr Val Asn
                165                 170                 175

Gln Leu Thr Glu His Leu Gln Lys Gly Lys Gln Val Arg Ile Trp
            180                 185                 190

Asn Asp Gly Phe Leu Arg Lys Asp Leu Gln Ser Leu Val Pro Leu Asn
            195                 200                 205

Lys Asn Val Glu Val Cys Tyr Trp Thr Asn Trp Asp Lys Gly Met Ala
        210                 215                 220

Glu Val Lys Glu Trp Leu Thr Lys Gly Tyr Thr Leu Ile Asn Phe Cys
225                 230                 235                 240

Asp Asn Asp Leu Tyr Tyr Val Leu Gly Glu Ala Gly Tyr Ser Tyr
                245                 250                 255

Pro Thr Ala Glu Lys Leu Glu Arg Glu Gly Lys Ile Gln Lys Phe Ser
            260                 265                 270

Gly Gln Gln Tyr Leu Asn Gln Glu Glu Met Lys Ala Val Arg Gly Thr
        275                 280                 285

Tyr Phe Ser Ile Trp Ala Asp Asn Ala Ala Ala Lys Ser Val Ser Glu
        290                 295                 300

Ile Leu Asp Asp Leu Ser Lys Val Leu Pro Val Phe Met Lys Ile Tyr
305                 310                 315                 320
```

```
Gly Gly Asn Asp Glu
            325

<210> SEQ ID NO 39
<211> LENGTH: 526
<212> TYPE: PRT
<213> ORGANISM: Lactobacillus casei

<400> SEQUENCE: 39

Met Val Leu Ser Leu Ser Gln Pro Pro Lys Gln Val Ala Ala Asp
 1               5                  10                  15

Asn Thr Leu Lys Ser Val Phe Ser Ile Asp Ala Gly Arg Lys Phe Phe
                20                  25                  30

Ser Ala Asp Gln Leu Lys Met Ile Ile Asp Arg Ala His Thr Asp Gly
                35                  40                  45

Tyr Thr Asp Val Gln Val Leu Leu Gly Asn Asp Ala Leu Arg Leu Leu
         50                  55                  60

Leu Asp Asp Met Ser Val Thr Ile Asn Gly Lys Thr Tyr Gly Ser Asp
 65                  70                  75                  80

Val Val Lys Gln Ala Ile Gln Ala Gly Asn Lys Ala Tyr Tyr Asp Asp
                 85                  90                  95

Pro Asn Gly Asn Ala Leu Thr Gln Thr Asp Met Asp Ala Val Leu Lys
                100                 105                 110

Tyr Ala Ala Arg Asp Ile Asn Ile Ile Pro Val Ile Asn Ser Pro
                115                 120                 125

Gly His Met Asp Ala Ile Leu Thr Ala Met Ala Gln Leu Gly Ile Lys
            130                 135                 140

Asn Pro Ala Phe Asn Gly Ser Lys Arg Thr Val Asp Leu Asn Asn Asp
145                 150                 155                 160

Thr Ala Ile Ala Phe Thr Lys Ala Leu Leu Gln Lys Tyr Val Met Tyr
                165                 170                 175

Phe Lys Gly His Ala Thr Ile Phe Asn Phe Gly Ser Asp Glu Tyr Ala
            180                 185                 190

Asn Asp Val Asp Thr Gly Gly Trp Ala Lys Leu Gln Gln Ser Gly Thr
            195                 200                 205

Tyr Lys Lys Phe Val Ala Tyr Val Asn Asp Leu Ala Ala Met Ala Lys
        210                 215                 220

Asn Ala Ser Leu Lys Pro Met Val Phe Asn Asp Gly Ile Tyr Tyr Asp
225                 230                 235                 240

Asn Asn Thr Ser Phe Gly Thr Phe Asp Lys Asp Leu Ile Val Ser Tyr
                245                 250                 255

Trp Thr Ala Gly Trp Gly Gly Tyr Asp Val Ala Lys Pro Glu Phe Leu
            260                 265                 270

Thr Asp Lys Gly Leu Lys Ile Met Asn Thr Asn Asp Gly Trp Tyr Trp
        275                 280                 285

Val Leu Gly Arg Val Asp Gly Asp Leu Tyr Ser Tyr Lys Thr Ala Leu
            290                 295                 300

Ala Ser Leu Ala Ser Lys Lys Phe Thr Asp Val Pro Gly Ala Ser Ser
305                 310                 315                 320

Ala Val Pro Ile Ile Gly Ser Val Gln Ala Val Trp Ala Asp Pro
                325                 330                 335

Ser Ala Gln Leu Asp Met Pro Ala Leu Leu Lys Leu Met Asp Gln Phe
            340                 345                 350

Ser Thr Ala Tyr Ala Pro Tyr Leu Val Arg Pro Ala Asp Tyr Ser Lys
        355                 360                 365
```

-continued

```
Val Asp Ala Ala Ile Ala Ala Val Pro Arg Gln Leu Asn Gln Tyr Thr
    370                 375                 380

Glu Ala Ser Val Ala Lys Leu Asp Ala Ala Leu Asn Ala Val Val Arg
385                 390                 395                 400

Gly Lys Lys Ala Thr Asp Gln Ala Leu Val Asp Gly Tyr Ala Gln Thr
                405                 410                 415

Ile Thr Val Ala Ile Lys Ala Leu Gln Leu Arg Pro Ala Asp Tyr Thr
            420                 425                 430

Lys Val Asp Ala Ala Ile Ala Ala Lys Lys Leu Asp Arg Ser His
        435                 440                 445

Tyr Gln Asp Leu Ser Ala Val Asp Ala Ala Leu Ala Ala Val Asn Arg
    450                 455                 460

Asn Leu Ser Ile Thr Gln Gln Ala Gln Ala Asp Thr Met Ala Ala Lys
465                 470                 475                 480

Ile Thr Ala Ala Ile Ala Ala Leu Val Leu Lys Pro Ala Pro Gln Pro
                485                 490                 495

Asp Pro Arg Gln Gln Val Pro Thr Lys Thr Ile Val Asn Pro Asp
            500                 505                 510

Arg Tyr Leu Pro Lys Thr Ala Glu Ala Ser Arg Val Gly Asn
        515                 520                 525

<210> SEQ ID NO 40
<211> LENGTH: 325
<212> TYPE: PRT
<213> ORGANISM: Lactococcus lactis

<400> SEQUENCE: 40

Met Glu Lys Gly Leu Leu Val Asp Ile Gly Arg Lys Tyr Trp Ser Ile
1               5                   10                  15

Ala Glu Leu Lys Arg Leu Val Leu Leu Gln Glu His Lys Leu Thr
            20                  25                  30

His Leu Gln Leu His Leu Asn Glu Asn Glu Gly Phe Ala Leu Asn Phe
        35                  40                  45

Thr Asp Ser Pro Val Ser Lys Lys Tyr Ser Glu Asn Met Leu Lys Glu
    50                  55                  60

Leu Lys Glu Phe Ala Lys Thr His Glu Ile Thr Leu Ile Pro Asp Phe
65                  70                  75                  80

Asp Ser Pro Gly His Met Gly Ser Leu Leu Glu Gln Asn Pro Glu Phe
                85                  90                  95

Ala Leu Pro Asp Ser Asn Gln Gln Ala Val Asp Val Thr Asn Pro Ala
            100                 105                 110

Val Ile Asp Trp Ile Met Gly Ile Ile Asp Lys Ile Val Asp Ile Phe
        115                 120                 125

Pro Asp Ser Asp Thr Phe His Ile Gly Ala Asp Glu Phe Ile Asp Phe
    130                 135                 140

Arg Gln Ile Glu Lys Tyr Pro Tyr Leu Val Glu Lys Thr Arg Glu Lys
145                 150                 155                 160

Tyr Gly Asn Lys Ala Ser Gly Leu Glu Phe Tyr Tyr Asp Tyr Val Asn
                165                 170                 175

Gln Leu Thr Glu His Leu Gln Lys Lys Gly Lys Gln Val Arg Ile Trp
            180                 185                 190

Asn Asp Gly Phe Leu Arg Lys Asp Leu Gln Ser Leu Val Pro Leu Asn
        195                 200                 205

Lys Asn Val Glu Val Cys Tyr Trp Thr Asn Trp Asp Lys Gly Met Ala
    210                 215                 220
```

-continued

Glu Val Lys Glu Trp Leu Thr Lys Gly Tyr Thr Leu Ile Asn Phe Cys
225                 230                 235                 240

Asp Asn Asp Leu Tyr Tyr Val Leu Gly Glu Ala Gly Tyr Ser Tyr
            245                 250                 255

Pro Thr Ala Glu Lys Leu Glu Arg Glu Gly Lys Ile Gln Lys Phe Ser
            260                 265                 270

Gly Gln Gln Tyr Leu Asn Gln Glu Met Lys Ala Val Arg Gly Thr
            275                 280                 285

Tyr Phe Ser Ile Trp Ala Asp Asn Ala Ala Lys Ser Val Ser Glu
    290                 295                 300

Ile Leu Asp Asp Leu Ser Lys Val Leu Pro Val Phe Met Lys Ile Tyr
305                 310                 315                 320

Gly Gly Asn Asp Glu
            325

<210> SEQ ID NO 41
<211> LENGTH: 639
<212> TYPE: PRT
<213> ORGANISM: Streptomyces sp.

<400> SEQUENCE: 41

Met Asp Met Arg Met Ala Arg Arg Thr Ile Gly Ala Val Val Thr
1               5                   10                  15

Ala Leu Ala Ala Ala Leu Leu Pro Trp Gln Ser Ala Thr Ala Glu Gly
                20                  25                  30

Gly Ser Ala Ala Ala Ala Pro Pro Glu Val Leu Pro Thr Leu Arg Glu
            35                  40                  45

Trp Gln Gly Gly Gln Gly Glu Phe Thr Leu Thr Asp Arg Ala Gly Ile
    50                  55                  60

Val Leu Asp Gly Val Arg Asp Ser Arg Thr Ala Ala Asp Ala Arg Arg
65                  70                  75                  80

Phe Ala Gly Glu Leu Asn Gly Lys Ala Ser Val Ser Gln Gly Arg Ala
                85                  90                  95

Ala Arg Pro Gly Asp Ile Val Leu Arg Gln Asp Pro Ala Gln Lys Gly
            100                 105                 110

Leu Leu Gly Ala Glu Gly Tyr Arg Leu Thr Val Gly Thr Arg Ile Thr
        115                 120                 125

Val Thr Ala Ala Thr Ser Thr Gly Val Phe Tyr Gly Thr Arg Thr Val
130                 135                 140

Leu Gln Leu Leu Asn Asp Asp Gly Arg Ala Arg Gly Ser Ala Thr
145                 150                 155                 160

Asp Val Pro Ala Tyr Arg Glu Arg Gly Val Gly Val Cys Ala Cys Tyr
            165                 170                 175

Ile Asn Ile Ser Thr Gln Trp Phe Glu Arg Leu Met Lys Asp Met Ala
        180                 185                 190

Ser Gln Lys Leu Asn Gln Leu Trp Ile Glu Ala Lys Val Lys Ser Asp
        195                 200                 205

Thr Asp Pro Ala Ser Ala Phe Trp Gly Tyr Tyr Thr Lys Pro Gln Val
210                 215                 220

Arg Thr Leu Val Ala Met Ala Arg Lys Tyr His Ile Glu Leu Val Pro
225                 230                 235                 240

Glu Ile Asn Ser Pro Gly His Met Asp Thr Tyr Leu Glu Asn His Pro
            245                 250                 255

Glu Leu Gln Leu Lys Asp Arg Asp Gly Val Ala Ser Pro Pro Arg Leu
        260                 265                 270

-continued

```
Asp Ile Ser Arg Pro Glu Ala Leu Ala Tyr Tyr Thr Ser Met Val Asp
        275                 280                 285

Glu Ala Leu Lys Val Trp Asp Ser Arg Tyr Trp His Met Gly Ala Asp
    290                 295                 300

Glu Tyr Met Ile Gly Ser Ser Tyr Pro Asp Tyr Pro Gln Leu Gln Ala
305                 310                 315                 320

Ala Ala Arg Ala Lys Phe Gly Ala Ser Ala Thr Pro Asp Asp Leu Phe
                325                 330                 335

Thr Asp Phe Ile Asn Gln Val Asn Ala His Val Lys Ala Asp Gly Arg
                340                 345                 350

Ser Leu Arg Ile Trp Asn Asp Gly Leu Ala Gly Lys Asn Ala Val Val
                355                 360                 365

Pro Leu Asp Arg Asp Ile Thr Val Glu His Trp Leu Ser Gly Gly Ser
370                 375                 380

Ile Gln Gln Pro Ser Ser Leu Leu Ala Glu Gly Arg Pro Val Met Asn
385                 390                 395                 400

Ser Ala Tyr Ser Leu Tyr Leu Val Arg Gly Gly Phe Thr Met Gln Thr
                405                 410                 415

Gln Lys Leu Tyr Glu Ser Asp Trp Thr Pro Leu Arg Phe Glu Gly Gln
                420                 425                 430

Thr Leu Thr Gln Gly Ala Ala Asn Leu Thr Gly Ala Lys Ile Ser Leu
                435                 440                 445

Trp Pro Asp Ser Ala Ala Ala Glu Thr Glu Asn Glu Val Glu Thr Lys
    450                 455                 460

Val Phe Met Pro Leu Arg Phe Val Ala Gln Ala Thr Trp Gly Gly Pro
465                 470                 475                 480

Lys Pro Ser Pro Thr Tyr Ala Gly Phe Glu Ala Leu Ala Arg Lys Ile
                485                 490                 495

Gly His Ala Pro Gly Trp Glu Asn Thr Asp Arg Thr Pro Leu Ala Asp
                500                 505                 510

Gly Thr Tyr Arg Leu Thr Thr Gly Ala Lys Ala Leu Ala Pro Thr Ala
            515                 520                 525

Asp Ala Gly Val Ser Leu Val Lys Asn Ser Ala Ala Ser Trp Ala Leu
    530                 535                 540

Thr Ala Thr Ala Asp Gly Tyr Tyr Thr Val Arg Ser Thr Glu Ser Gly
545                 550                 555                 560

Gln Cys Leu Asp Ala Val Arg Gly Lys Lys Tyr Leu Gly Ala Pro Leu
                565                 570                 575

Glu Val Gly Ala Glu Leu Ser Leu Ala Asn Cys Ser Thr Thr Ala Arg
            580                 585                 590

Thr Gln Arg Trp Gln Leu Asp Thr Gly Ala Gly Ala Leu Thr Leu Arg
            595                 600                 605

Asn Ala Ile Ser Gln Leu His Leu Thr Glu Arg Ala Ser Asp Gly Ala
    610                 615                 620

Ala Val Gln Thr Thr Gly Ala Thr Arg Leu Thr Ala Arg Ala Ala
625                 630                 635
```

US 8,038,990 B2

COMPOSITIONS AND METHODS FOR THE PREVENTION AND REMOVAL OF BIOFILMS ON INERT AND BIOLOGICAL SURFACES

CROSS REFERENCE TO RELATED APPLICATIONS

This application claims priority to and any other benefit of U.S. Provisional Patent Application No. 60/686,629, filed Jun. 1, 2005, the entirety of which is incorporated by reference herein.

BACKGROUND

Biofilms are biological films that develop and persist at the surfaces of biotic (biological) or abiotic (inert) objects in aqueous environments from the adsorption of microbial cells onto the solid surfaces. This adsorption can provide a competitive advantage for the microorganisms since they can reproduce, are accessible to a wider variety of nutrients and oxygen conditions, are not washed away, and are less sensitive to antimicrobial agents. The formation of the biofilm is also accompanied by the production of exo-polymeric materials (polysaccharides, polyuronic acids, alginates, glycoproteins, and proteins) which together with the cells form thick layers of differentiated structures separated by water-filled spaces. The resident microorganisms may be individual species of microbial cells or mixed communities of microbial cells, which may include aerobic and anaerobic bacteria, algae, protozoa, and fungi. Thus, the biofilm is a complex assembly of living microorganisms embedded in an organic structure composed of one or more matrix polymers which are secreted by the resident microorganisms.

Biofilms can develop into macroscopic structures several millimeters or centimeters in thickness and cover large surface areas. For non-living objects, these formations can play a role in restricting or entirely blocking flow in plumbing systems, decreasing heat transfer in heat exchangers, or causing pathogenic problems in municipal water supplies, food processing, medical devices (e.g., catheters, orthopedic devices, implants). Moreover, biofilms often decrease the life of materials through corrosive action mediated by the embedded microorganisms. This biological fouling is a serious economic problem in industrial water process systems, pulp and paper production processes, cooling water systems, injection wells for oil recovery, cooling towers, porous media (sand and soil), marine environments, and air conditioning systems, and any closed water recirculation system. Biofilms are also a problem in medical science and industry causing dental plaque, infections (Costerton et al., 1999, Science 284: 1318-1322), contaminated endoscopes and contact lenses, prosthetic device colonisation and biofilm formation on medical implants.

Biofilms occur in a wide range of locations. Many are found on or in the human body, including on the teeth, gums, ears, prostate, lungs, and heart, where they are believed to be implicated in chronic infections such as gum disease, ear infections, infections of the prostate gland and heart, and lung infections in people with cystic fibrosis. Biofilms also occur in nature, such as the slime that covers river rocks, marshes, and the like. Biofilms also occur in medical equipment, such as catheters, and are a major source of hospital infections. Biofilms can also occur in areas such as contact lenses; other medical equipment. And biofilms can occur in the food processing and handling industries.

Biofilms produced by oral pathogens are involved in the etiology of some of the most common diseases of the oral cavity, i.e. dental caries, periodontal disease, and peri-impantitis. Formation of oral biofilms is a complex process involving polymicrobial interactions. Neeser et al (US2002/0012637 A1) attempted to treat dental caries, dental plaque and periodontal infections by replacing or limiting pathogenic oral biofilm development with non-residential commensal organisms such as low acidifying lactic acid bacteria that can adhere to the pellicle of the teeth (Neeser et al., US2002/0012637 A1).

Bacteria growing in biofilms are more resistant to antibiotics and disinfectants than planktonic cells and the resistance increases with the age of the biofilm. Bacterial biofilm also exhibits increased physical resistance towards desiccation, extreme temperatures or light. Difficulties in cleaning and disinfection of bacterial biofilm with chemicals is a major concern in many industries. Furthermore, the trend towards milder disinfection and cleaning compositions may increase the insufficient cleaning of surfaces covered with biofilm.

Accordingly, there exists a is a need for improved methods and new systems and compositions that can reduce or eliminate biofilms and/or the formation of biofilms on inert and biological surfaces.

SUMMARY OF THE INVENTION

In accordance with embodiments of the present invention, methods for preventing or removing a biofilm are provided. The methods can comprise contacting a biofilm or a biofilm surface with a composition such that biofilm formation on the biofilm surface is reduced or the biofilm is at least partially removed. The composition can comprise at least one of an organism that overexpresses one or more of *Lactococcus lactis* HtrA, *Lactococcus lactis* PrtP, *Lactococcus lactis* PrtM, *Lactococcus lactis* CluA, *Streptococcus gordonii* SspA, *Streptococcus mutans* Pac, *Lactococcus lactis* InbA, *Lactobacillus johnsonii* HtrH-like proteinase, *Lactobacillus acidophilus* HtrH-like proteinase, and *Streptococcus thermophilus* exported proteinase, isolated *Lactococcus lactis* HtrA, isolated *Lactococcus lactis* PrtP, isolated *Lactococcus lactis* PrtM, isolated *Lactococcus lactis* CluA, isolated *Streptococcus gordonii* SspA, isolated *Streptococcus mutans* Pac, isolated *Lactococcus lactis* InbA, isolated *Lactobacillus johnsonii* HtrH-like proteinase, isolated *Lactobacillus acidophilus* HtrH-like proteinase, and isolated *Streptococcus thermophilus* exported proteinase.

It will be understood both the forgoing general description and the following detailed description are exemplary and explanatory only and are not restrictive of the invention as claimed.

BRIEF DESCRIPTION OF THE SEVERAL VIEWS OF THE DRAWINGS

The following detailed description of embodiments of the present invention can be best understood when read in conjunction with the following drawings, where like structure is indicated with like reference numerals and in which:

FIG. 1 illustrates the *Lactococcus lactis* HtrA sequence (SEQ ID NO: 1);

FIG. 2 illustrates the *Lactococcus lactis* Proteinase (PrtP) sequence (SEQ ID NO: 2);

FIG. 3 illustrates the *Lactococcus lactis* PrtM sequence (SEQ ID NO: 3);

FIG. 4 illustrates the *Lactococcus lactis* CluA sequence (SEQ ID NO: 4);

FIG. 5 illustrates the *Streptococcus gordonii* cell surface protein (SspA) sequence which has homology to CluA (SEQ ID NO: 5);

FIG. 6 illustrates the *Streptococcus mutans* Pac protein sequence which has homology to CluA (SEQ ID NO: 6);

FIG. 7 illustrates the *Lactococcus lactis* InbA sequence (SEQ ID NO: 7);

FIG. 8 illustrates the *Lactobacillus johnsonii* HtrH like proteinase (SEQ ID NO: 8);

FIG. 9 illustrates the *Lactobacillus acidophilus* HtrH like proteinase (SEQ ID NO: 9);

FIG. 10 illustrates the *Streptococcus thermophilus* exported proteinase (SEQ ID NO: 10);

FIG. 17 shows SEM pictures of biofilm formation of *Lactococcus lactis* LM2302: FIG. 18A is the control; FIGS. 18B-C are with casein; FIGS. 18D-E are with proteinase; and FIGS. 18F-G are with PMSF FIGS. 19A-B are the control; FIGS. 19C-D are with casein; FIGS. 19E-F are with PMSF.; and FIGS. 19G-H are with proteinase;

FIG. 20A-B are the control; FIGS. 20C-D are with casein; FIGS. 20E-F are with PMSF; and FIG. 20G is with proteinase.

DETAILED DESCRIPTION OF EMBODIMENTS OF THE INVENTION

Figure 11:
FIG. 11 shows attached versus detached biofilms, left: LM2301 and right: HW002.

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

This invention is based on the unexpected discovery that one or more bacterial proteins and/or proteinases from lactic acid bacteria and other bacteria and homologs of these proteins and proteinases, for example the lactic acid bacteria *Lactococcus lactis*, function to prevent or diminish the association between bacteria in biofilms, thus presenting the possibility for use of the bacteria, or one or more of the bacterial proteins and/or proteinases, alone or combined, to reduce the formation of and/or at least partially remove biofilms.

In accordance with embodiments of the present invention, bioengineered bacterial organisms are provided. The bioengineered bacterial organisms are bioengineered to express two or more of the bacterial proteins and/or proteinases of interest. The bacterial proteins and/or proteinases of interest may be any suitable bacterial protein or proteinase that interact with surface molecules on target bacterial cells, such as pathogenic bacteria, or otherwise undesirable bacteria, to prevent surface attachment of the cells and interaction between the cells. Suitable proteins and proteinases include, but are not limited to: *Lactococcus lactis* HtrA SEQ ID No: 1 (FIG. 1), *Lactococcus lactis* PrtP SEQ ID No: 2 (FIG. 2), *Lactococcus lactis* PrtM SEQ ID No: 3 (FIG. 3), *Lactococcus lactis* CluA SEQ ID No: 4 (FIG. 4), *Streptococcus gordonii* SspA SEQ ID No: 5 (FIG. 5), *Streptococcus mutans* Pac SEQ ID No: 6 (FIG. 6), *Lactococcus lactis* InbA SEQ ID No: 7 (FIG. 7), *Lactobacillus johnsonii* HtrH-like proteinase SEQ ID No: 8 (FIG. 8), *Lactobacillus acidophilus* HtrH-like proteinase SEQ ID No: 9 (FIG. 9), and *Streptococcus thermophilus* exported proteinase SEQ ID No: 10 (FIG. 10). It will be understood that suitable variants of SEQ ID Nos:1-10 may also be used. Additionally, suitable homologs may be used. These proteins and proteinases will be discussed further herein. Bioengineered bacterial organisms can promote the inhibition or removal of a biofilm. It will be understood that these bacteria can be constituted in formulations as are well known in the art for achieving shelf-stability, and may be provided in the form of non-ingestible or ingestible products for use in treating inert or biological surfaces.

It will be understood that the bioengineered bacterial organisms can be formed in any suitable manner. For example, the bioengieered bacteria can comprise variant forms of *Lactococcus lactis*, other lactic acid bacteria, or other bacteria as further described herein, or combinations of these. In other examples, the bacteria can comprise other non-pathogenic bacteria containing polynucleotide vectors which include appropriate promoters in operable communication with one or a combination of polynucleotides encoding one or more of the proteins or proteinases of interest. It will be further understood that the bioengineered organisms can be provided in any suitable manner, including, but not limited to in suspension, immobilized on an abiotic matrix, in a gum, or in a cheesy tooth paste.

In accordance with additional embodiments of the present invention, compositions that at least partially inhibit or at least partially remove a biofilm are provided. The compositions comprise an effective amount of two or more proteins or proteinases and/or bacteria that overexpress at least one of the proteins or proteinases of interest. For example compositions that comprise an effective amount of two or more of isolated *Lactococcus lactis* HtrA, *Lactococcus lactis* PrtP, *Lactococcus lactis* PrtM, *Lactococcus lactis* CluA, *Streptococcus gordonii* SspA, *Streptococcus mutans* Pac, *Lactococcus lactis* InbA, *Lactobacillus johnsonii* HtrH-like proteinase, *Lactobacillus acidophilus* HtrH-like proteinase, and *Streptococcus thermophilus* exported proteinase and/or bacteria overexpressing one or more of *Lactococcus lactis* HtrA, *Lactococcus lactis* PrtP, *Lactococcus lactis* PrtM, *Lactococcus lactis*

CluA, *Streptococcus gordonii* SspA, *Streptococcus mutans* Pac, *Lactococcus lactis* InbA, *Lactobacillus johnsonii* HtrH-like proteinase, *Lactobacillus acidophilus* HtrH-like proteinase, and *Streptococcus thermophilus* exported proteinase.

It will be understood that the bacteria can be any suitable bacteria. For example, the bacteria may be wild-type or variant forms of *Lactococcus lactis*, other lactic acid bacteria, or other bacteria as further described herein, or combinations of these. In some embodiments, the bacteria comprise other non-pathogenic bacteria containing polynucleotide vectors which include appropriate promoters in operable communication with one or a combination of polynucleotides encoding one or more of the proteins and/or proteinases of interest.

In yet other embodiments, the invention provides compositions for at least partially preventing or removing biofilms. The compositions one or more antibodies directed to one or more of *Lactococcus lactis* CluA, *Streptococcus gordonii* SspA, and *Streptococcus mutans* Pac or the receptors therefore. Additionally, the compositions can further comprise one of more of *Lactococcus lactis* HtrA, *Lactococcus lactis* PrtP, *Lactococcus lactis* PrtM, *Lactococcus lactis* CluA, *Streptococcus gordonii* SspA, *Streptococcus mutans* Pac, *Lactococcus lactis* InbA, *Lactobacillus johnsonii* HtrH-like proteinase, *Lactobacillus acidophilus* HtrH-like proteinase, and *Streptococcus thermophilus* exported proteinase.

The compositions can comprise any suitable additives and/or additional active ingredients. For example, the compositions can further include surfactants, therapeutics, and/or antimicrobials. In other embodiments, the compositions may further comprise other additives such as colorants, stabilizers, flavorings for use in treatment or prevention of biofilms in the oral cavity. In yet other such embodiments, the compositions may further comprise other additives such as colorants, stabilizers, antimicrobials, perfumes, and the like for use in treatment or prevention of biofilms in industrial or residential settings. In still yet other such embodiments, the compositions may further comprise other additives suitable for use in treatment or prevention of biofilms in the healthcare delivery or medical device handling settings. It will be understood that the compositions can be provided in any suitable manner, including, but not limited to in suspension, immobilized on an abiotic matrix, in a gum, or in a cheesy tooth paste.

In accordance with yet further embodiments, the compositions and/or bioengineered bacteria may be used to reduce the formation of biofilm on a surface and/or at least partially remove a biofilm. For example, methods for preventing or removing a biofilm can comprise contacting a biofilm or a biofilm surface with a composition comprising at least one of an organism that overexpresses one or more of *Lactococcus lactis* HtrA, *Lactococcus lactis* PrtP, *Lactococcus lactis* PrtM, *Lactococcus lactis* CluA, *Streptococcus gordonii* SspA, *Streptococcus mutans* Pac, *Lactococcus lactis* InbA, *Lactobacillus johnsonii* HtrH-like proteinase, *Lactobacillus acidophilus* HtrH-like proteinase, and *Streptococcus thermophilus* exported proteinase, isolated *Lactococcus lactis* HtrA, isolated *Lactococcus lactis* PrtP, isolated *Lactococcus lactis* PrtM, isolated *Lactococcus lactis* CluA, isolated *Streptococcus gordonii* SspA, isolated *Streptococcus mutans* Pac, isolated *Lactococcus lactis* InbA, isolated *Lactobacillus johnsonii* HtrH-like proteinase, isolated *Lactobacillus acidophilus* HtrH-like proteinase, and isolated *Streptococcus thermophilus* exported proteinase such that biofilm formation on the biofilm surface is reduced or the biofilm is at least partially removed.

In other embodiments, the composition can also include one or more antibodies to one or more of *Lactococcus lactis* CluA, *Streptococcus gordonii* SspA, and *Streptococcus mutans* Pac or the receptors therefore. In yet further embodiments, the composition can comprise one or more such antibodies.

The methods may be used to contact any suitable surface and/or biofilm. For example, the step of contacting can comprise contacting an oral surface and/or a biofilm on an oral surface or an abiotic surface and/or a biofilm on an abiotic surface. Additional biotic surfaces and/or biofilms on biotic surfaces can be contacted. The contact can occur in any suitable mainner for any length of time. For example, the composition can contact the biofilm for a period of time such that the biofilm is at least partially removed. In another example, the composition can contact the biofilm surface for a period of time such that biofilm formation on the biofilm surface is reduced.

In certain embodiments, the compositions comprising bacteria expressing one or more of CluA, PrtP and HtrA are used to prevent or treat biofilms of the oral cavity. In other embodiments, the compositions are used to treat inert, abiotic surfaces, such as equipment, tables, instruments, storage and mixing vessels, and the like, used in a variety of industries, including healthcare, medical devices, food preparation and storage, and others. More generally, in the various embodiments described herein the methods and compositions are suitable for treating or preventing biofilms on a wide variety of surfaces and in a wide range of contexts.

Having discussed particular embodiments of the invention herein, particular proteins and proteinases of interest, along with particular modes of action, will now be discussed. Although the bacteria *L. lactis* are abundant in fermented foods (such as cheese) as fermentation starter cultures, they are rarely found as residential organisms in the oral ecosystem. A model organism *L. lactis* HW002 is a clumping transconjugant derived from mating the donor strain ML3 and the recipient LM2301. Comparing to the donor strain ML3, this strain has overexpressed CluA protein, which is believed to be a key biofilm attribute. Besides CluA, a second plasmid encoded element is involved in *L. lactis* biofilm from initiation to detachment.

FIG. 11 shows that LM2301 formed a light biofilm, but the transconjugant HW002 (LM2301 received the Lac plasmid and the sex factor) not only exhibited facilitated biofilm formation (thicker) but detachment as well. Another key component encoded by the Lac plasmid is the proteinase PrtP. The cloned and sequenced HW002 prtP gene has high homology with published proteinases from all lactic acid bacteria such as *Lactobacillus casei, Streptococcus thermophilus, Lb. acidophilus* etc, as well as streptoccal proteinases, including those from oral streptococci (Appendix A).

Figure 12:
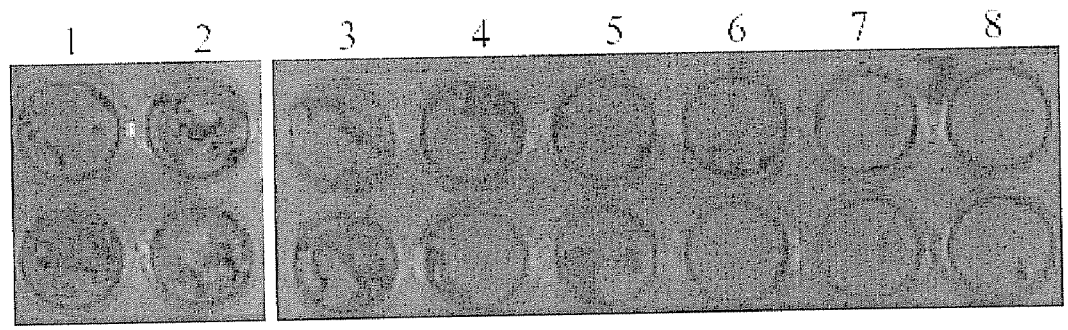
FIG. 12 shows *L. lactis* HW002 Bfm with (1) 10 mM PMSF, (2) 5 mM PMSF, (3) 1 mM PMSF, (4) no addition, (5) 200 µg proteinase, (6) 400 µg proteinase, (7) 1 proteinase, (8) 2 mg proteinase.

HW002 exhibited facilitated biofilm formation as well as detachment phenotype. CluA is highly homologous to key oral streptococcal surface adhesins involved in biofilm formation. FIG. 12 shows that exogenous proteinase treatment can simulate the function of PrtP and facilitate biofilm removal. Adding proteinase inhibitor has the opposite effect. Protease treatment affecting the functionality of the key cell surface proteins such as CluA facilitated biofilm detachment. The lactococcal surface proteases such as PrtP and HtrA are the matching endogenous molecules that are responsible for degradation of the lactococcal proteins including those involved in biofilm formation. Other lactic acid bacteria such as *lactobacilli* also carry the proteinases but are able to integrate into oral ecosystem. The major difference is lactococcal PrtP is encoded by the plasmid therefore the dose of expression is much higher than other lactic acid bacteria (LAB) as well as streptococci, where the prtP gene is chromosomal located (single copy). Genome sequence search indicated that several LAB strains such as *Lb. casei* and *Lb. helveticus* carry multiple copies of surface proteinases in the chromosome, therefore these LAB strains will have facilitated biofilm detachment as well.

Figure 13:
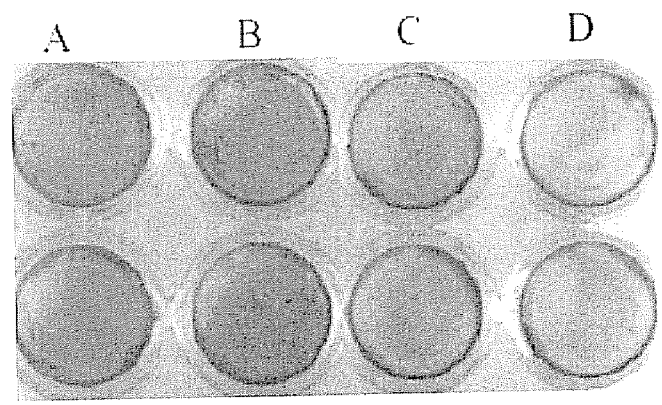
FIG. 13 shows detachment of 48 h staphylococcal biofilms by lactococci. A, *Staphylococcus* spp. HLZ biofilm (no treatment); B, Staph biofilm+*Pseud.* spp. HLY, 2 h 30° C. (control); C, Staph biofilm+*L. lactis* LM2301, 2 h 30° C.; D, Staph biofilm+*L. lactis* HW002, 2 h 30° C.

Environmental stress that can trigger Htr proteinases expression will also facilitate biofilm detachment. HW002 carrying the active ingredients are also functional in breaking biofilms by other organisms besides lactococci (FIG. 13). The overwhelming activities of proteinase activities (both plasmid and chromosomal located) are components in biofilm detachment and are believed to be responsible for the observed lacking of lactococci in oral ecosystem. Besides the proteases, the CluA receptor or antibody, as well as the exogenous functional domains of CluA and CluA can serve as active ingredients to prevent biofilm development and facilitate biofilm detachment. These enzymes and surface protein adhesin analogues and their receptors are also abundant in other foodborne lactic acid bacteria, including but not limited to, *Streptococcus thermophilus* and Lactobacilli. For example, additional adhesins, HtrA homologs, and cell surface proteinases such as *Streptococcus gordonii* SspA, *Streptococcus mutans* Pac, *Lactobacillus johnsonii* HtrH-like proteinase, *Lactobacillus acidophilus* HtrH-like proteinase, and *Streptococcus thermophilus* exported proteinase can prevent biofilm development and facilitate biofilm detachment. These organisms, as well as their functional components, can be used as active ingredients in the compositions of the present invention. For example, the compositions can be provided in the form of dental hygiene products, including, but not limited to, cheesy tooth masks or gums containing active ingredients, daily wrapped on teeth for certain period of time for treatment, to treat oral biofilms and facilitate their removal.

In addition, a homology of lacto-N-biosidase or beta-N-acetylhexosaminidase (InbA) is also found in *L. lactic* IL1403 genome and *Lactobacillus casei,* making *L. lactis* and other foodborne lactic acid bacteria candidates to remove biofilms that can be directly used in human (Appendix C). These organisms, as well as their functional components, can be used as active ingredients in dental hygiene products, including, but not limited to, cheesy tooth masks or gums containing active ingredients, daily wrapped on teeth for certain period of time for treatment, to treat oral biofilms and facilitate their removal. It will be understood that these bacteria, bacteria bioengineered to express the proteins and/or proteinases of interest, and the proteins or proteinases of interest themselves can be used in the compositions and methods of the present invention. It will be further understood that the compositions and methods of the present invention can be used to treat biotic and abiotic biofilms. These biofilms may be found in the human body, in industrial settings, and/or in residential settings. It will also be understood that the compositions and methods can be selected to at least partially remove a particular biofilm or at least partially prevent the formation of a particular biofilm. Not only the microorganisms expressing the active ingredients but also the active ingredients alone or in abiotic matrixes such as magnetic beads or glass beads and any suitable methods of immobilization, can also be used in compositions and methods for biofilm prevention and/or removal.

Figure 14:
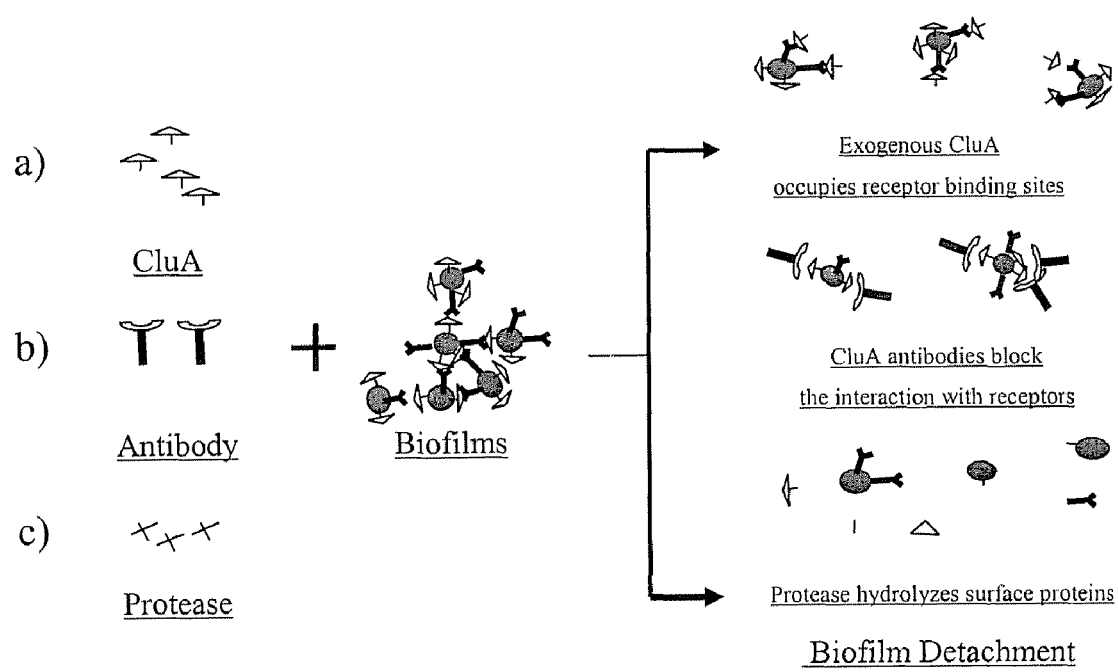
FIG. 14 illustrate strategies for biofilm detachment.

FIG. 14 illustrates one of the biofilm interfering working mechanisms. The mechanism is based on a number of roles of particular proteins and proteinases in biofilm formation and detachment. For example, surface adhesins are believed to play a role in microbial biofilm development. Adhesins may act to inter-connect the cells and to stabilize the biofilm structure in hydrodynamic biofilm systems. It is believed that modification of the surface adhesins can affect the shape and structure of the formed biofilm. It is further believed that cell-cell adherence is a key player in determining the maturation and shape of biofilm.

Certain *Staphylococcus aureus* strains carry a cell wall-associated, 2276-aa biofilm-associated protein (Bap). Bap is involved in *Staphylococcus* pathogenesis, and all isolates carrying Bap are strong biofilm producers. The staphylococcal clumping factors ClfA and ClfB are fibrinogen-binding proteins, and ClfA mediates staphylococcal adherence to host extracellular matrix components as well as abiotic surfaces. Many cell surface proteins involved in adherence, such as Esp, Bap and ClfA, contain core domains with tandem repeats which may be essential for attachment to surfaces or host components. Many of the cell surface proteins are covalently anchored to the cell wall peptidoglycan and possess a carboxyl-terminal LPXTG sequence motif. An enzyme (sortase) is involved in cleaving the LPXTG sequence and covalently attaching the surface protein with C-terminal LPXT to cell wall peptidoglycan.

Co-aggregation describes the phenotype of cell aggregation caused by mixing a strain carrying the adhesin and another pairing strain carrying the cognate receptor. If a bacterial strain carries both the adhesin and the cognate receptor, cell clumping or self-aggregation often occur. Cell surface adhesin-receptor mediated interaction plays an essential role in recruiting compatible organisms for ecosystem expansion. For instance, the *Streptococcus gordonii* surface antigens SspA and SspB are known to mediate coaggregation with other oral bacteria. Certain surface components such as the staplhylococcal biofilm-accumulation-associated protein (AAP) have greater impact on Bfm than other adhesins. Staphylococcal strains expressing AAP produce significantly larger amounts of biofilm than strains without this antigen. In *L. lactis,* the clumping protein CluA can also considerably facilitate biofilm development. Biofilm formed by lactococcal strain with induced over-expression of the clumping protein CluA is 7-8 times thicker than without.

Besides adhesins, the involvement of autolysins in biofilm formation is believed to occur in several bacteria. The *S. epidermidis* major autolysin AtlE is a multidomain protein composed of an N-terminal signal peptide, a propeptide (PP), an amidase domain, three highly cationic repeats, and the glucosaminidase domain. In addition to the signal peptide processing, AtlE is also processed by an extracellular protease. Partial processing of AtlE generates degraded products of various sizes. The atlE mutant by transposon mutagenesis is defective in primary adhesion to polystyrene. Although atlE mutation does not have a major impact on cell viability, the cell separation after division is severely impaired, which leads to cell clusters due to covalent interlinking among cells.

It is further believed that extracellular proteolytic enzymes may have roles in biofilm formation. For example, in *Bacillus subtilis,* extracellular proteases appear to be essential for swarming motility, a feature related to the strain's biofilm formation capability. It is believed that protease activities may be essential for proper biofilm formation.

Lactococci are fastidious organisms with multiple amino acid auxotrophies. An efficient proteolytic system to degrade and transport exogenous proteins and peptides is essential for these organisms to grow on their natural habitant rich in protein substrates such as meat, milk and vegetables. The *L. lactis* proteolytic system contains several functional components, including the cell wall associated serine proteinase PrtP and its maturation protein PrtM, the oligopeptide transport system (Opp), intracellular peptidases, di-, tri-peptidases, and di-, tri-peptide transport systems. The proteinase PrtP and the maturation protein PrtM have been identified associated with plasmids in many lactococcal strains and both plasmid- and cluomosomal-located Opp system has been reported. PrtP from different strains may vary in the milk protein casein hydrolyzing specificity. It is believed that PrtP is also involved in processing cell surface proteins.

An HtrA homolog is also believed to be a general cell surface protease of certain lactococcal strains. HtrA is a stress-inducible cell envelope protease with confirmed role in housekeeping in *E. coli*. It is a serine protease and is induced and believed essential for growth at high temperature. Lactococcal HtrA is essential for growth at very high temperatures and is involved in surface proteolysis. Under normal growth conditions, the lactococcal surface protease HtrA is involved in abnormal protein degradation, pro-peptide processing and native protein maturation.

EXAMPLES

Example 1

Figure 15:
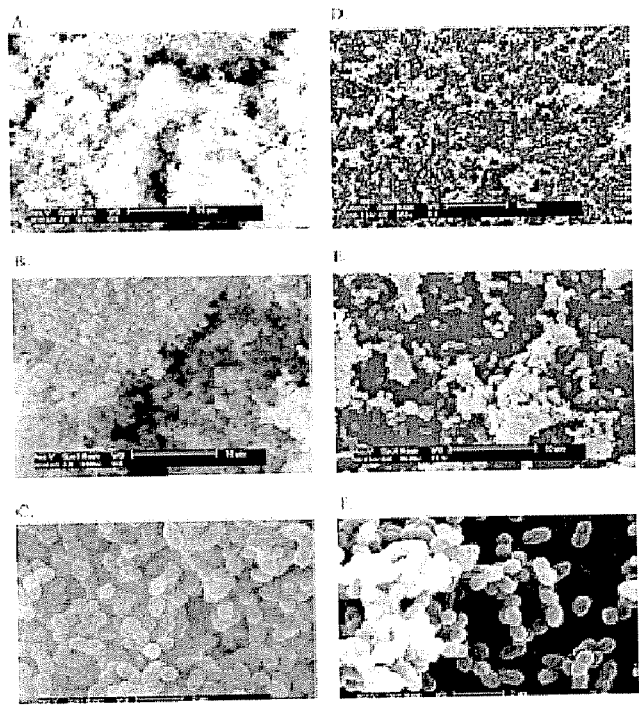
FIG. 15 show SEM pictures of biofilm formation by *L. lactis* HL3A. A: With nisin induction. D: Without nisin induction. B, C and E, F: Regional magnification of A and C.

To confirm the role of CluA in lactococcal biofilm formation, the cluA gene was cloned into the expression vector pMSP3535, downstream of the nisA promoter. The recombinant plasmid was electroporated into ML3 and LM2301, and the transformants were designated HL3A and HL2301A, respectively. The expression of CluA protein in these strains was induced by external nisin signal and confirmed by SDS-PAGE (data not shown). Strains HL3A and HL2301A both exhibited cell aggregation with nisin induction. SEM study showed that both strains also exhibited enhanced Bfm with nisin induction in comparison with the non-induced cultures (FIG. 14 and FIG. 15). Confocal laser scanning microscopy illustrated that the Bfm by CluA-expressed HL3A with nisin induction was 7-8 times thicker than that by the same strain without induction (data not shown). These results confirmed that CluA was the clumping factor, and strongly supported our hypothesis that CluA is a key element in lactococcal Bfm. Increased expression of CluA, triggered by the conjugation event in *L. lactis*, facilitated lactococcal biofilm formation.

Figure 16:
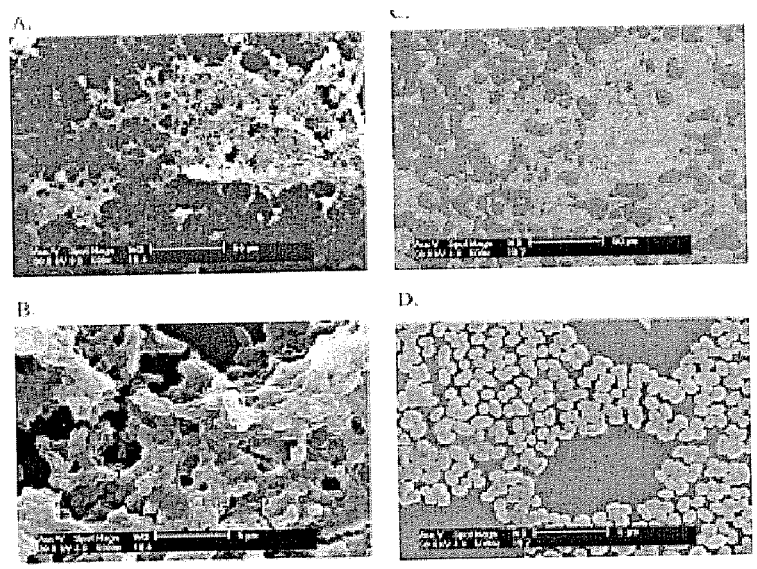
FIG. 16 shows SEM pictures of biofilm formation by *L. lactis* HL2301A. A and B: With nisin induction. C and D: Without nisin induction.

Despite the fact that clumping HL2301A (expressing of CluA) developed a 3-dimensional biofilm structure with nisin induction, which was absent by the same strain without the inducer (FIG. 15A-B), the biofilm structure was more localized colonies instead of a well developed network as illustrated by HW002 (FIG. 11E-F) and HL3A (FIG. 14A-B). With HW002, we consistently observed the attachment of the cell clumps to the surface, followed by the rapid expansion of cell clumps into a connected network. A striking feature of HW002 and HL3A is that they form thick biofilms, but these biofilms are easily detached as sheets from the surface of microtiter plates (FIG. 16). Since the only difference between HW002 and HL2301A are the genes encoded by pSK08 and pRS01, the data suggested that other than CluA, pSK08 and pRS01 carry additional Bfm factor(s) that also contributed to proper biofilm growth to detachment.

Example 2

Roles of Exogenous Protease and Protease Inhibitor on *L. lactis* Biofilm Development The difference in biofilm growth and detachment observed between the CluA-producing strains HL2301A and HW002 shared certain similarity with the biofilm phenotypes of *A. actinomycetemcomitans* strains due to the mutation in the dispersin B gene (dspB). As outlined in the literature, a group of macromolecules with the potential to affect biofilm development but has not been explored in *L. lactis* are proteases located on the cell surface. Because cell surface proteins play a key role in lactococcal Bfm, proteolytic systems could be involved in processing proteinacous cell surface component(s) that are essential for Bfm. Indeed both PrtP and its maturation protein PrtM are located on pRS01. Although PrtP is known as the major proteinase involved in breaking down the milk protein casein to support the growth of the microorganisms, evidence showed that PrtP also affected autolysin AcmA activity, which was a Bfm attribute. Therefore it is plausible that cell surface protease PrtP may not only be essential for nutrient supply, but are also involved in processing other cell surface proteins, including those essential for Bfm, from growth to detachment.

To investigate the potential involvement of protease in lactococcal Bfm, biofilm formation by the pSK08 and pRS01-containing strains ML3 and HW002 at the presence and absence of proteinase K and the serine protease inhibitor PMSF was examined. Ten ml of overnight cultures of lactococcal strains ML3 and HW002 were collected by centrifugation, and the cell pellets were resuspended in 1 ml of 100 mM NaH2PO3 (pH 7.0). One hundred μl of the cell suspension was inoculated into 1 ml of M17-L broth in each well of the 24-well microtiter plate. Serially diluted proteinase K and the serine protease inhibitor PMSF were added to the media to investigate the protease dose effect on Bfm. The mixtures were incubated at 30° C. for 5 h. As showed in FIG. 12, at the presence of 2 mg or 1 mg of proteinase K, HW002 cell clumps do not attach to the surface and no biofilm is observed; with 400 μg or 200 μg of proteinase K, a sheet of biofilm on the surface can be observed, and the increase of the attachment intensity corresponds to decreased concentration of proteinase K. Without exogenous protease, HW002 forms thick biofilm but the biofilm still can be detached from the surface by a simple rinse. The more the protease inhibitor PMSF present in the medium, the tighter the biofilm attached to the surface. Strain ML3 exhibited similar phenomenon except that the biofilm formed was much thinner than that by HW002 (data not shown). These data strongly indicate that lactococcal protease activity has a key role in the facilitated biofilm growth and detachment.

Example 3

Presence of Endogenous Proteases in *L. lactis*

Using prtP and htrA specific primer pairs [5'AAAGT-TCAGCAGCAAG3' (SEQ ID NO: 11) (prtF), 5'CCG-GCAGTTTGTTGGGTG3' (SEQ ID NO: 12) (prtR), 5'GGCAAAAGCTAATATAGG3' (SEQ ID NO: 13) (hrtA RTF), 5'GTATTGACATTTACCG3' (SEQ ID NO: 14) (htrA RTR)] the presence of prtP and htrA in ML3, LM2301 and HW002 was examined. The PCR results clearly showed the presence of htrA in all three strains and prtP in ML3, HW002 and absent in LM2301 (data not shown).

Example 4

Homology of CluA

Homology search of CluA amino acid sequences (GI: 1351100) against the GenBank database revealed that it has significant sequence homology (50% or greater similarity, 30% or greater identity) with regions of genes encoding various surface proteins (antigens) including SpaA from *Streptococcs downei* (*sobrinus*), PaaA from *S. criceti*, surface antigen I/II Pas of *S. intermedius*, salivary agglutinin receptor precursor of *S. sanguis* (*sanguinis*), SspA, SspB, Ssp-5 of *S. gordonii*, SpaP, surface antigen I/II precursor, surface antigen Pac, saliva-interacting protein precursor of *S. mutans*, Pac protein homolog/SpaA protein homolog of *S. oralis*, agglutinin receptor of *S. agalactiae*, cell surface protein B of *S. salivarius*. Since many oral streptococci also carry the receptors for these adhesins as evidenced by the auto-aggregation phenotype exhibited in strains such as *S. mutans* UA159 and *S. gordonii* DL1, there is a possibility that the lactococcal adhesin and receptors may cross-react with those in streptococci. Therefore, lactococci have the potential to be involved in the oral ecosystem through adhesin-receptor interaction with the oral microbial residents.

Example 5

Lactococcal Cells Facilitate Detachment of Biofilms Formed by *Staphylococci*

Overnight cultures of *L. lactis* HW002 and LM2301 were added to a 48 h-biofilm by *Staphylococcus* spp. HLZ and incubated at 30° C. for 2 h. The biofilm residues were examined using the crystal violet rapid assessment assay. FIG. 13 showed that most of the staphylococcal biofilms were removed by co-incubation with HW002. LM2301 also helped detaching the biofilm but the efficiency was much lower than HW002. These results suggest that lactococcal strains carry functional element(s) that can facilitate staphylococcal biofilm removal. However the activity by the plasmid-cured strain LM2301 is much less than HW002, which contains both pRS01 and pSK08.

Example 6

Examination of Effect of Casein, Proteinase, and PMSF on Biofilm Formation of Various Lactococcal Strains The cells of over night cultures of lactococcal strains were collected by centrifugation and resuspended in M17 broth. The cultures were inoculated into 24-well microtiter plate wells with 1 vol of fresh M17 broth. Designated amount of exogenous casein, proteinase and proteinase inhibitor PMSF were added to the culture. All samples were incubated at 30 C for 24 h. The biofilms attached to the surface were rinsed with PBS, fixed with formaldehyde and dehydrated as described previously (Luo et al., 2005) and subjected to Scanning Electron Microscopy analysis.

Figure 18:
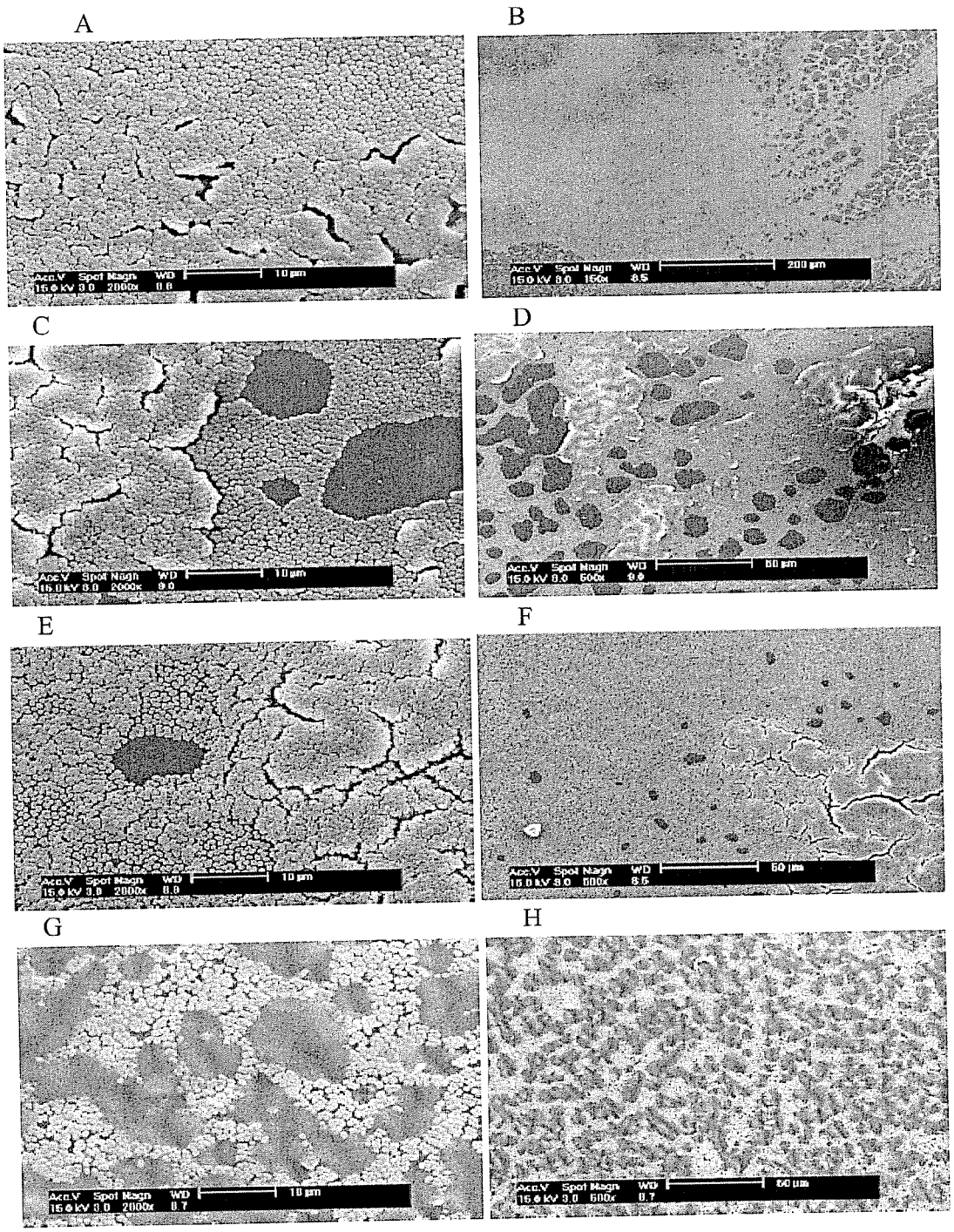
FIG. 18 shows SEM pictures of biofilm formation of SK11-1, a plasmid cured derivative of SK11.
Figure 19:
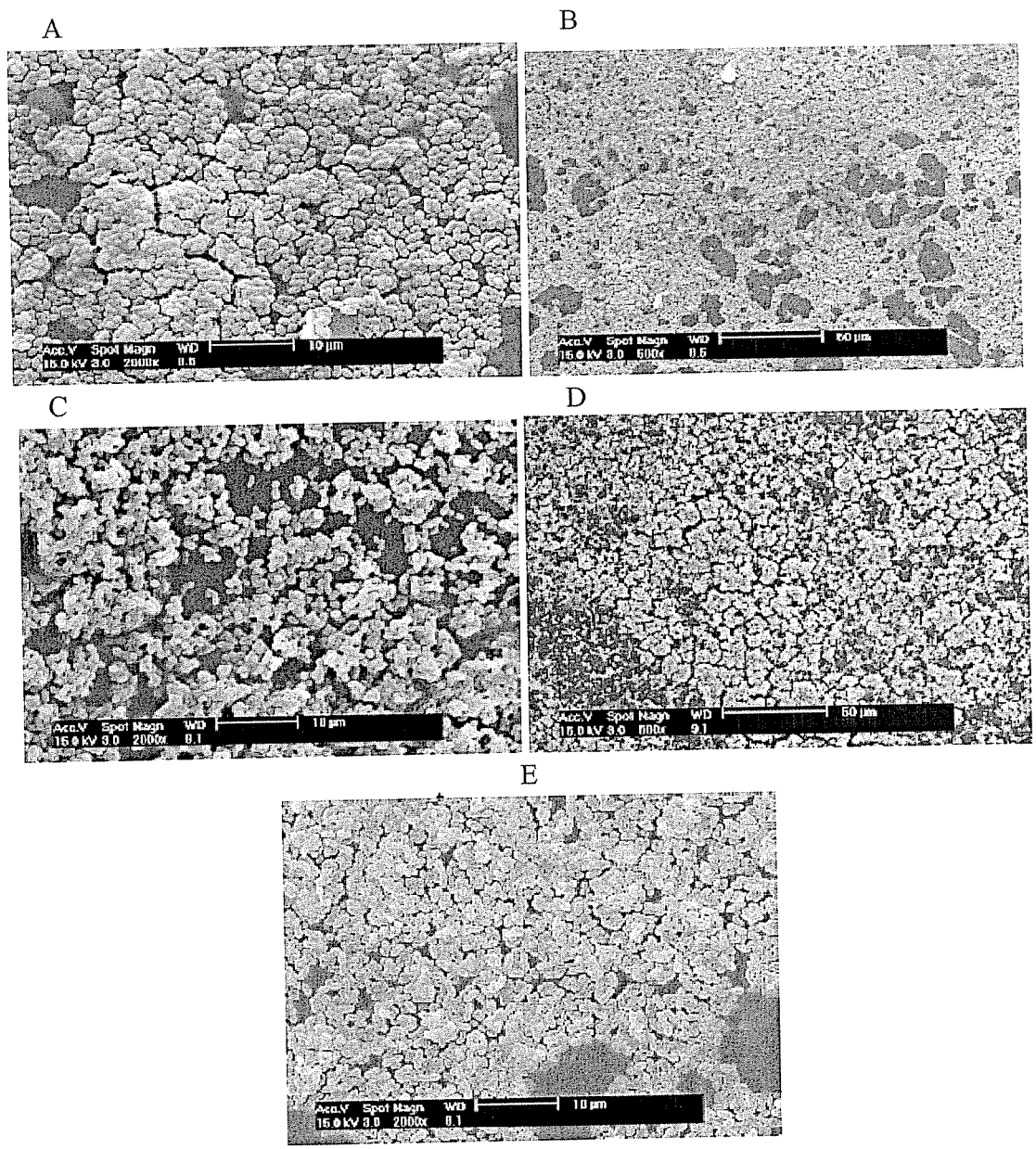
FIG. 19 shows SEM pictures of biofilm formation of SK11, a parental strain that carries multiple plasmids including those encoding for proteinases PrtP and PrtM.

*Lactococcus lactis* LM2302: plasmid cured strain is shown in FIGS. 17A-E. FIG. 17A is the control. FIGS. 17B-C are with casein. FIGS. 17D-E are with proteinase. FIGS. 17F-G are with PMSF. SK11-1 is a plasmid cured derivative of SK11 and results are shown in FIGS. 18A-H. FIGS. 18A-B are the control. FIGS. 18C-D are with casein. FIGS. 18E-F are with PMSF. FIGS. 18G-H are with proteinase. SK11 is a parental strain that carries multiple plasmids including those encoding for proteinases PrtP and PrtM and results are shown in FIGS. 19A-G. FIG. 19A-B are the control. FIGS. 19C-D are with casein. FIGS. 19E-F are with PMSF. FIG. 19G is with proteinase. The overall biofilm development of SK11 is faster than for the other two strains. Adding casein can enhance the biofilm development. Inhibiting the proteinase activity by PMSF can also facilitate the development of a biofilm structure. Adding proteinase on the other hand slows the development of the network as illustrated in FIGS. 17D-E and FIGS. 18G-H. In the case of SK11, proteinase just reduced the thickness of the biofilm as shown in FIG. 19G.

Prophetic Examples

Prophetic Example 1

Clone and Express of prtP

The DNA fragment containing the prtP and prtM genes (75) will be cloned into the nisin inducible vector pMSP3535 and the recombinant plasmid pMSP3535CluA (downstream of cluA). These plasmids will be electroporated into LM2301. Bfm of HL2301CluA (preliminary study), HL2301CluAPrtMP and HL2301PrtMP will be examined using the crystal violet staining method and confirmed with SEM. We anticipate HL2301CluAPrtMP will be comparable in Bfm to HW002. The comparison among Bfm by HL2301PrtMP, ML2301, HL2301CluA and HL2301CkuAPrtMP will illustrate whether PrtP by itself is sufficient or it has to work coordinately with CluA to enhance lactococcal biofilm development. PrtP crude extract can be obtained by incubating *L. lactis* strains in Ca2+ free buffer. However, purified PrtP is required to study the function of PrtP without the interference by other proteins in the crude extract. Thus, we will make a prtP construct using the vector pMSP3535 where a hexahistidine metal-binding site is included for easy purification purpose. The 6× His-tag will be introduced into the C-terminus of PrtP (around position 1127, associated with membrane attachment) using the approaches as described for constructing the CluA secretion plasmid (65). The catalytic domain of PrtP is located near the N-terminus. Therefore the engineered PrtP will retain the catalytic activity but more enzyme molecules will be released to the medium instead of attaching to the membrane. After purification, the His-tag can be cleaved from the recombinant protein by thrombin. A similar construct for secreted CluA has already been made in *E. coli* in our laboratory. Thus, we are fully capable of making this type of constructs. This pMSP3535PrtPHis will be electroporated into ML3 that carries the functional maturation protein PrtM, and consequently the recombinant PrtP precursor can be processed by the PrtM in the host for full activity. The expression of the recombinant PrtP by transformant ML3HisPrtP will be induced by nisii. PrtP will further be isolated and purified by the Ni-affinity column. The expression level and purity of the recombinant protein PrtA will be verified by SDS-PAGE.

Prophetic Example 2

Construct prtP Knockout Mutant and Examine its Bfm

Restoration of comparable Bfm in HL2301CluA by the cloned prtP gene would indicate that PrtP is an important player in Bfm. To examine whether other factors (besides CluA and PrtP) encoded by pSK08 and pRS01 may also have an effect on Bfm, we will construct prtP knockout mutant and examine the impact of the mutation on Bfm. The lactococcal suicide plasmid pTRK28 derivative pTRK146 (59), will be used to construct the mutant. An internal fragment of prtP will be amplified by PCR and cloned into pTRK146. The recombinant plasmid will be electroporated into *E. coli* host strain DH5a and the Cm-resistant transformant will be selected. The plasmid p002DPrtP will be extracted from the transformant and then be electroporated into HW002, and the Em-resistant transformant HW002DPrtP will be isolated on M17-Em plate. Because pTRK146 does not carry the Gram-positive replication of origin and the fragment containing the IS element was deleted from pTRK28, the most likely event when the resistance gene is expressed is due to a cross-over inserting the plasmid p002DPrtP into the chromosomal DNA via homologous recombination. This strategy has been successfully used to knockout the htrA gene (56). The successful insertion of the plasmid into the prtP gene will be confirmed by PCR using one primer derived from the Em gene and the other primer from the upstream sequence from the inserted prtP fragment, or Southern hybridization using the prtP gene fragment as the probe. The transformant HW002DPrtP will be evaluated for Bfm. If HW002DPrtP exhibits a similar Bfm phenotype as HL2301 CluA, it will suggest that PrtP is the sole factor missing in HL2301CluA for the facilitated biofilm growth and detachment as observed in HW002. If HW002DPrtP exhibits stronger biofilm network formation than HL2301 CluA but still less than HW002, it will indicate that there are additional factor(s) encoded by pRS01 and pSK08 that contribute to Bfm. If the prtP knockout mutant exhibits stronger Bfm than HW002, it will suggest that PrtP is likely only involved in biofilm detachment, and some other factor(s) are involved in biofilm growth.

To further confirm the linkage between the gene and the phenotype, the plasmid p002DPrtP (Lac+Prt-Emr) will further be transferred to the tetracycline-resistant derivative of LM2301, designated HL2301Tet, by conjugation. The Bfm of the transconjugate will be examined. We anticipate that the Bfm phenotype will also be transferable to HL2301Tet. In our preliminary study, we have already demonstrated that CluA is the clumping factor and a biofilm attribute, but is not a major player in high frequency gene transfer (49). If the recombinant plasmid can be transmitted by conjugation, we will compare the difference in conjugation frequencies between the mating pair A (HW002×HL2301Tet) and mating pair B (HW002DPrtP×HL2301Tet). If pair B has similar frequency as pair A, it will suggest that PrtP does not have an effect on high frequency gene transfer. If pair B has a transfer frequency lower than pair A, it will indicate that PrtP also has a role in high frequency gene transfer, besides Bfm. If we fail to obtain transconjugants due to the prtP knockout, we will isolate the plasmid p002DPrtP and electroporated into HL2301Tet and examine the Bfm of the transformant, to confirm that the Bfm phenotype due to PrtP can be illustrated outside its original host.

Prophetic Example 3

Determine the Role of PrtP in Lactococcal Bfm

To assess the role of PrtP in Bfm, exogenous enzyme will be added to HL2301CluA to examine the Bfm complementation. Purified PrtP (10 mg, 50 mg, 100 mg, and 500 mg, respectively) will be added to 1.5 ml of M17-G broth in microtiter plate wells inoculated with HL2301 CluA (10% overnight culture) at the presence of nisin, and incubated at 30° C. Bfm at 4, 8, and 24 h will be evaluated. We expect to observe restoration of the rapid Bfm growth and detachment phenotype as exhibited by HW002 with higher concentration of exogenous PrtP. With lower concentration of PrtP, biofilm will be attached to the surface of the microtiter plate wells more tightly. We particularly anticipate to observe the biofilm phenotype difference between HL2301CluA (colonies or spots) without PrtP, and the ones with low dose PrtP (biofilm network), which will suggest the role of PrtP in biofilm growth. It is anticipated that biofilm will detach with high dose of PrtP. If this dose effect is observed, it will support the hypothesis that only one enzyme (PrtP) is enough to do the trick. If the dose effect in HL2301CluA is not observed, and exogenous PrtP can only facilitate biofilm detachment by HW002, it will suggest the involvement of additional factor(s) in forming the biofilm network. To further assist understanding of the actual function of PrtP in Bfm, we will examine the potential of PrtP serving as a general protease in processing other cell surface components (besides AcmA) involved in Bfm. Particularly, we will assess whether PrtP can hydrolyze the major surface protein CluA. We will prepare secreted lactococcal CluA using the approach as described by Stentz et al. (2004). Basically, the CluA C-terminus membrane anchor LPXTG will be replaced by a hexahistidine metal-binding site, and the recombinant protein will be secreted to the media instead of attaching to the cell wall. Meanwhile, the His-tagged protein can be purified by Ni-affinity column. Using the primer pair TGTGGGCCCTTT-TAAATGGGCAG (SEQ ID NO: 15) and GAGATCTCTAATGATGATGATGATGAT-GAACCTCTTGGGACAAGTGAACCTGT-GATTTTTTCAATCACG (SEQ ID NO: 16), we have amplified and cloned the cluA fragment into the TA cloning vector (Invitrogen Co., CA) in E. coli. We will further digest and clone the fragment into pMSP3535, in which the expression of the recombinant DNA in lactococci can be induced by nisin. The recombinant plasmid pMS3535CluAHis will be electroporated into LM2301. The synthesis of the recombinant CluA protein will be induced by nisin, and CluA will be isolated and purified by Ni-column following procedures as described previously (65). The expression and purity of the recombinant protein CluA will be verified by SDS-PAGE. The fusion protein will then be sent to Affinity BioReagents (Golden, Colo.) for polyclonal antibody preparation. Purified PrtP (500 mg, 200 mg, 20 mg, 5 mg, respectively), prepared as described previously, will be added to 500 mg of CluA solution in 10 mM Tris buffer (pH 7.0) and incubated at 30° C. for 1 h. The hydrolyzed products are subject to Western Blot analysis using the CluA antibody. Reactions without PrtP or with PMSF will be included as controls. We anticipate to detect multiple CluA degradation products, which will indicate the involvement of PrtP in CluA processing. At the presence of PMSF the proteolytic degradation will be inhibited. This result will suggest the involvement of PrtP in Bfm as a more general protease hydrolyzing multiple surface Bfm factors such as CluA. If CluA degradation products are not detected, it will suggest that PrtP has a rather specific spectrum to process certain surface proteins such as AcmA, and further studies are needed to assess the exact mechanism of PrtP in Bfm.

Prophetic Example 4

Investigate the Potential Involvement of HtrA in Bfm

Our preliminary data showed that LM2301 can also remove staphylococcal biofilm, although at a scale much lower than HW002. This result indicated the possible involvement of a chromosomal factor in Bfm. The stress responsive HtrA is the second surface proteolytic system identified in lactococci. Our preliminary data showed that all the lactococcal strains tested contain the htrA gene. Because of its contribution to stress response and its role in processing secreted proteins, HtrA is considered another potential candidate having a role in Bfm. To test this possibility, we will examine the contribution of HtrA to Bfm using similar approaches described above for PrtP. We will amplify by PCR the htrA gene, clone it into pTRK146 and construct the htrA knockout suicide plasmid pHWDHtrA. The recombinant plasmid will be maintained in *E. coli* and electroporated into HW002, ML3 and LM2301. The Em-resistant transformants will be confirmed by PCR or Southern hybridization for the proper insertion of the plasmid into the htrA gene. The transformants will be evaluated for both growth and viability in M17-G or M17-L, broth at 30° C. and 39° C. Bfm by these strains will also be evaluated, with the expectation that Bfm by LM2301 and LM2301DHtrA will be much slower than that by HW002, ML3 and their mutants. We anticipate that overall htrA mutant strains will be comparable to the wild-types at 30° C., but impaired at 39° C. for both growth and viability in M17 broth. The Bfm difference between the mutants HW002DHtrA, ML3DHtrA and the wild-type strains will illustrate the involvement of HtrA in lactococcal Bfm. It is a common phenomenon that inactivating one protease may trigger over-expression of other proteases in the microbe. Therefore we will also monitor the expression level of htrA in the prtP lockout mutants and vice versa by RT-PCR, using procedures described in our recent publication. The Bfm phenotypic difference between htrA mutants and prtP mutants will further reveal potential difference in functions among the two proteolytic systems. We will also clone the htrA gene into pMSP3535CluA downstream of the cluA gene. The recombinant plasmid pMSP3535CluAHtrA will be electroporated into LM2301. If the transformant does not restore Bfm phenotype as exhibited by HW002, it will indicate a less significant or no role of HtrA in lactococcal Bfm. If the transformant restored Bfm phenotype as HW002, it will suggest that HtrA is required for Bfm. Since HtrA is a stress responsible surface protease and is widely distributed in Gram-positive and Gram-negative bacteria, demonstration of its role in lactococcal Bfm would imply that such a protease may have a universal role in Bfm. The controlled expression of HtrA could therefore be a key process in biofilm development from initiation to detachment. If HtrA is found to be involved in Bfm, we will follow tip with a new proposal using microarray to identify molecular elements and the potential network involved in Bfm under stress conditions (39° C. versus the control at 30° C.).

Prophetic Example 5

Examine the Efficacy of CluA Antibody and CluA Protein in Interfering Lactococcal Clumping and Bfm The preparation of CluA and CluA antibody has been achieved. To determine the efficacy of CluA polyclonal antibody on interrupting biofilms, we will harvest cells from overnight cultures of HL2301CluA (nisin induced) and HW002 by centrifugation, and the cells will be resuspended in 1/10 vol of 100 mM NaH2PO4 buffer. Then 0.5 ml of the cell suspension will be inoculated into 1 ml of M17 broth in microtiter plate wells. The CluA antibody will be serially diluted and mixed with the inoculated cells, and the mixture will be incubated at 30° C. for 4 h. Disruption of lactococcal cell clumps and Bfm by the various titers of CluA antibodies will be assessed using the rapid crystal violet staining assay. We anticipate that CluA antibody above a threshold level will minimize HL2301CluA cell clumping and Bfm by blocking the cell-cell interaction between the adhesin and receptor. Besides CluA antibody, incubating the cell suspension with CluA protein will have similar effect. We expect that cell mobility will rise with the increased concentrations of exogenous CluA, and high concentration of CluA will completely interrupt cell clumping and Bfm. Since such strategy has been proved to be effective in other organisms, the likelihood of success in the lactococcal system is expected to be high.

Prophetic Example 6

Identify Pairing Oral Streptococci Cross-reacting with Lactococcal Surface Antigen(s)

Certain streptococcal strains, such as *S. mutans* UA159 and *S. gordonii* DL1, express both the adhesins and the cognate receptors at high levels and therefore exhibit auto-aggregation. CluA shares significant sequence homology with major adhesins in both organisms. To test the cross-reactivity between lactococcal and streptococcal surface components, we will harvest overnight cultures of UA 159 and DL1 and resuspend the cell pellets in Tris-HCl buffer (pH 6.8). Serially diluted exogenous CluA or CluA antibody will be added to the cell aggregation suspensions and mixed by vortex. We expect to observe the dissociation of the streptococcal cell clumps due to the competitive binding between CluA-streptococcal receptor or CluA antibody-streptococcal adhesin, similar to those illustrated in FIGS. 9a and 9b. This result will suggest the cross-reactivity between the lacotocccal and streptococcal surface components. For those strains that do not exhibit auto-aggregation, we will use (with some modification) the cell coaggregation test (Kolenbrander and Andersen, 1990) to select for streptococcal strains with CluA-compatible receptors. Because *L. lactis* ML3 and its derivatives carry the CluA receptor, over-expression of CluA in these strains results in auto-aggregation. Therefore, these strains cannot be used to screen for streptococcal strains by the co-aggregation test. We will construct a surrogate *Bacillus subtilis* strain where pMSP3535CluA will be introduced into *B. subtilis* strain IG-20 by natural transformation. The CluA over-expression is induced by nisin induction and expression of the CluA in *Bacillus* will be verified by Western Blot analysis using the CluA antibody. The functionality of the nisin genes in *Bacillus* has been demonstrated previously and therefore it is technically feasible to construct the surrogate strain HLbsCluA. HLbsCluA cells (after nisin induction) will be used in the coaggregation assay to screen for streptococcal strains with CluA-compatible receptor(s) following the well-established procedures by others.

Prohpetic Example 7

Investigate the Role of Lactococcal Functional Components in Dispersing Streptococcal Biofilms Pairing streptococcal strains identified above are subject to biofilm disruption study. Biofilms will be cultivated in 24-well polystyrene microtiter plates using procedures established in our laboratory with modifications, by inoculating cultures in SDM medium and incubating the culture at 37° C. with 5% CO2 for 24-48 h without agitation (43). Serially diluted functional lactococcal components CluA, CluA antibody, PrtP, respectively, will be added to individual wells containing the streptococcal biofilms and incubated at 37° C. for 2-4 h. Biofilm detachment will be assessed by the crystal violet staining assay. We anticipate positive roles of these components in negate oral streptococcal Bfm. To further assess the efficacy of lactococcal strains in detaching streptococcal biofilms, we will harvest cells from overnight cultures of HW002, ML3 and LM2301 by centrifugation. The cells will be resuspended in 1/10 volume of coaggregation buffer (1 mM Tris, pH 8.0, 150 mM NaCl, 0.1 mM CaCl2, 0.1 mM MgCl2, 0.02% Na3N). One hundred ml of the cell suspension will be added to each microtiter plate well containing the streptococcal biofilms. The mixture will be incubated at 37° C. with 5% CO2 for 10 min, 30 min and 1 h. Biofilms will be rinsed once with water and the biofilm residues will be assessed by the crystal violet staining assay. It is anticipated that the lactococcal strains will facilitate streptococcal biofilm removal, and strains carry multiple functional components such HW002 will have the most prominent effect. If successful, this could serve as a prototype in developing dental hygiene products such as live culture-containing cheesy paste or mask for routine home treatment.

The present invention should not be considered limited to the specific examples described above, but rather should be understood to cover all aspects of the invention. Various modifications, equivalent processes, as well as numerous structures and devices to which the present invention may be applicable will be readily apparent to those of skill in the art.

It will be obvious to those skilled in the art that various changes may be made without departing from the scope of the invention, which is not to be considered limited to what is described in the specification.

What is claimed is:

1. An isolated bacterium, comprising:
Lactococcus lactis PrtP (SEQ ID NO: 2); and
at least one protease selected from the group consisting of Lactococcus lactis HtrA (SEQ ID NO: 1), Lactococcus lactis PrtM (SEQ ID NO: 3), Lactococcus lactis CluA (SEQ ID NO: 4), Streptococcus gordonii SspA (SEQ ID NO: 5), Streptococcus mutans Pac (SEQ ID NO: 6), Lactococcus lactis InbA (SEQ ID NO: 7), Lactobacillus johnsonii HtrH-like proteinase (SEQ ID NO: 8), Lactobacillus acidophilus HtrH-like proteinase (SEQ ID NO: 9), and Streptococcus thermophilus exported proteinase (SEQ ID NO: 10),
wherein the isolated bacterium is engineered to overexpress Lactococcus lactis PrtP (SEQ ID NO:2) and the at least one protease selected from the group consisting of Lactococcus lactis HtrA (SEQ ID NO: 1), *Lactococcus lactis* PrtM (SEQ ID NO: 3), *Lactococcus lactis* CluA (SEQ ID NO: 4), *Streptococcus gordonii* SspA (SEQ ID NO: 5), *Streptococcus mutans* Pac (SEQ ID NO: 6), *Lactococcus lactis* InbA (SEQ ID NO: 7), *Lactobacillus johnsonii* HtrH-like proteinase (SEQ ID NO: 8), *Lactobacillus acidophilus* HtrH-like proteinase (SEQ ID NO: 9), and *Streptococcus thermophilus* exported proteinase (SEQ ID NO: 10), and
wherein the isolated bacterium promotes the inhibition or removal of a biofilm.

2. The isolated bacterium as claimed in claim 1 wherein the bacterium comprises *Lactococcus lactis* PrtP (SEQ ID NO: 2) and *Lactococcus lactis* HtrA (SEQ ID NO: 1).

3. The isolated bacterium as claimed in claim 1 wherein the bacterium comprises *Lactococcus lactis* PrtP (SEQ ID NO: 2) and *Lactococcus lactis* PrtM (SEQ ID NO: 3).

4. The isolated bacterium as claimed in claim 1 wherein the bacterium comprises *Lactococcus lactis* PrtP (SEQ ID NO: 2) and *Lactococcus lactis* CluA (SEQ ID NO: 4).

5. The isolated bacterium as claimed in claim 1 wherein the bacterium comprises *Lactococcus lactis* PrtP (SEQ ID NO: 2) and *Streptococcus gordonii* SspA (SEQ ID NO: 5).

6. The isolated bacterium as claimed in claim 1 wherein the bacterium comprises *Lactococcus lactis* PrtP (SEQ ID NO: 2) and *Streptococcus mutans* Pac (SEQ ID NO: 6).

7. The isolated bacterium as claimed in claim 1 wherein the bacterium comprises *Lactococcus lactis* PrtP (SEQ ID NO: 2) and *Lactococcus lactis* InbA (SEQ ID NO: 7).

8. The isolated bacterium as claimed in claim 1 wherein the bacterium comprises *Lactococcus lactis* PrtP (SEQ ID NO: 2) and *Lactobacillus johnsonii* HtrH- like proteinase (SEQ ID NO: 8).

9. The isolated bacterium as claimed in claim 1 wherein the bacterium comprises *Lactococcus lactis* PrtP (SEQ ID NO: 2) and *Lactobacillus acidophilus* HtrH-like proteinase (SEQ ID NO: 9).

10. The isolated bacterium as claimed in claim 1 wherein the bacterium comprises *Lactococcus lactis* PrtP (SEQ ID NO: 2) and *Streptococcus thermophilus* exported proteinase (SEQ ID NO: 10).

11. A composition, comprising:
an isolated bacterium comprising:
*Lactococcus lactis* PrtP (SEQ ID NO: 2); and
at least one protease selected from the group consisting of *Lactococcus lactis* HtrA (SEQ ID NO: 1), *Lactococcus lactis* PrtM (SEQ ID NO: 3), *Lactococcus lactis* CluA (SEQ ID NO: 4), *Streptococcus gordonii* SspA (SEQ ID NO: 5), *Streptococcus mutans* Pac (SEQ ID NO: 6), *Lactococcus lactis* InbA (SEQ ID NO: 7), *Lactobacillus johnsonii* HtrH-like proteinase (SEQ ID NO: 8), *Lactobacillus acidophilus* HtrH-like proteinase (SEQ ID NO: 9), and *Streptococcus thermophilus* exported proteinase (SEQ ID NO: 10)
wherein the isolated bacterium is engineered to overexpress *Lactococcus lactis* PrtP (SEQ ID NO:2) and the at least one protease selected from the group consisting of *Lactococcus lactis* HtrA (SEQ ID NO: 1), *Lactococcus lactis* PrtM (SEQ ID NO: 3), *Lactococcus lactis* CluA (SEQ ID NO: 4), *Streptococcus gordonii* SspA (SEQ ID NO: 5), *Streptococcus mutans* Pac (SEQ ID NO: 6), *Lactococcus lactis* InbA (SEQ ID NO: 7), *Lactobacillus johnsonii* HUH-like proteinase (SEQ ID NO: 8), *Lactobacillus acidophilus* HtrH-like proteinase (SEQ ID NO: 9), and *Streptococcus thermophilus* exported proteinase (SEQ ID NO: 10),
wherein the composition at least partially inhibits or at least partially removes a biofilm.

12. The composition as claimed in claim 11 wherein the composition comprises:
an isolated bacterium comprising:
*Lactococcus lactis* PrtP (SEQ ID NO: 2) and *Lactococcus lactis* HtrA (SEQ ID NO: 1).

13. The composition as claimed in claim 11 wherein the composition comprises:
an isolated bacterium comprising:
*Lactococcus lactis* PrtP (SEQ ID NO: 2) and *Lactococcus lactis* CluA (SEQ ID NO: 4).

14. The composition as claimed in claim 11 wherein the composition is in the form of a gum.

15. The composition as claimed in claim 11 wherein the composition is in the form of a cheesy tooth mask.

16. The composition as claimed in claim 11 wherein the composition further comprises at least one of more of cleaning agents, flavorants, colorants, preservatives, stabilizers, perfumes, antimicrobials, and therapeutic agents.

17. The composition as claimed in claim 11 wherein the composition is contained in an abiotic matrix.

18. The composition as claimed in claim 11 wherein the composition is ingestible.

19. The composition as claimed in claim 11 further comprising at least one antibody selected from the group consisting of *Lactococcus lactis* HtrA antibody, *Lactococcus lactis* PrtP antibody, *Lactococcus lactis* PrtM antibody, *Lactococcus lactis* CluA antibody, *Streptococcus gordonii* SspA antibody, *Streptococcus mutans* Pac antibody, *Lactococcus lactis* InbA antibody, *Lactobacillus johnsonii* HtrH-like proteinase antibody, *Lactobacillus acidophilus* HtrH-like proteinase antibody, and *Streptococcus thermophilus* exported proteinase antibody.

20. A method for removing a biofilm, comprising contacting a biofilm or a biofilm surface with a composition according to claim 11, wherein biofilm formation is reduced or the biofilm is at least partially removed.

21. The method as claimed in claim 20 wherein the composition further comprises at least one antibody selected from the group consisting of *Lactococcus lactis* HtrA antibody, *Lactococcus lactis* PrtP antibody, *Lactococcus lactis* PrtM antibody, *Lactococcus lactis* CluA antibody, *Streptococcus gordonii* SspA antibody, *Streptococcus mutans* Pac antibody, *Lactococcus lactis* InbA antibody, *Lactobacillus johnsonii* HtrH-like proteinase antibody, *Lactobacillus acidophilus* HtrH-like proteinase antibody, and *Streptococcus thermophilus* exported proteinase antibody.

22. The method as claimed in claim 20 wherein the step of contacting comprises contacting at least one of a biotic surface or biofilm on a biotic surface.

23. The method as claimed in claim 22 wherein the biotic surface comprises an oral surface.

24. The method as claimed in claim 20 wherein the step of contacting comprising contacting at least one of an abiotic surface or a biofilm formed on an abiotic surface.

25. The method as claimed in claim 20 wherein the step of contacting comprises contacting the biofilm for a period of time such that the biofilm is at least partially removed.

26. The method as claimed in claim 20 wherein the step of contacting comprises contacting the biofilm surface for a period of time such that biofilm formation on the biofilm surface is reduced.

27. The composition as claimed in claim 11 wherein the composition comprises:
an isolated bacterium comprising:
*Lactococcus lactis* PrtP (SEQ ID NO: 2) and *Lactococcus lactis* PrtM (SEQ ID NO: 3).

28. The composition as claimed in claim 11 wherein the composition comprises:
   an isolated bacterium comprising:
   *Lactococcus lactis* PrtP (SEQ ID NO: 2) and *Streptococcus gordonii* SspA (SEQ ID NO: 5).

29. The composition as claimed in claim 11 wherein the composition comprises:
   an isolated bacterium comprising:
   *Lactococcus lactis* PrtP (SEQ ID NO: 2) and *Streptococcus mutans* Pac (SEQ ID NO: 6).

30. The composition as claimed in claim 11 wherein the composition comprises:
   an isolated bacterium comprising:
   *Lactococcus lactis* PrtP (SEQ ID NO: 2) and *Lactococcus lactis* InbA (SEQ ID NO: 7).

31. The composition as claimed in claim 11 wherein the composition comprises:
   an isolated bacterium comprising:
   *Lactococcus lactis* PrtP (SEQ ID NO: 2) and *Lactobacillus johnsonii* HtrH-like proteinase (SEQ ID NO: 8).

32. The composition as claimed in claim 11 wherein the composition comprises:
   an isolated bacterium comprising:
   *Lactococcus lactis* PrtP (SEQ ID NO: 2) and *Lactobacillus acidophilus* HtrH-like proteinase (SEQ ID NO: 9).

33. The composition as claimed in claim 11 wherein the composition comprises:
   an isolated bacterium comprising:
   *Lactococcus lactis* PrtP (SEQ ID NO: 2) and *Streptococcus thermophilus* exported proteinase (SEQ ID NO: 10).

34. The composition as claimed in claim 11 further comprising at least one antibody selected from the group consisting of *Lactococcus lactis* HtrA receptor antibody, *Lactococcus lactis* PrtP receptor antibody, *Lactococcus lactis* PrtM receptor antibody, *Lactococcus lactis* CluA receptor antibody, *Streptococcus gordonii* SspA receptor antibody, *Streptococcus mutans* Pac receptor antibody, *Lactococcus lactis* InbA receptor antibody, *Lactobacillus johnsonii* HtrH-like proteinase receptor antibody, *Lactobacillus acidophilus* HtrH- like proteinase receptor antibody, and *Streptococcus thermophilus* exported proteinase receptor antibody.

35. The method as claimed in claim 20 wherein the composition further comprises at least one antibody selected from the group consisting of *Lactococcus lactis* HtrA receptor antibody, *Lactococcus lactis* PrtP receptor antibody, *Lactococcus lactis* PrtM receptor antibody, *Lactococcus lactis* CluA receptor antibody, *Streptococcus gordonii* SspA receptor antibody, *Streptococcus mutans* Pac receptor antibody, *Lactococcus lactis* InbA receptor antibody, *Lactobacillus johnsonii* HtrH-like proteinase receptor antibody, *Lactobacillus acidophilus* HtrH-like proteinase receptor antibody, and *Streptococcus thermophilus* exported proteinase receptor antibody.

* * * * *